United States Patent
Suehara et al.

(10) Patent No.: US 11,191,461 B2
(45) Date of Patent: Dec. 7, 2021

(54) OXYGEN MEASURING DEVICE

(71) Applicant: TERUMO KABUSHIKI KAISHA, Tokyo (JP)

(72) Inventors: Satoru Suehara, Kanagawa (JP); Seyedriyah Hazama, Bear (DE); Satoshi Sawada, Kanagawa (JP); Akihiro Takahashi, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 346 days.

(21) Appl. No.: 16/213,497

(22) Filed: Dec. 7, 2018

(65) Prior Publication Data
US 2019/0150801 A1 May 23, 2019

Related U.S. Application Data

(63) Continuation of application No. PCT/JP2017/021368, filed on Jun. 8, 2017.

(30) Foreign Application Priority Data

Jun. 10, 2016 (JP) .............................. JP2016-116590
Jun. 10, 2016 (JP) .............................. JP2016-116592
(Continued)

(51) Int. Cl.
*A61B 5/1459* (2006.01)
*A61B 5/20* (2006.01)
(Continued)

(52) U.S. Cl.
CPC .............. *A61B 5/1459* (2013.01); *A61B 5/01* (2013.01); *A61B 5/14507* (2013.01);
(Continued)

(58) Field of Classification Search
CPC ......... A61B 5/1459; A61B 5/201; A61B 5/01; A61B 5/14507; A61B 5/202;
(Continued)

(56) References Cited

U.S. PATENT DOCUMENTS 3,814,081 A * 6/1974 Mori .................... A61B 5/1459
600/337
5,335,305 A 8/1994 Kosa et al.
(Continued)

FOREIGN PATENT DOCUMENTS

CN 1260696 A 7/2000
JP 2739880 B2 3/1995
(Continued)

OTHER PUBLICATIONS

The extended European Search Report dated Oct. 18, 2019, by the European Patent Office in corresponding European Patent Application No. 17810410.5-1115. (8 pages).
(Continued)

*Primary Examiner* — Sean P Dougherty
*Assistant Examiner* — Alexander H Connor
(74) *Attorney, Agent, or Firm* — Buchanan Ingersoll & Rooney PC

(57) ABSTRACT

An oxygen measurement device includes a catheter including a flexible hollow shaft, the flexible shaft having an open port configured to allow urine from a bladder to flow into the open port, and a urinary passage in communication with the open port configured to discharge the urine; and an oxygen sensor including an oxygen sensor main body capable of detecting oxygen in the urine, the oxygen sensor being disposed in the catheter and configured such that the oxygen sensor main body is in contact with the urine flowing in the urinary passage.

20 Claims, 45 Drawing Sheets

(30) Foreign Application Priority Data

| Jun. 10, 2016 | (JP) | JP2016-116593 |
| Jun. 10, 2016 | (JP) | JP2016-116598 |
| Mar. 30, 2017 | (JP) | JP2017-067392 |

(51) Int. Cl.
    *A61B 5/1455*      (2006.01)
    *A61B 5/145*      (2006.01)
    *A61B 5/00*      (2006.01)
    *G01N 33/493*      (2006.01)
    *A61B 5/01*      (2006.01)

(52) U.S. Cl.
    CPC .......... *A61B 5/14552* (2013.01); *A61B 5/201* (2013.01); *A61B 5/202* (2013.01); *A61B 5/6852* (2013.01); *A61B 5/6853* (2013.01); *G01N 33/493* (2013.01); *A61B 5/14556* (2013.01)

(58) Field of Classification Search
    CPC . A61B 5/6852; A61B 5/6853; A61B 5/14556; G01N 33/493
    See application file for complete search history.

(56) References Cited

U.S. PATENT DOCUMENTS

| 5,389,217 | A | | 2/1995 | Singer | |
| 5,531,714 | A | * | 7/1996 | Dahn | A61B 5/0275 600/332 |
| 7,787,923 | B2 | * | 8/2010 | Alarcon | G01N 33/54373 600/316 |
| 2005/0113658 | A1 | | 5/2005 | Jacobson et al. | |
| 2005/0283059 | A1 | | 12/2005 | Iyer et al. | |
| 2011/0184258 | A1 | * | 7/2011 | Stafford | A61M 25/10 600/309 |
| 2013/0131592 | A1 | | 5/2013 | Selkee | |

FOREIGN PATENT DOCUMENTS

| JP | 2013-106955 A | 6/2013 | |
| WO | 02/096286 A1 | 12/2002 | |
| WO | 2006/027586 A1 | 3/2006 | |
| WO | 2014210453 A2 | 12/2014 | |
| WO | WO-2014210453 A2 * | 12/2014 | .......... A61B 5/0084 |
| WO | 2015040702 A1 | 3/2015 | |
| WO | 2015105916 A1 | 7/2015 | |

OTHER PUBLICATIONS

International Search Report (PCT/ISA/210) dated Aug. 1, 2017, by the Japanese Patent Office as the International Searching Authority for International Application No. PCT/JP2017/021368.

Written Opinion (PCT/ISA/237) dated Aug. 1, 2017, by the Japanese Patent Office as the International Searching Authority for International Application No. PCT/JP2017/021368.

Office Action (The First Office Action) dated Apr. 30, 2021, by the State Intellectual Property Office of People's Republic of China in corresponding Chinese Patent Application No. 201780030690.7 and an English Translation of the Office Action. (18 pages).

* cited by examiner

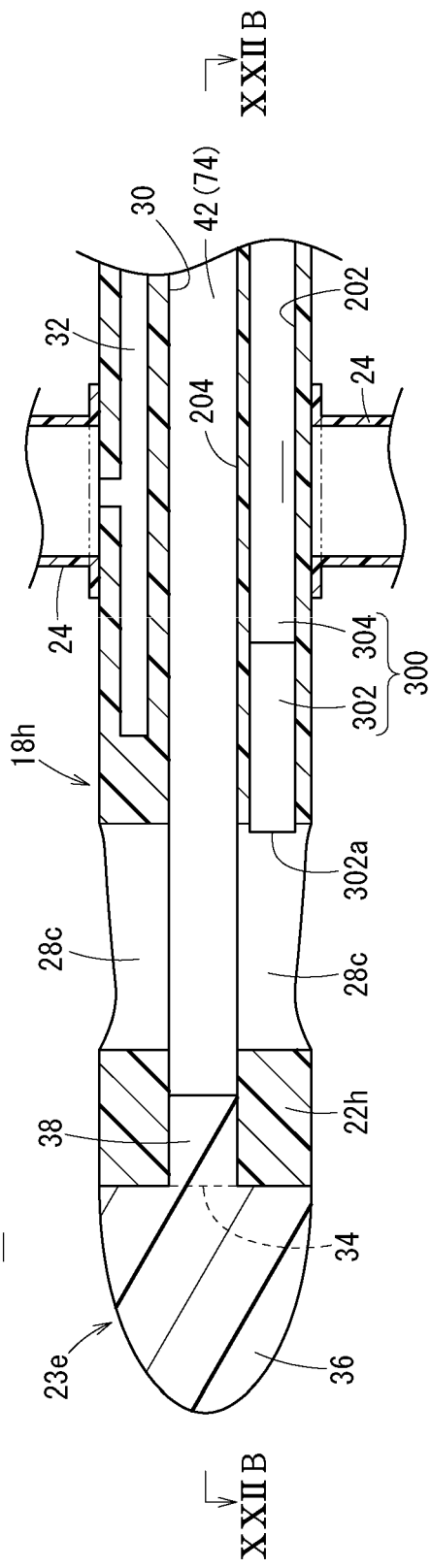

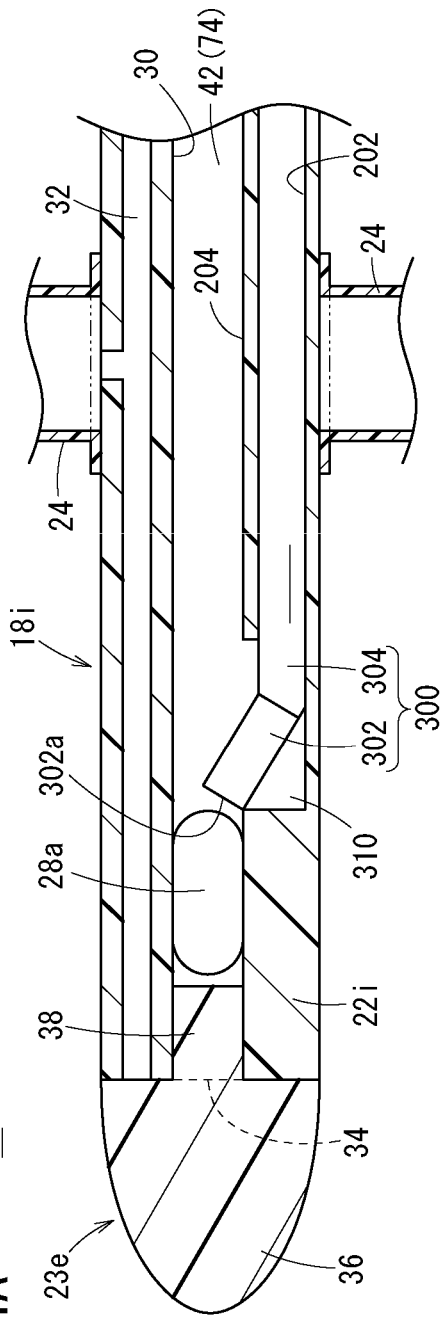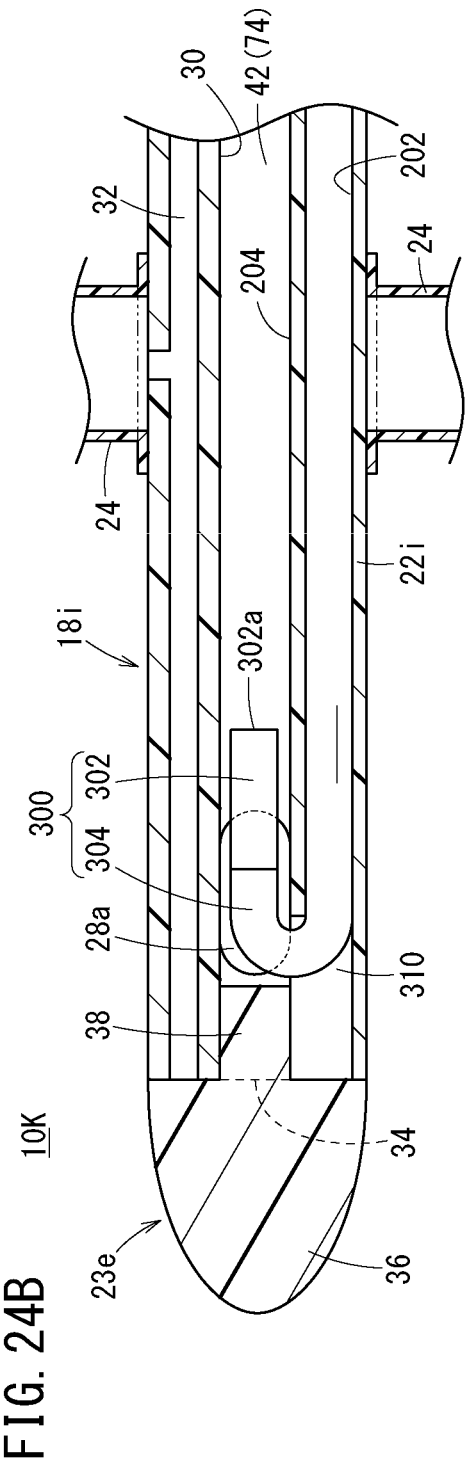

OXYGEN MEASURING DEVICE

CROSS-REFERENCES TO RELATED APPLICATIONS

This application is a continuation of International Application No. PCT/JP2017/021368 filed on Jun. 8, 2017, which claims priority to Japanese Application No. 2016-116590 filed on Jun. 10, 2016, Japanese Application No. 2016-116592 filed on Jun. 10, 2016, Japanese Application No. 2016-116593 filed on Jun. 10, 2016, Japanese Application No. 2016-116598 filed on Jun. 10, 2016, and Japanese Application No. 2017-067392 filed on Mar. 30, 2017, the entire content of all six of which is incorporated herein by reference.

TECHNICAL FIELD

The present disclosure generally relates to an oxygen measurement device detecting oxygen in urine, which is discharged from a kidney.

BACKGROUND DISCUSSION

For example, JP-B-2739880 discloses an oxygen measurement device in which an oxygen sensor is indwelt by being inserted into a bladder through a urinary passage of a urinary catheter. In the oxygen measurement device, an oxygen sensor main body of the oxygen sensor is delivered from an open port formed on a distal end portion of the urinary catheter, and is brought into contact with an epithelial wall of the bladder, and thus, oxygen of the epithelial wall is detected.

The state of the kidney can be predicted by assuming that an oxygen status in the urine reflects a tissue oxygen status of a kidney, and by measuring the oxygen in the urine. The oxygen measurement device as in JP-B-2739880 described above, detects the oxygen of the epithelial wall of the bladder, and thus, it is not necessary to detect the oxygen in the urine.

In a case where the oxygen in the urine is detected by using the oxygen sensor, the oxygen sensor main body of the oxygen sensor in the bladder is exposed from the open port of the urinary catheter, and thus, there is a case where the oxygen sensor main body is displaced, and is in contact with the bladder wall. Then, in a case where the oxygen sensor main body is in contact with the bladder wall, the contact is detected as a noise, and thus, it is not relatively easy to accurately measure the oxygen in the urine.

Further, in a case where the oxygen sensor main body is positioned in a portion where the urine remains in the bladder without being discharged, there is a concern that the oxygen in the urine discharged from the kidney is not capable of being reliably measured.

SUMMARY

An oxygen measurement device is disclosed, which is capable of accurately and reliably measuring oxygen in fresh urine, which is discharged from a kidney to the outside of the body through a bladder.

An oxygen measurement device according to the disclosure includes: a urethral catheter including a flexible hollow shaft; and an oxygen sensor including an oxygen sensor main body capable of detecting oxygen in urine, and wherein the flexible hollow shaft includes a urine introduction port configured to allow urine from a bladder to flow into the urine introduction port, and a urinary passage (or urinary tract) in communication with the urine introduction port and configured to discharge the urine, the oxygen sensor being disposed in the urethral catheter and configured such that the oxygen sensor main body is in contact with the urine flowing in the urinary passage.

According to such a configuration, the oxygen sensor main body can be in contact with the urine flowing in the urinary passage, and thus, it is possible to relatively accurately and reliably measure oxygen in fresh urine which is discharged from a kidney to the outside of the body through the bladder.

In the oxygen measurement device described above, the oxygen sensor may include the oxygen sensor main body including a fluorescent body, and a base portion in which the fluorescent body is disposed, and an optical fiber formed separately from the oxygen sensor main body, the oxygen sensor main body may be fixed to the urethral catheter such that at least a part of the fluorescent body is in contact with the urine in the urinary passage, and the optical fiber may be fixed to the urethral catheter in a state where a distal end surface of the optical fiber is positioned with respect to the fluorescent body, such that the fluorescent body can be irradiated with excitation light and fluorescence from the fluorescent body can be received.

According to such a configuration, the oxygen sensor main body including the fluorescent body, and the optical fiber are separately manufactured, and are incorporated in urethral catheter, and thus, the oxygen in the urine can be measured.

In the oxygen measurement device described above, a distal end opening portion of a lumen configuring the urinary passage may be formed on a distal end of the shaft, the urethral catheter may include a blocking portion fitted into the distal end opening portion, and the oxygen sensor main body may be fixed to the blocking portion.

According to such a configuration, the blocking portion to which the oxygen sensor main body is fixed, is fitted into the distal end opening portion from the distal end side of the shaft, and thus, it is possible to relatively accurately, easily, and reliably incorporate the oxygen sensor main body in the shaft.

In the oxygen measurement device described above, the optical fiber may be fixed to the shaft such that the distal end surface of the optical fiber is positioned in the urinary passage, and faces the fluorescent body.

According to such a configuration, the fluorescent body can be efficiently irradiated with the excitation light from the optical fiber, and the fluorescence from the fluorescent body can be efficiently received by the optical fiber.

In the oxygen measurement device described above, the optical fiber may be fixed to the urethral catheter in a state of being turned back on a distal end side from the urinary passage, such that the distal end surface of the optical fiber is positioned on a side opposite to the urinary passage sandwiching the oxygen sensor main body, and the base portion may be configured to be capable of transmitting the excitation light from the optical fiber and the fluorescence from the fluorescent body.

According to such a configuration, it is possible to improve the ease of the oxygen measurement device assembling and accuracy of the oxygen measurement device, and the ability to measure the oxygen in the urine while avoiding the contamination of the distal end surface of the optical fiber by being in contact with the urine.

In the oxygen measurement device described above, the distal end surface of the optical fiber may be in contact with or close to a surface of the base portion on a side opposite to a surface onto which the fluorescent body is applied.

According to such a configuration, it is possible to reliably bring the fluorescent body into contact with the urine, to efficiently irradiate the fluorescent body with light from the optical fiber, and to efficiently receive the fluorescence from the fluorescent body by the optical fiber.

In the oxygen measurement device described above, an arrangement hole in which a turned-back portion of the optical fiber is provided, may be formed in the blocking portion.

According to such a configuration, it is possible to dispose the optical fiber in a state of being easily turned back on the distal end side of the urinary passage.

In the oxygen measurement device described above, the optical fiber may be held in the blocking portion in a state of being disposed in the arrangement hole.

According to such a configuration, when the blocking portion is fitted into the distal end opening portion of the shaft, it is possible to accurately assemble the optical fiber with respect to the shaft, and to more reliably maintain the disposed state.

In the oxygen measurement device described above, the oxygen sensor main body may include a support portion fixed to the blocking portion, and the base portion may be fixed to the support portion, and a positioning portion positioning a distal end of the optical fiber may be disposed in the support portion.

According to such a configuration, it is possible to accurately position the distal end surface of the optical fiber with respect to the fluorescent body. In addition, the oxygen sensor main body can be fixed to the blocking portion by gripping the support portion.

In the oxygen measurement device described above, the fluorescent body may be positioned on a distal end side from the urine introduction port, and the urine introduction port may be formed such that an opening width increases along a circumferential direction towards a distal end direction of the shaft.

According to such a configuration, the flow (or discharge) of the urine in the urinary passage can be prevented from being inhibited by the fluorescent body, and thus, it is possible to more efficiently discharge the urine in a proximal end direction of the shaft, and to efficiently guide the urine guided from the urine introduction port into the urinary passage, to the fluorescent body positioned on the distal end side from the urine introduction port.

In the oxygen measurement device described above, the fluorescent body may be positioned on a proximal end side from the urine introduction port in the urinary passage.

According to such a configuration, it is possible to reliably and efficiently bring the fluorescent body into contact with the urine flowing in the urinary passage.

In the oxygen measurement device described above, the base portion may be configured to be capable of transmitting the excitation light from the optical fiber and the fluorescence from the fluorescent body, the fluorescent body may extend in a direction orthogonal to a shaft line of the shaft to be positioned on a distal end side from the base portion, and the optical fiber may be disposed on a proximal end side from the base portion such that the distal end surface of the optical fiber faces the surface of the base portion on the side opposite to the surface onto which the fluorescent body is applied.

According to such a configuration, it is possible to reliably and efficiently bring the urine in the urinary passage into contact with the fluorescent body. In addition, it is possible to efficiently irradiate the fluorescent body with the excitation light from the optical fiber, and to efficiently receive the fluorescence from the fluorescent body by the optical fiber.

In the oxygen measurement device described above, the base portion may be configured into the shape of a ring.

According to such a configuration, it is possible to relatively smoothly discharge the urine in the urinary passage in the proximal end direction of the shaft through an inner hole of the base portion.

In the oxygen measurement device described above, a holding hole into which an outer edge portion of the base portion is inserted, may be formed on a wall surface of the urinary passage.

According to such a configuration, it is possible to hold the base portion in a state or extending in the direction orthogonal to the shaft line of the shaft, by a relatively simple configuration.

In the oxygen measurement device described above, the holding hole may include a slit which is opened on an outer surface of the shaft, and has a size through which the oxygen sensor main body can be inserted into the urinary passage from the outside of the shaft, and the oxygen sensor main body may be fixed to the shaft by an adhesive agent, which seals the slit.

According to such a configuration, it is possible to relatively simply and accurately assemble the oxygen sensor main body from the outside of the shaft.

In the oxygen measurement device described above, the oxygen sensor main body may include the support portion fixed to the shaft, and the base portion may be fixed to the support portion, and the positioning portion positioning the distal end of the optical fiber may be disposed in the support portion.

According to such a configuration, it is possible to accurately position the distal end surface of the optical fiber with respect to the fluorescent body. In addition, it is possible to fix the oxygen sensor main body inside the urinary passage by gripping the support portion.

In the oxygen measurement device described above, a first engagement portion may be disposed on the wall surface of the urinary passage, and a second engagement portion to be positioned to the shaft by being engaged with the first engagement portion, may be disposed in the support portion.

According to such a configuration, it is possible to accurately incorporate the oxygen sensor main body in the urinary passage.

In the oxygen measurement device described above, the support portion may be configured into the shape of a ring, and the fluorescent body may be positioned in an inner hole of the support portion.

According to such a configuration, the urine in the urinary passage can be brought into contact with the fluorescent body while flowing to the inner hole of the support portion.

In the oxygen measurement device described above, the base portion may extend along a shaft line direction of the shaft.

According to such a configuration, it is possible to prevent the flow (or discharge) of the urine in the inner hole of the support portion from being inhibited by the base portion, compared to a case where the base portion extends along the direction orthogonal to the shaft line of the shaft.

In the oxygen measurement device described above, the fluorescent body may be positioned in a direction intersecting with a direction directed by the distal end surface of the optical fiber, and a reflection portion which guides the excitation light from the optical fiber to the fluorescent body, and guides the fluorescence from the fluorescent body into the optical fiber, may be disposed in the support portion.

According to such a configuration, for example, it is possible to irradiate the fluorescent body with the excitation light from the optical fiber by the reflection portion without bending the optical fiber, and to receive the fluorescence from the fluorescent body by the optical fiber.

In the oxygen measurement device described above, the fluorescent body may extend to slope inwardly to the shaft towards the proximal end direction of the shaft.

According to such a configuration, it is possible to efficiently bring the urine in the urinary passage into contact with the fluorescent body.

In the oxygen measurement device described above, the oxygen sensor may include an optical fiber, and the optical fiber may be fixed to the urethral catheter by the adhesive agent sealing a through hole which is formed on the outer surface of the shaft.

According to such a configuration, when the optical fiber is positioned and fixed to the urethral catheter, it is possible to improve the ease of the oxygen measurement device assembling, and to prevent the distal end surface of the optical fiber from being contaminated by the adhesive agent.

In the oxygen measurement device described above, a sensor lumen in which the optical fiber is provided, may be formed in a wall portion of the shaft.

According to such a configuration, the optical fiber is provided in the sensor lumen, and thus, it is possible to prevent the flow (or discharge) of the urine in the urinary passage from being inhibited by the optical fiber. Accordingly, it is possible to relatively smoothly discharge the urine in the urinary passage.

In the oxygen measurement device described above, a hard member (i.e., a member) formed of a material harder than a material of the shaft may be disposed in the shaft.

According to such a configuration, for example, when the shaft is inserted into a urethra, the deformation (expansion and contraction or the like) of the shaft can be suppressed by the hard member, and thus, it is possible to suppress a positional displacement between the fluorescent body and the optical fiber.

In the oxygen measurement device described above, the oxygen sensor may include a transfer portion in which the oxygen sensor main body is integrally disposed on a distal end, and extends along the shaft.

According to such a configuration, the oxygen sensor main body is integrally disposed on the distal end of the transfer portion, and thus, it is possible to rather easily assemble the oxygen sensor with respect to the shaft.

In the oxygen measurement device described above, the oxygen sensor main body may be positioned in the urine introduction port.

According to such a configuration, the oxygen sensor main body can be brought into contact with the urine flowing from the urine introduction port.

In the oxygen measurement device described above, the sensor lumen in which the transfer portion is provided, may be formed in the shaft, the urinary passage may include a urine introduction lumen extending in the shaft line direction of the shaft, and a lateral urine introduction lumen disposed in a distal end direction of the sensor lumen by being in communication with the urine introduction lumen, and the oxygen sensor may extend in the lateral urine introduction lumen such that the oxygen sensor main body is positioned in the urine introduction lumen.

According to such a configuration, the transfer portion is provided in the sensor lumen, and thus, it is possible to help prevent the flow of the urine in the urine introduction lumen from being inhibited by the transfer portion. Accordingly, it is possible to smoothly discharge the urine in the urinary passage. In addition, it is possible to efficiently bring the oxygen sensor main body into contact with the urine in the urine introduction lumen.

In the oxygen measurement device described above, the oxygen sensor main body may be positioned on a proximal end side of the urine introduction port by turning back the transfer portion on the proximal end side from the lateral urine introduction lumen towards the urine introduction lumen, the distal end opening portion of the lumen configuring the urinary passage may be formed on the distal end of the shaft, the urethral catheter may include the blocking portion fitted into the distal end opening portion, and the blocking portion may hold a portion of the transfer portion which is turned back.

According to such a configuration, it is possible to efficiently bring the oxygen sensor main body into contact with the urine introduced from the urine introduction port to the urine introduction lumen. In addition, the transfer portion can be held by the blocking portion, and thus, it is possible to suppress a positional displacement of the oxygen sensor main body in the urine introduction lumen.

In the oxygen measurement device described above, the oxygen measurement device may include a fixing portion fixing the oxygen sensor to the shaft, and the fixing portion may hold the oxygen sensor main body in the urinary passage such that the oxygen sensor main body is in contact with the urine flowing in the urinary passage.

According to such a configuration, the displacement of the oxygen sensor main body with respect to the shaft can be suppressed by the fixing portion, and thus, it is possible to improve a measurement accuracy of the oxygen sensor.

In the oxygen measurement device described above, the fixing portion may be positioned in the urinary passage or out of the urinary passage.

According to such a configuration, in a case where the fixing portion is positioned in the urinary passage, it is possible to easily hold the oxygen sensor main body in the urinary passage. In addition, in a case where the fixing portion is positioned out of the urinary passage, it is possible to help prevent the flow (or discharge) of the urine in the urinary passage from being inhibited by the fixing portion.

In the oxygen measurement device described above, the fixing portion may be positioned on a distal end side in the urinary passage.

According to such a configuration, the displacement of the oxygen sensor main body with respect to the shaft can be suppressed by the fixing portion, and thus, it is possible to improve the measurement accuracy of the oxygen sensor.

In the oxygen measurement device described above, the fixing portion may include the support portion disposed in the shaft, and the engagement portion engaged with the support portion in a state of being attached to the oxygen sensor.

According to such a configuration, it is possible to fix the oxygen sensor to the shaft by a relatively simple configuration.

In the oxygen measurement device described above, the oxygen sensor may include the transfer portion which is electrically and/or optically connected to the oxygen sensor main body, the sensor lumen in which the transfer portion is provided, may be disposed in the shaft, and the fixing portion may fix the transfer portion to an inner surface configuring the sensor lumen.

According to such a configuration, the flow (or discharge) of the urine in the urinary passage can be prevented from being inhibited by the transfer portion, and thus, it is possible to rather smoothly outflow the urine from the bladder to the urinary passage.

In the oxygen measurement device described above, a concave portion may be disposed on a surface of the fixing portion, which is exposed to the urinary passage, and the oxygen sensor main body may be positioned in the concave portion.

According to such a configuration, it is possible to more reliably bring the urine flowing in the urinary passage into contact with the oxygen sensor main body.

In the oxygen measurement device described above, the fixing portion may be liquid-tightly in contact with the inner surface configuring the sensor lumen such that the inflow of the urine, come from the urinary passage, flow out to the proximal end side of the fixing portion of the sensor lumen, is prevented.

According to such a configuration, it is possible to efficiently discharge the urine in the urinary passage.

In the oxygen measurement device described above, the oxygen sensor may include the transfer portion which is electrically and/or optically connected to the oxygen sensor main body, and the fixing portion may fix the transfer portion to the inner surface configuring the urinary passage.

According to such a configuration, it is possible to fix the oxygen sensor to the shaft by a simple configuration.

In the oxygen measurement device described above, the fixing portion may be separated from an inner surface facing the fixing portion in the urinary passage.

According to such a configuration, it is possible to smoothly discharge the urine in the urinary passage.

In the oxygen measurement device described above, the fixing portion may cover the transfer portion in the urinary passage.

According to such a configuration, it is possible to more smoothly discharge the urine in the urinary passage.

In the oxygen measurement device described above, the sensor lumen in which the oxygen sensor is provided, may be disposed in the shaft.

According to such a configuration, the flow of the urine in the urinary passage can be prevented from being inhibited by the oxygen sensor, and thus, it is possible to smoothly discharge the urine in the urinary passage.

In the oxygen measurement device described above, the oxygen sensor may include the transfer portion which is electrically connected to the oxygen sensor main body, the oxygen sensor main body may be positioned in the urinary passage, and the transfer portion may be positioned in the sensor lumen.

According to such a configuration, the urine flowing in the urinary passage can be reliably brought into contact with the oxygen sensor main body, and thus, it is possible to prevent the discharge of the urine in the urinary passage from being inhibited by the transfer portion.

In the oxygen measurement device described above, the oxygen measurement device may include the fixing portion fixing the transfer portion to the inner surface configuring the sensor lumen, the sensor lumen may extend along the shaft line direction of the shaft, and the fixing portion may be disposed such that the distal end portion is sealed in a state where the oxygen sensor is inserted into the distal end portion of the sensor lumen.

According to such a configuration, it is possible to suppress the positional displacement of the oxygen sensor main body with respect to the shaft. In addition, it is possible to prevent the flow (or discharge) of the urine in the urinary passage from being inhibited by the fixing portion. Further, the periphery of the oxygen sensor main body can be filled with the urine, and thus, it is possible to more reliably bring the urine flowing in the urinary passage into contact with the oxygen sensor main body.

In the oxygen measurement device described above, the sensor lumen may be shortened in the shaft line direction of the shaft from the urinary passage.

In the oxygen measurement device described above, the sensor lumen may include an opening portion for positioning the oxygen sensor main body in the urinary passage.

According to such a configuration, it is possible to provide the oxygen sensor main body in the urinary passage while providing the transfer portion in the sensor lumen.

In the oxygen measurement device described above, an insertion hole through which the oxygen sensor is inserted, may be disposed in the fixing portion, and a distal end of the insertion hole may be positioned in the vicinity of the urine introduction port.

According to such a configuration, it is possible to rather easily position the oxygen sensor main body in the vicinity of the urine introduction port.

In the oxygen measurement device described above, the urinary passage may include the urine introduction lumen juxtaposed (i.e., placed side by side) with the sensor lumen, and the insertion hole may be positioned on the urine introduction lumen side.

In the oxygen measurement device described above, the insertion hole may be disposed on an outer surface of the fixing portion on the urine introduction lumen side.

According to such a configuration, it is possible to position the oxygen sensor main body on the urine introduction lumen side.

In the oxygen measurement device described above, an opening area of the opening portion may be less than an opening area of the urine introduction port.

In the oxygen measurement device described above, the opening portion may be positioned on the proximal end side from the urine introduction port.

In the oxygen measurement device described above, the urinary passage may include a first urinary passage portion extending along the shaft line direction of the shaft, in which the urine introduction port is positioned, and a second urinary passage portion extending from the first urinary passage portion to the proximal end side, a flow path sectional area of the first urinary passage portion may be greater than a flow path sectional area of the second urinary passage portion.

According to such a configuration, it is possible to efficiently allow the urine in the bladder to flow into the first urinary passage portion from the urine introduction port.

In the oxygen measurement device described above, the oxygen sensor main body may be positioned in the first urinary passage portion.

According to such a configuration, it is possible to reliably bring the urine flowing into the first urinary passage portion from the bladder through the urine introduction port into contact with the oxygen sensor main body.

In the oxygen measurement device described above, the oxygen sensor main body may be positioned in the second urinary passage portion.

According to such a configuration, even in a case where a urinated volume is comparatively small, it is possible to reliably bring the urine flowing in the second urinary passage portion into contact with the oxygen sensor main body.

In the oxygen measurement device described above, the flow path sectional area of the second urinary passage portion of the distal end portion of the shaft may be less than the flow path sectional area of the second urinary passage portion of a proximal end portion of the shaft.

According to such a configuration, it is possible to smoothly discharge the urine in the second urinary passage portion towards the proximal end of the shaft.

In the oxygen measurement device described above, the sensor lumen which is disposed in parallel with the second urinary passage portion, and in which the oxygen sensor is provided, may be disposed in the shaft.

According to such a configuration, the flow of the urine in the urinary passage can be prevented from being inhibited by the oxygen sensor, and thus, it is possible to smoothly discharge the urine in the bladder, in the urinary passage.

In the oxygen measurement device described above, the oxygen sensor main body may be adjacent to the distal end side or the proximal end side of the urine introduction port in the urinary passage.

According to such a configuration, it is possible to reliably bring the urine flowing into the urinary passage from the urine introduction port, into contact with the oxygen sensor main body, and even in a case where the shaft is buckled (i.e., bent or twisted) in the position of the urine introduction port, it is possible to prevent the oxygen sensor main body from being broken.

In the oxygen measurement device described above, the oxygen sensor main body may be positioned in a direction orthogonal to the shaft line direction of the shaft, with respect to the urine introduction port.

According to such a configuration, it is possible to efficiently bring the urine flowing into the urinary passage from the urine introduction port into contact with the oxygen sensor main body.

In the oxygen measurement device described above, the urethral catheter may include a balloon which is disposed on the distal end side of the shaft, can be inflated and deflated by an inflation fluid, and the oxygen sensor main body may be positioned on the distal end side from the balloon in the shaft line direction of the shaft.

According to such a configuration, the oxygen sensor main body can be positioned in the bladder, and thus, it is possible to detect the oxygen in the urine in a comparatively stable environment (i.e., an environment where a temperature change or the like is comparatively small). In addition, the shaft can be held with respect to the bladder by the balloon, and thus, it is possible to further suppress the displacement of the oxygen sensor main body in the bladder.

In the oxygen measurement device described above, the sensor lumen in which the oxygen sensor is provided by extending along the shaft line direction of the shaft, may be disposed in the shaft, and the urine introduction port may be disposed to be positioned by being displaced to a side where the sensor lumen is positioned, from the shaft line of the shaft.

According to such a configuration, it is possible to rather easily allow the oxygen sensor main body to be adjacent to the urine introduction port.

In the oxygen measurement device described above, the center of the shaft line direction of the shaft in the urine introduction port may be disposed in a portion of the shaft, positioned on the distal end side from the sensor lumen.

According to such a configuration, it is possible to rather reliably bring the urine flowing into the urinary passage from the bladder through the urine introduction port into contact with the oxygen sensor main body.

According to the disclosure, the oxygen sensor main body can be brought into contact with the urine flowing in the urinary passage, and thus, it is possible to rather accurately and reliably measure oxygen in fresh urine which is discharged from a kidney to the outside of the body through a bladder.

In accordance with an aspect, an oxygen measurement device is disclosed, comprising: a catheter including a flexible hollow shaft, the flexible shaft having an open port configured to allow urine from a bladder to flow into the open port, and a urinary passage in communication with the open port configured to discharge the urine; and an oxygen sensor including an oxygen sensor main body capable of detecting oxygen in the urine, the oxygen sensor being disposed in the catheter and configured such that the oxygen sensor main body is in contact with the urine flowing in the urinary passage.

In accordance with a further aspect, an oxygen measurement device is disclosed, comprising: a catheter including a flexible hollow shaft, the flexible shaft having an open port configured to allow urine from a bladder to flow into the open port, and a urinary passage in communication with the open port configured to discharge the urine; an oxygen sensor including an oxygen sensor main body capable of detecting oxygen in the urine, the oxygen sensor being disposed in the catheter and configured such that the oxygen sensor main body is in contact with the urine flowing in the urinary passage; a fluorescent body and a base portion, the fluorescent body being attached to the base portion of the oxygen sensor main body; an optical fiber formed separately from the oxygen sensor main body, the oxygen sensor main body being fixed to the catheter and wherein at least a part of the fluorescent body is in contact with the urine in the urinary passage, the optical fiber being attached to the catheter in a state in which a distal end surface of the optical fiber is positioned with respect to the fluorescent body, such that the fluorescent body is capable of being irradiated with excitation light or receiving fluorescence from the fluorescent body; and a balloon arranged on a distal end portion of the shaft, the shaft having a dilation lumen for circulating a dilation fluid, and wherein the balloon is configured to be inflated and deflated according to a change in internal pressure with the dilation fluid.

In accordance with another aspect, a method is disclosed of detecting oxygen in urine discharged from a kidney, the method comprising: placing an oxygen measurement device in a bladder of a living body, the oxygen measurement device including a catheter having a flexible hollow shaft, the flexible shaft having an open port configured to allow urine from a bladder to flow into the open port, a urinary passage in communication with the open port configured to discharge the urine, an oxygen sensor including an oxygen sensor main body capable of detecting oxygen in the urine, the oxygen sensor being disposed in the catheter and configured such that the oxygen sensor main body is in contact with the urine flowing in the urinary passage, and a balloon arranged on a distal end portion of the shaft; inflating the balloon with a dilation fluid to retain the catheter inside the bladder; and measuring the oxygen in the urine discharged from the bladder with the oxygen sensor.

BRIEF DESCRIPTION OF THE DRAWINGS

FIG. 22A is a partially omitted longitudinal sectional view of an oxygen measurement device according to a ninth modification example.

FIG. 22B is a longitudinal sectional view along line XXIIB-XXIIB of FIG. 22A.

FIG. 24A is a partially omitted longitudinal sectional view of an oxygen measurement device according to a tenth modification example.

FIG. 24B is a longitudinal sectional view illustrating a configuration example of the oxygen measurement device.

DESCRIPTION OF EMBODIMENTS

Figure 1:
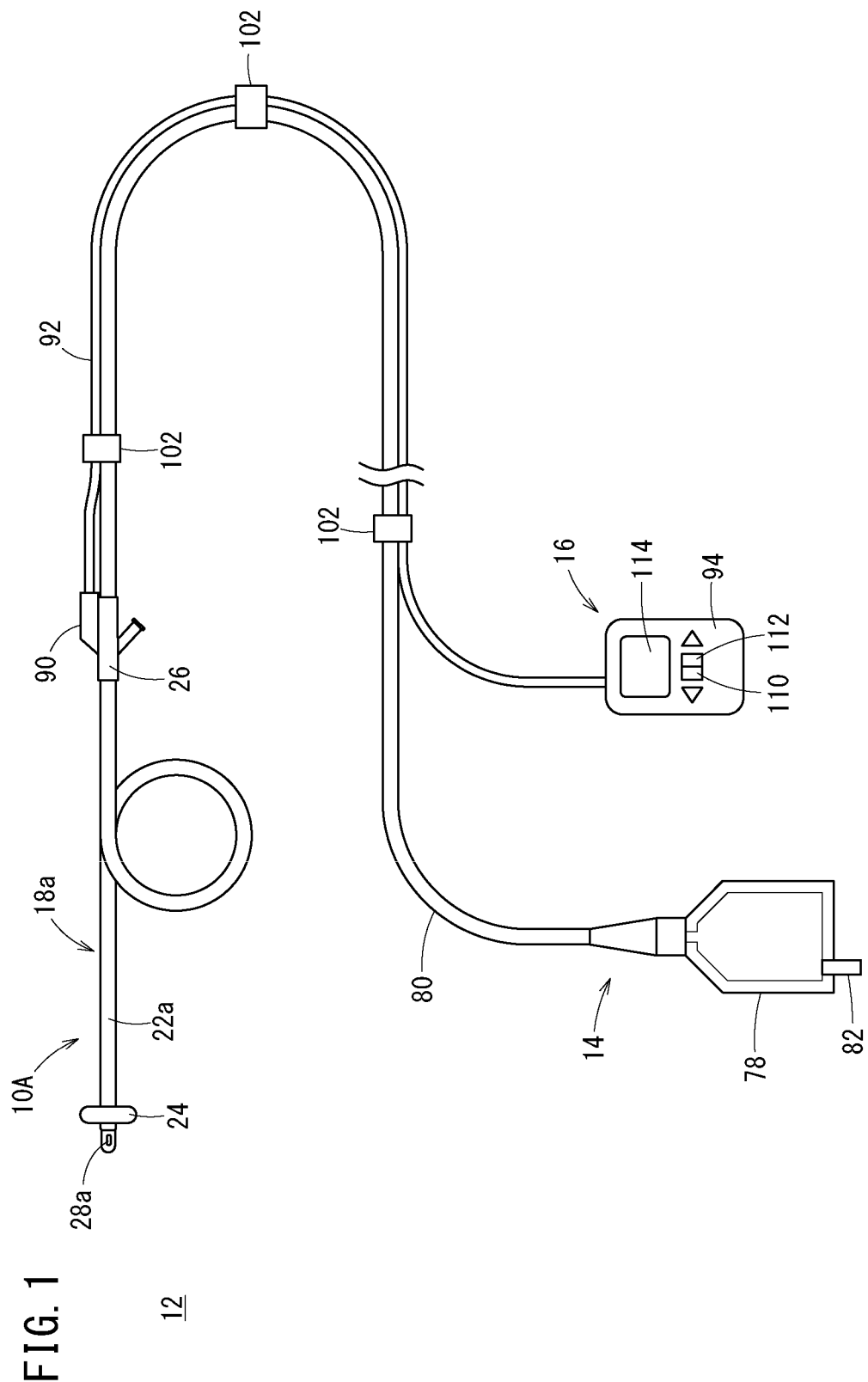
FIG. 1 is a schematic view illustrating a schematic configuration of an oxygen measurement system including an oxygen measurement device according to a first embodiment of the disclosure.

Hereinafter, an oxygen measurement device according to the disclosure will be described with reference to the attached drawings, by using embodiments suitable for a relationship with respect to an oxygen measurement system. In some cases, a dimension ratio in the drawings may be exaggerated and different from a ratio used in practice in order to facilitate the description First Embodiment An oxygen measurement system 12 according to a first embodiment of the disclosure, is to measure an oxygen partial pressure (an oxygen concentration) in urine which is discharged into a bladder 140 from a kidney, in order to predict the state of the kidney.

As illustrated in FIG. 1, the oxygen measurement system 12 includes an oxygen measurement device 10A including a urethral catheter 18a, a urine collection bag 14 (a urine collection container), and a monitoring system 16. Furthermore, in the following description, a right side of the urethral catheter 18a in FIG. 2 (i.e., the side connected to the urine collection ba) will be referred to as a "proximal end side", "proximal", or "proximal side", and a left side of the urethral catheter 18a (i.e., a side inserted into a living body) will be referred to as a "distal end side", "distal", or "distal side", and the same applies to the other drawings.

Figure 2:
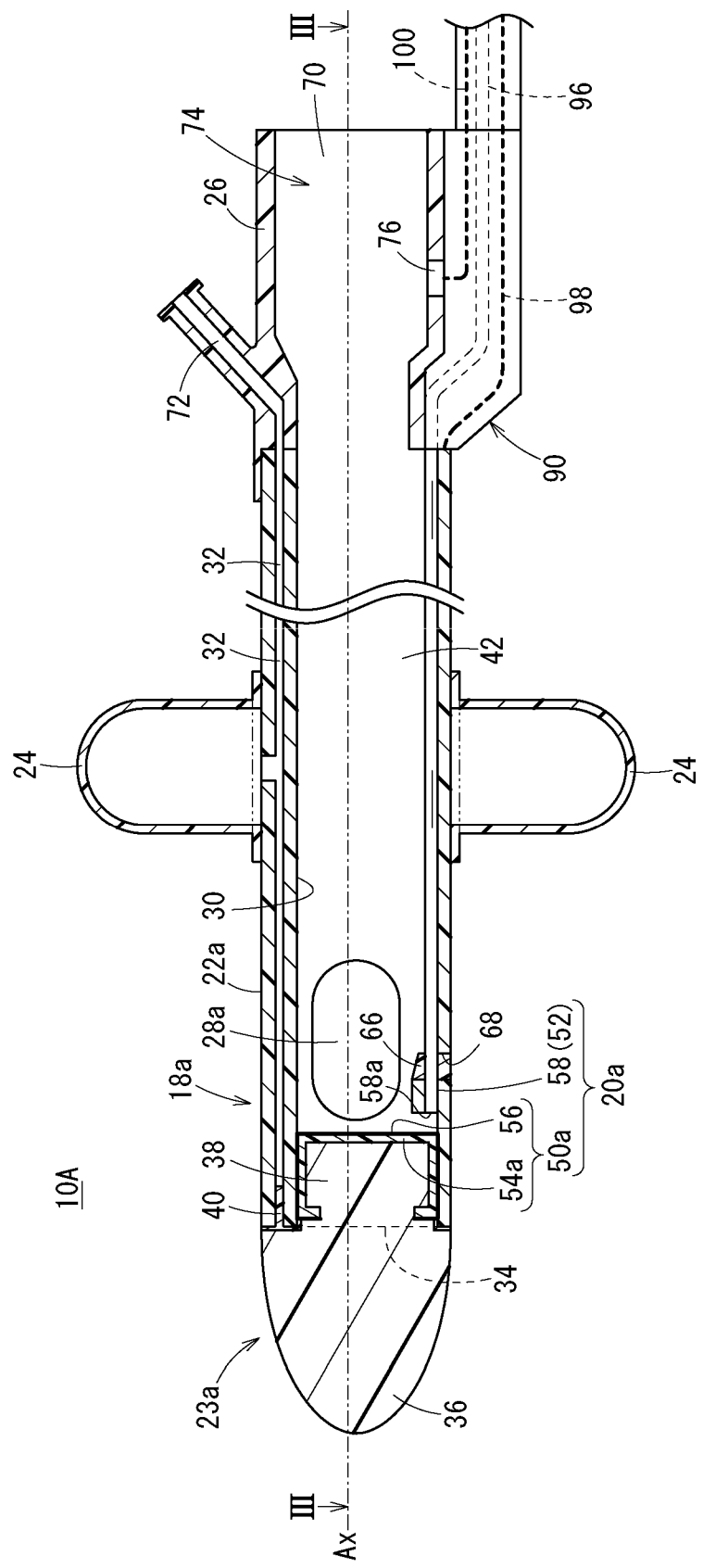
FIG. 2 is a partially omitted longitudinal sectional view of the oxygen measurement device illustrated in FIG. 1.

As illustrated in FIG. 1 and FIG. 2, the oxygen measurement device 10A includes the urethral catheter 18a and an oxygen sensor 20a. The urethral catheter 18a is a medical device which is indwelt in the living body at the time of being used, and urinates (i.e., discharges) the urine in the bladder 140 (refer to FIG. 7) to the urine collection bag 14 disposed on the outside of the body. The urethral catheter 18a includes a flexible hollow shaft 22a, a blocking portion 23a (a distal end cap) disposed on the most-distal end of the shaft 22a, a balloon 24 disposed in a distal end portion of the shaft 22a, and a hub 26 disposed in a proximal end portion of the shaft 22a.

The shaft 22a is a thin elongated tube. The shaft 22a has suitable flexibility and suitable stiffness such that a distal end portion of the urethral catheter 18a can be rather smoothly inserted into the bladder 140 through a urethra 144 (refer to FIG. 7). The shaft 22a material can include, for example, rubber such as silicone or latex, the other elastomer, vinyl chloride, polyurethane, a plastic tube, and the like.

Figure 3:
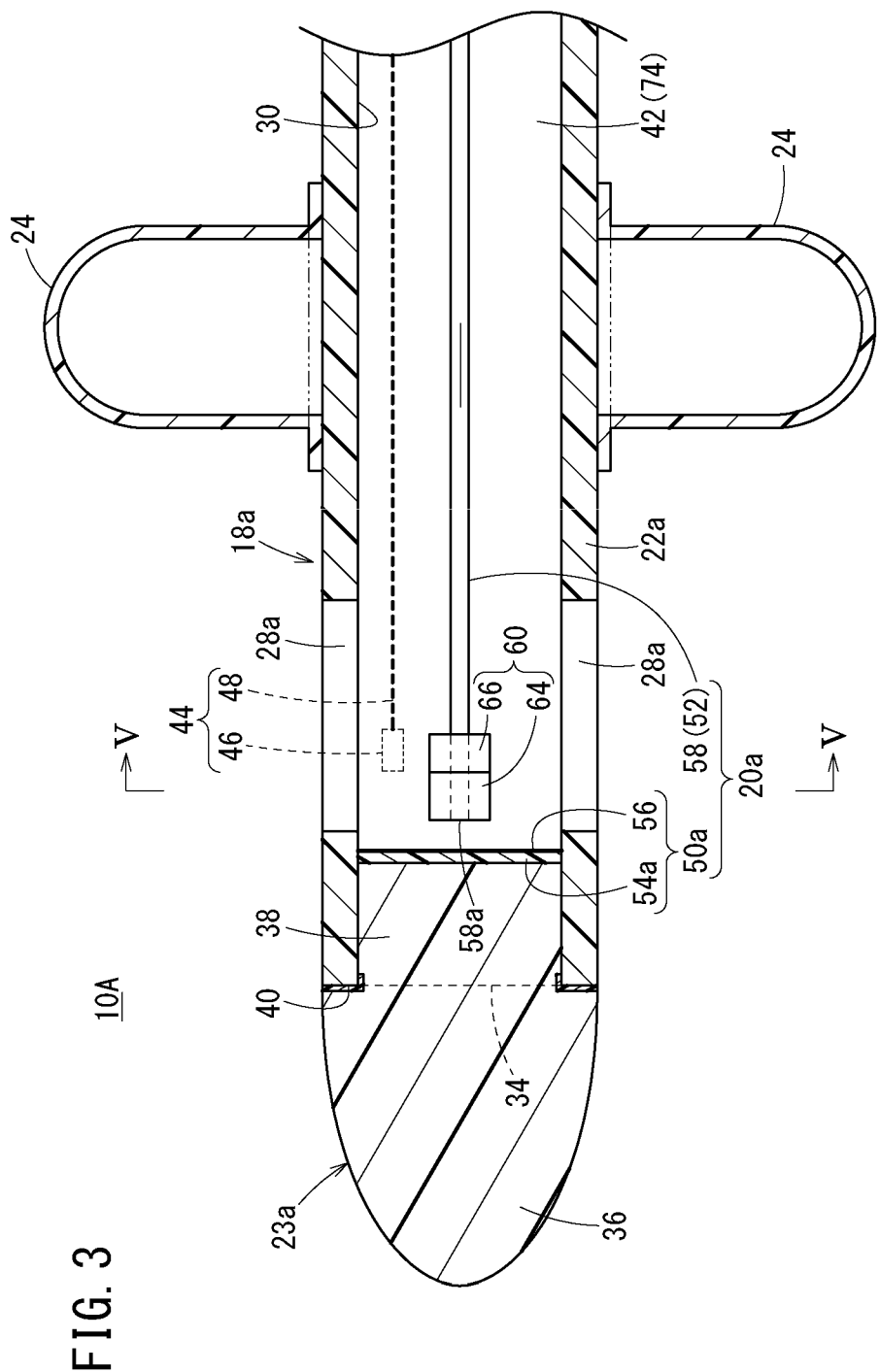
FIG. 3 is a partially omitted longitudinal sectional view along line III-III of FIG. 2.

As illustrated in FIG. 2 and FIG. 3, two urine introduction ports (open ports) 28a allowing the urine in the bladder 140 to flow into the shaft 22a, a lumen 30 which extends over the entire length of the shaft 22a by being in communication with the urine introduction port 28a, and a dilation lumen 32 for circulating a dilation fluid of the balloon 24, are formed in the shaft 22a.

Each of the urine introduction ports 28a is opened in a portion on a distal end side from the balloon 24, in an outer circumference surface of the shaft 22a. Two urine introduction ports 28a are disposed in positions facing each other. The urine introduction port 28a is an elongated hole (i.e., long hole) which extends in a longitudinal direction of the shaft 22a. Specifically, the urine introduction port 28a is formed to have a shape in which each short side of a rectangle protrudes to the outside into the shape of an arc (i.e., a shape close to an ellipse) (refer to FIG. 2). The shape, the size, the position, and the number of urine introduction ports 28a can be set as desired.

Figure 4:
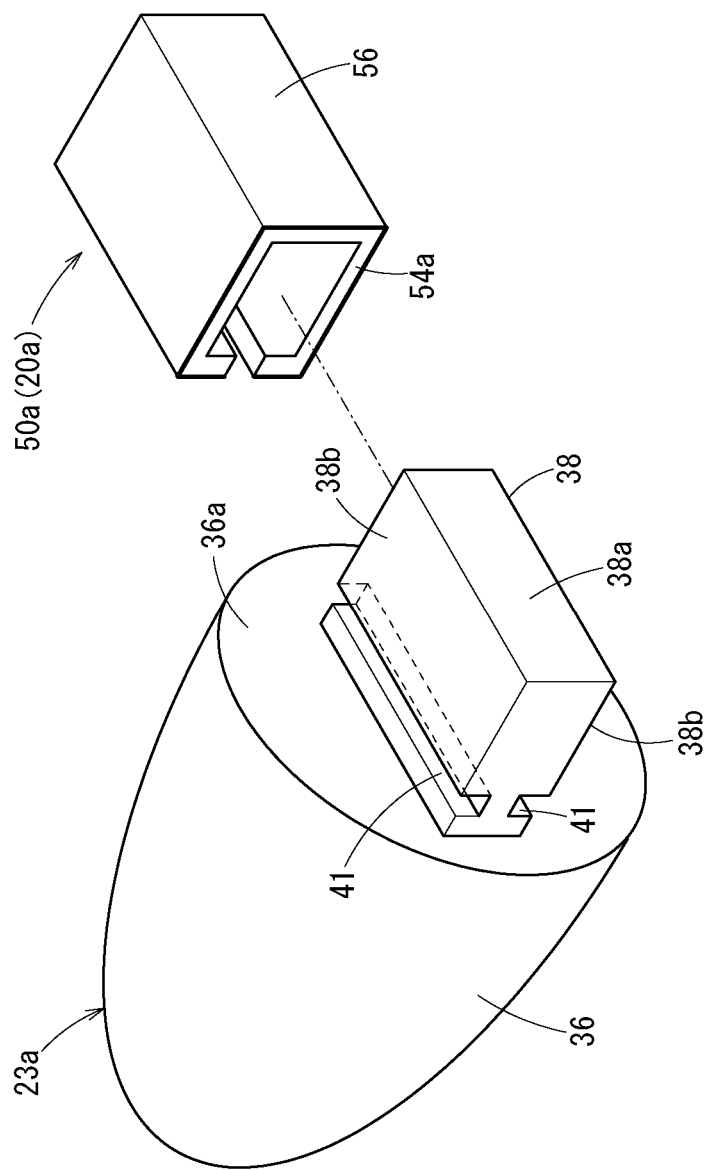
FIG. 4 is a perspective view of a blocking portion and an oxygen sensor main body illustrated in FIG. 2.

A distal end opening portion 34 of the lumen 30 is formed on a distal end surface of the shaft 22a. The distal end opening portion 34 of the lumen 30 is blocked by a blocking portion 23a. The blocking portion 23a can be made of the same material as that of the shaft 22a. As illustrated in FIG. 2 to FIG. 4, the blocking portion 23a includes a distal end bulging portion 36 which bulges on a distal end side from the shaft 22a, and a protruding portion 38 which protrudes from a proximal end surface 36a of the distal end bulging portion 36 to the proximal end direction, and is liquid-tightly fitted into the distal end opening portion 34 of the lumen 30. An outer surface of the distal end bulging portion 36 is configured as a partial curved surface of a spheroid. The proximal end surface 36a of the distal end bulging portion 36 is formed to be flat. The protruding portion 38 is formed into the shape of a rectangular parallelepiped.

In FIG. 2 and FIG. 3, the blocking portion 23a is fixed to the shaft 22a by an adhesive agent 40. The adhesive agent 40 is injected between the proximal end surface 36a of the distal end bulging portion 36 and a distal end surface 58a of the shaft 22a, and between the protruding portion 38 and a wall surface of the distal end opening portion 34 of the lumen 30. Furthermore, the adhesive agent 40 seals a distal end of the dilation lumen 32. A latch groove 41 is formed over the entire width on each of two side surfaces 38b positioned on both sides of a protruding end surface 38a of the protruding portion 38 in a height direction (a transverse direction) (refer to FIG. 4).

Figure 5:
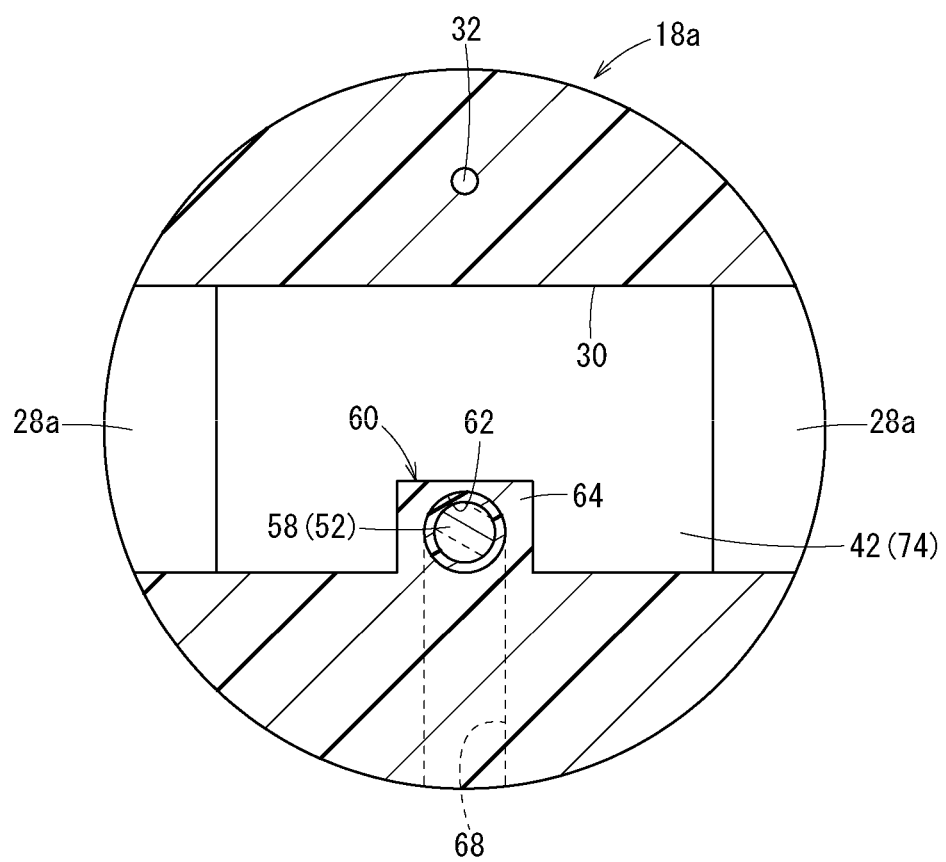
FIG. 5 is a transverse sectional view along line V-V of FIG. 3.

In the lumen 30 of the shaft 22*a*, a proximal end side from the blocking portion 23*a* functions as a urine introduction lumen 42. The urine introduction lumen 42 is disposed such that a shaft line Ax of the shaft 22*a* is positioned in the urine introduction lumen 42. A transverse sectional surface of the urine introduction lumen 42 is formed into the shape of a square (refer to FIG. 5). Here, a desired shape can be adapted to the transverse sectional surface of the urine introduction lumen 42.

As illustrated in FIG. 3, a temperature sensor 44 is embedded in the wall portion of the shaft 22*a*. The temperature sensor 44 includes a temperature sensor main body 46 (a temperature probe) for detecting a temperature in the bladder 140 (refer to FIG. 7), and a temperature transfer portion 48 which is electrically connected to the temperature sensor main body 46. The temperature sensor main body 46 is in the same position as that of the urine introduction port 28*a* in a shaft line (i.e., axial) direction of the shaft 22*a*. The temperature sensor main body 46 includes a thermoelectric couple, a resistance temperature detector, or a thermistor. The temperature sensor 44 is capable of detecting the temperature of the urine in the bladder 140 (refer to FIG. 7). Furthermore, the temperature sensor main body 46 may be disposed in the urine introduction lumen 42. In this case, the temperature of the urine discharged in a urinary passage (or urinary tract) 74 can be accurately detected.

An oxygen sensor 20*a* is disposed in the urine introduction lumen 42. The oxygen sensor 20*a* is configured as a so-called fluorescent (optical) oxygen sensor, and includes an oxygen sensor main body 50*a* capable of detecting oxygen in the urine, and a transfer portion 52 (an optical fiber 58) which is formed separately from the oxygen sensor main body 50*a*, and is provided in the urine introduction lumen 42. The oxygen sensor 20*a* is fixed (i.e., attached) to the urethral catheter 18*a* such that the oxygen sensor main body 50*a* is in contact with the urine flowing in the urine introduction lumen.

The oxygen sensor main body 50*a* includes a substrate 54*a* (a base portion), and a fluorescent body 56 which is applied to approximately the entire of one surface of the substrate 54*a*. The substrate 54*a* is made of a material which is capable of transmitting excitation light from the optical fiber 58 and fluorescence from the fluorescent body 56. The material of the substrate 54*a*, for example, can be glass, polyethylene, or the like. The substrate 54*a* has the same width dimension as the width dimension of the protruding portion 38, and at least a part of the fluorescent body 56 is disposed in the protruding portion 38 to be positioned in the urine introduction lumen 42. Specifically, the substrate 54*a* covers the protruding end surface 38*a* and two side surfaces 38*b* of the protruding portion 38 in a state of being bent approximately into a U-shape. Each end portion of the substrate 54*a* in an extending direction is bent and is fitted into each latch groove 41.

The fluorescent body 56 is made of a material emitting fluorescence by being irradiated with the excitation light from the optical fiber 58. Specifically, examples of the material of the fluorescent body 56 can include platinum porphyrin, a ruthenium complex, a pyrene derivative, and the like. The fluorescent body 56 can be subjected to coating for blocking the ambient light. Here, in accordance with an aspect, the fluorescent body 56 may not be subjected to such coating.

The transfer portion 52 is the optical fiber 58, is capable of irradiating the fluorescent body 56 with the excitation light and of receiving the fluorescence from the fluorescent body 56, and is fixed to the urethral catheter 18*a* in a state where the distal end surface 58*a* of the optical fiber 58 is positioned with respect to the fluorescent body 56. A glass optical fiber or a plastic optical fiber can be used as the optical fiber 58. The optical fiber 58 is fixed to the shaft 22*a* by a fixing portion 60 such that the distal end surface 58*a* of which the core is exposed, faces the fluorescent body 56 by being separated from the distal end surface 58*a*.

The fixing portion 60 includes a fiber support portion 64 which is disposed on a wall surface configuring the urine introduction lumen 42, and includes an insertion hole 62 into which a distal end portion of the optical fiber 58 is inserted, and an adhesive agent 66 fixing the optical fiber 58 to the wall surface of the urine introduction lumen 42. The adhesive agent 66 seals a through hole 68 which is formed on an outer surface of the shaft 22*a*. The adhesive agent 66 is preferably a material capable of transmitting light from the optical fiber 58 and the fluorescence from the fluorescent body 56. For this reason, even in a case where the adhesive agent 66 is infiltrated between the distal end surface 58*a* of the optical fiber 58 and the substrate 54*a*, the fluorescent body 56 can be irradiated with the excitation light from the optical fiber 58, and the fluorescence from the fluorescent body 56 can be received by the optical fiber 58. In the shaft line direction (i.e., axial direction) of the shaft 22*a*, the position of the distal end surface 58*a* of the optical fiber 58 is approximately the same as the position of an end portion of the urine introduction port 28*a* in a distal end direction.

The balloon 24 can be inflated and deflated according to a change in the internal pressure. That is, for example, the dilation fluid is introduced into the balloon 24, and thus, the balloon 24 is inflated, and the dilation fluid is derived from the balloon 24, and thus, the balloon 24 is deflated. FIG. 1 illustrates the balloon 24 in an inflated state.

The hub 26 is integrally molded into the shape of a hollow, by the same material as that of the shaft 22*a*, or a resin material. A urination port (i.e., urination discharge port) 70 in communication with the urine introduction lumen 42, and a balloon dilation port 72 in communication with the dilation lumen 32, are disposed (i.e., arranged) in the hub 26. The urine introduction lumen 42 and the urination port 70 form the urinary passage 74 as a urine discharge flow path of the urethral catheter 18*a*. A flow velocity sensor 76 capable of detecting a flow rate of the urine flowing through the urination port 70 is disposed on a wall surface of the urination port 70. That is, the flow velocity sensor 76 is disposed to be contact with the urine flowing through the urination port 70, or is disposed in the vicinity of the wall surface. The balloon dilation port 72 is configured such that a pressure applying device (not illustrated) for pressure-feeding the dilation fluid into the balloon 24 through the dilation lumen 32, can be connected thereto to balloon dilation port 72. In addition, the balloon dilation port 72 has a valve structure (not illustrated) in which the balloon dilation port 72 is opened in a case where the pressure applying device is connected to the balloon dilation port 72, and is blocked in a case where the pressure applying device is disconnected from the balloon dilation port 72. The hub 26 is configured such that a cable connecter 90 of the monitoring system 16 is detachable with respect to the hub 26.

As illustrated in FIG. 1, the urine collection bag 14 is configured of a so-called closed urine collection bag, and includes a bag main body 78, a urine introduction tube 80 guiding the urine in the urethral catheter 18*a* into the bag main body 78, and a urination portion 82 for discharging the urine in the bag main body 78. Such a urine collection bag 14 can be fabricated from, for example, a resin material or the like. Here, the urine collection bag 14 may be a separate bag.

As illustrated in FIG. 1 and FIG. 2, the monitoring system 16 includes the cable connecter 90 detachable with respect to the hub 26, an elongated transfer cable 92 interlocked with the cable connecter 90, and a monitor main body portion 94 interlocked with the transfer cable 92. An oxygen cable 96 optically connected to the transfer portion 52, a temperature cable 98 electrically connected to the temperature transfer portion 48, and a flow rate cable 100 electrically connected to the flow velocity sensor 76, are disposed in the cable connecter 90. The oxygen cable 96 is an optical fiber, and the temperature cable 98 and the flow rate cable 100 are electrical wires. The oxygen cable 96, the temperature cable 98, and the flow rate cable 100 are integrated into one by the transfer cable 92, and extend to the monitor main body portion 94.

The transfer cable 92 is provided along the urine introduction tube 80, and is latched (i.e., connected or fixed) with respect to the urine introduction tube 80 by a plurality of latch members 102 (banding bands). Accordingly, it is possible to prevent the urine introduction tube 80 and the transfer cable 92 from becoming an obstacle (or impediment) at the time of using the oxygen measurement device 10A.

Figure 6:
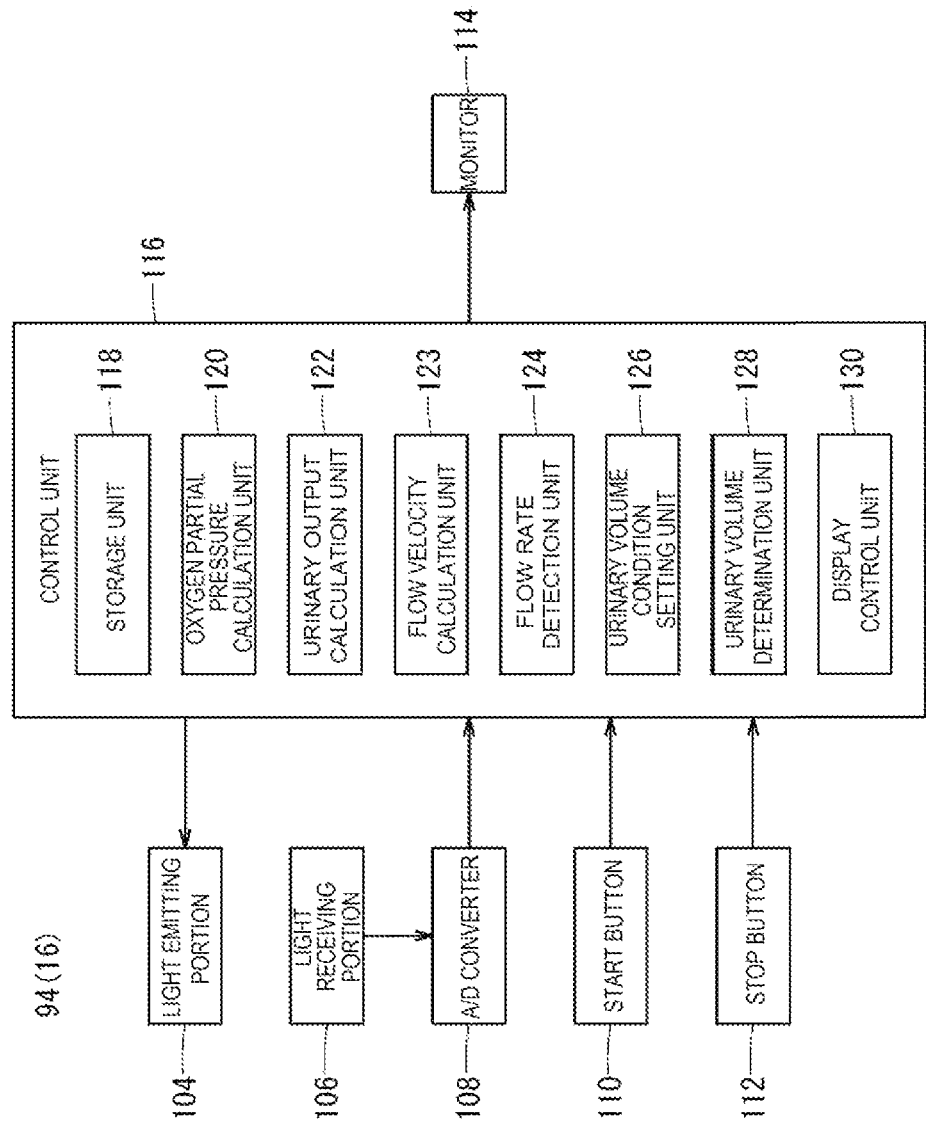
FIG. 6 is a block diagram illustrating a monitor main body portion illustrated in FIG. 1.

As illustrated in FIG. 6, the monitor main body portion 94 includes a light emitting portion 104, a light detection portion 106, an A/D converter 108, a start button 110, a stop button 112, a monitor 114, and a control unit 116.

The light emitting portion 104, for example, is a light emitting diode, and emits excitation light having a predetermined wavelength to the oxygen cable 96. The light detection portion 106, for example, is a photodiode, and the fluorescence transferred from the oxygen cable 96 is incident on the light detection portion 106. The A/D converter 108 converts a light receiving signal of the light detection portion 106 into a digital value, and outputs the digital value to the control unit 116.

The start button 110 is a button for starting the measurement of an oxygen partial pressure in the urine. The stop button 112 is a button stopping the measurement of the oxygen partial pressure in the urine. In addition, a power source button (not illustrated) or the like is disposed in the monitor main body portion 94.

The monitor 114 is configured to be capable of displaying the oxygen partial pressure in the urine, which is calculated by the control unit 116. The monitor 114 can be a so-called full-dot liquid crystal type display, and is capable of color-displaying predetermined information. The monitor 114 has a touch panel function, and also functions as an input unit inputting the predetermined information. A pointing device of a mouse cursor type, a touch pen type, a touch pad type, or the like can be used as an input format of the monitor 114, in addition to a touch panel type. Furthermore, the input of information with respect to the monitor main body portion 94 is not limited to the input according to the monitor 114, and the information may be input by an input button or the like.

The control unit 116 includes a storage unit 118 and various function realization units. Furthermore, the function realization unit is a software function unit of which the function is realized by executing a program stored in the storage unit 118 by a central processing unit (CPU), and can be realized by a hardware function unit formed of an integrated circuit such as a field-programmable gate array (FPGA). The storage unit 118 includes a writable non-volatile memory (for example, a flash memory), and is capable of storing the information input through the monitor 114, or the information calculated by the control unit 116.

The control unit 116 can include a storage unit 118, an oxygen partial pressure calculation unit 120, a urinary output calculation unit 122, a flow velocity calculation unit 123, a flow rate detection unit 124, a urinary volume condition setting unit 126, a urinary volume determination unit 128, and a display control unit 130. In addition, the control unit 116 includes a temperature input unit (not illustrated) into which an output signal of the temperature sensor 44 is input, and a flow velocity input unit (not illustrated) into which an output signal of the flow velocity sensor 76 is input.

The oxygen partial pressure calculation unit 120 calculates the oxygen partial pressure in the urine, on the basis of an output signal of the oxygen sensor 20a and the output signal of the temperature sensor 44. The urinary output calculation unit 122 calculates a urinary volume, on the basis of the output signal of the flow velocity sensor 76. The flow velocity calculation unit 123 calculates the flow velocity of the urine in the urinary passage 74, on the basis of the output signal from the flow velocity sensor 76.

The urinary volume condition setting unit 126 sets a predetermined urinary volume condition. Specifically, the urinary volume condition setting unit 126 sets a first urinary volume determination value and a second urinary volume determination value. The first urinary volume determination value, for example, is calculated by multiplying a first urinary volume reference value (0.5 ml/kg/h), which is used for determining a first stage and a second stage of acute kidney impairment (AKI), and a body weight of a patient together. The second urinary volume determination value is calculated by multiplying a second urinary volume reference value (0.3 ml/kg/h), which is used for determining a third stage of the acute kidney impairment, and the body weight of the patient together. In accordance with an aspect, the urinary volume condition setting unit 126 is capable of setting a desired condition. The urinary volume determination unit 128 determines the satisfaction by comparing the urine volume calculated by the urinary output calculation unit 122 with the predetermined volume condition.

The display control unit 130 changes a display format of the oxygen partial pressure to be displayed on the monitor 114, according to the flow velocity of the urine, which is acquired on the basis of the output signal of the flow velocity sensor 76. Specifically, for example, the display control unit 130 can display the oxygen partial pressure on the monitor 114 in a first display format in a case where the flow rate detection unit 124 determines that the flow velocity of the urine is greater than or equal to a predetermined value (greater than or equal to a reference flow velocity V0), and displays the oxygen partial pressure on the monitor 114 in a second display format different from the first display format in a case where the flow rate detection unit 124 determines that the flow velocity of the urine is less than the predetermined value (less than the reference flow velocity V0). The display control unit 130 displays a graph illustrating a time change in the oxygen partial pressure, on the monitor 114. In a case where the urinary volume determination unit 128 determines the satisfaction by comparing the urine volume calculated by the urinary output calculation unit 122 with the predetermined volume condition, the display control unit 130 displays the effect on the monitor 114.

Next, the assembly of the oxygen sensor 20a with respect to the urethral catheter 18a will be described. As illustrated in FIG. 2 to FIG. 5, in this embodiment, the optical fiber 58 is provided in the urine introduction lumen 42, and the distal end is inserted into the insertion hole 62 of the fiber support portion 64. Then, the adhesive agent 66 is injected from the outside of the shaft 22a through the through hole 68, and thus, the optical fiber 58 is fixed to the shaft 22a. In addition, in a state where the substrate 54a of the oxygen sensor main body 50a is bent into a U-shape, the both end portions are latched on each of the latch grooves 41 of the protruding portion 38. Then, in a state where the adhesive agent 66 is applied onto the distal end surface 58a of the shaft 22a and the wall surface configuring the distal end opening portion 34, the blocking portion 23a holding the oxygen sensor main body 50a is fitted into the distal end opening portion 34 of the shaft 22a. Then, the blocking portion 23a is fixed to the shaft 22a, and the oxygen sensor main body 50a is fixed to the shaft 22a. Accordingly, the fluorescent body 56 and the distal end surface 58a of the optical fiber 58 can be accurately positioned.

Next, the use of the oxygen measurement device 10A will be described.

Figure 7:
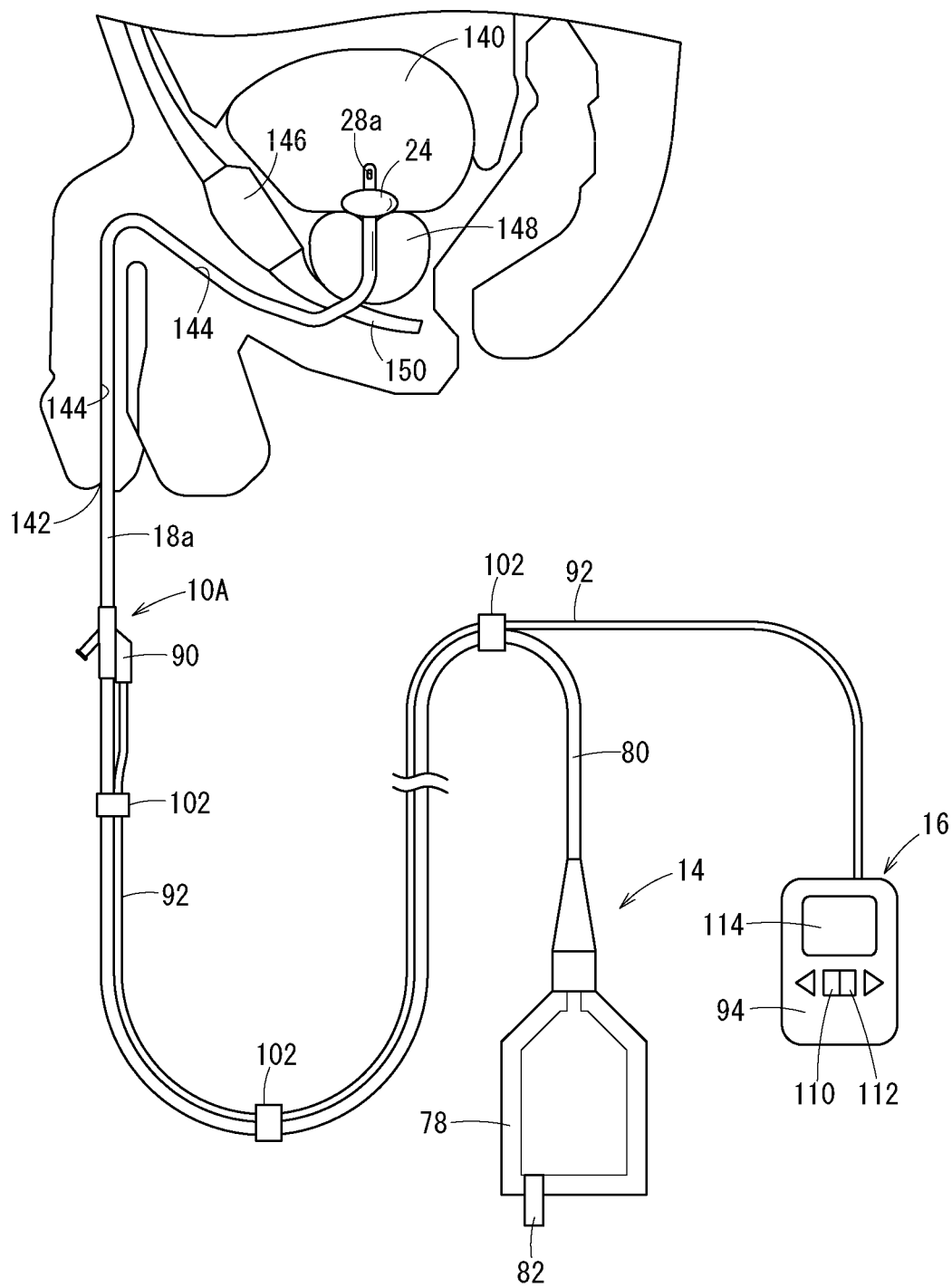
FIG. 7 is a schematic view illustrating a using method of the oxygen measurement system.
Figure 8:
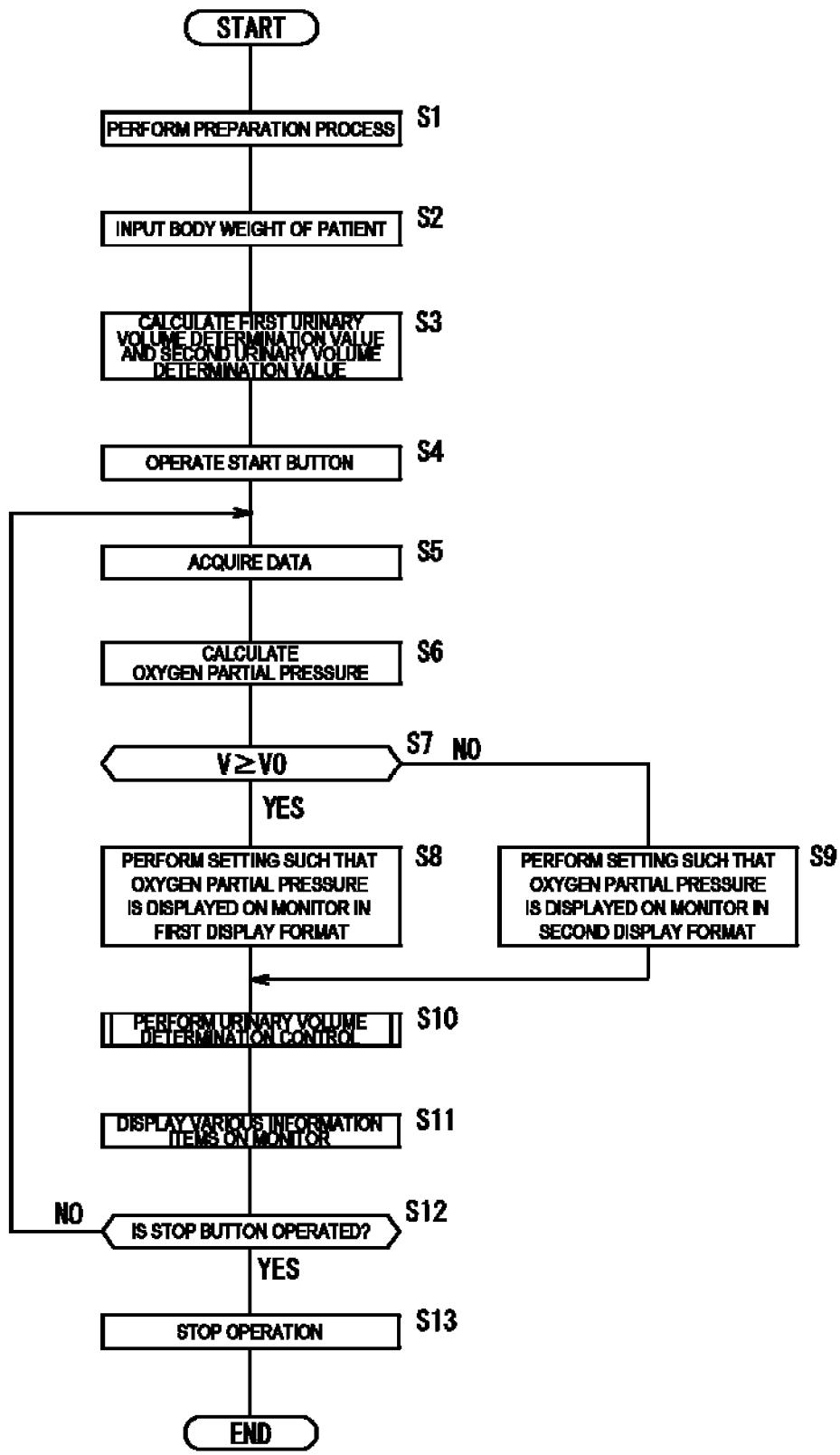
FIG. 8 is a first flowchart illustrating the using method of the oxygen measurement system.

As illustrated in FIG. 7 and FIG. 8, first, a preparation process is performed (Step S1 of FIG. 8). In the preparation process, the distal end portion of the urethral catheter 18a is indwelt in the bladder 140. Specifically, the distal end of the shaft 22a, which is coated with a lubricant jelly, is inserted into the urethra 144 from a urethral orifice 142 of the patient, and a state is obtained in which the urine introduction port 28a and the balloon 24 are disposed in the bladder 140. Furthermore, a stylet (not illustrated) may be inserted into the urine introduction lumen 42 of the shaft 22a, sufficient stiffness may be applied to the shaft 22a, and thus, the urethral catheter 18a may be easily inserted into the bladder 140.

After that, the dilation fluid is pressure-fed from the balloon dilation port 72 to the dilation lumen 32 with the pressure applying device (not illustrated) (refer to FIG. 2), and thus, the balloon 24 is inflated. Accordingly, the urethral catheter 18a is retained in the body, and the distal end side from the balloon 24 in the shaft 22a is indwelt in the bladder 140. Furthermore, in FIG. 7, a reference numeral of 146 is a pubic bone, a reference numeral of 148 is a prostatic gland, and a reference numeral of 150 is an external urinary sphincter.

In a case where the distal end portion of the urethral catheter 18a is indwelt in the bladder 140, the urine in the bladder 140 can be urinated to the urine collection bag 14 through the urethral catheter 18a. At this time, in the urethral catheter 18a, the urine in the bladder 140 flows into the urinary passage 74 from the urine introduction port 28a.

In addition, a user inputs the body weight of the patient into the monitor main body portion 94 (Step S2). Then, the urinary volume condition setting unit 126 calculates the first urinary volume determination value and the second urinary volume determination value, on the basis of the input body weight of the patient (Step S3).

After that, the user operates the start button 110 (Step S4). Accordingly, the measurement of the oxygen partial pressure in the urine is started. In a case where the start button 110 is operated (i.e., activated by, for example, pushing the start button), the measurement of the oxygen partial pressure in the urine is continuously or intermittently (for example, every 5 minutes) performed until the stop button 112 is operated (i.e., activated, by pushing the stop button).

Specifically, the control unit 116 acquires various data items (Step S5). That is, the control unit 116 acquires the output signal of the temperature sensor 44 and the output signal of the flow velocity sensor 76. In addition, the control unit 116 controls the light emitting portion 104, and emits excitation light having a predetermined wavelength. Then, the excitation light emitted from the light emitting portion 104 is transferred to the optical fiber 58 through the oxygen cable 96, and is emitted to the fluorescent body 56 of the oxygen sensor main body 50a from the distal end surface 58a of the optical fiber 58. The fluorescent body 56 irradiated with the excitation light, is transitioned from a ground state to an excitation state, and returns to the ground state while radiating fluorescence. At this time, in a case where oxygen molecules exist around the fluorescent body 56, the excitation energy is absorbed into the oxygen molecules according to a mutual interaction, and a fluorescence light emitting intensity decreases. Such a phenomenon is referred to as a quenching phenomenon, and the fluorescence light emitting intensity is in reverse proportion to an oxygen molecule concentration. The fluorescence of the fluorescent body 56 is incident from the distal end surface 58a of the optical fiber 58, and is guided to the light detection portion 106 through the optical fiber 58 and the oxygen cable 96. A light receiving signal of the light detection portion 106 is converted into a digital signal by the A/D converter 108, and the digital signal is input into the control unit 116. Accordingly, the output signal of the oxygen sensor 20a is acquired.

After that, the oxygen partial pressure calculation unit 120 calculates the oxygen partial pressure in the urine, on the basis of the output signal of the oxygen sensor 20a (the output signal of the A/D converter 108) and the output signal of the temperature sensor 44 (Step S6). In addition, the flow rate detection unit 124 determines whether or not a flow velocity V of the urine, which is acquired on the basis of the output signal of the flow velocity sensor 76, is greater than or equal to the predetermined value (the reference flow velocity V0) (Step S7). The reference flow velocity V0 is stored in advance in the storage unit 118.

In a case where the flow rate detection unit 124 determines that the flow velocity V is greater than or equal to the reference flow velocity V0 (Step S7: YES), the display control unit 130 performs setting such that the calculated oxygen partial pressure is displayed on the monitor 114 in the first display format (Step S8). On the other hand, in a case where the flow rate detection unit 124 determines that the flow velocity V is less than the reference flow velocity V0 (Step S7: NO), the display control unit 130 performs setting such that the calculated oxygen partial pressure is displayed on the monitor 114 in the second display format (Step S9).

Figure 9:
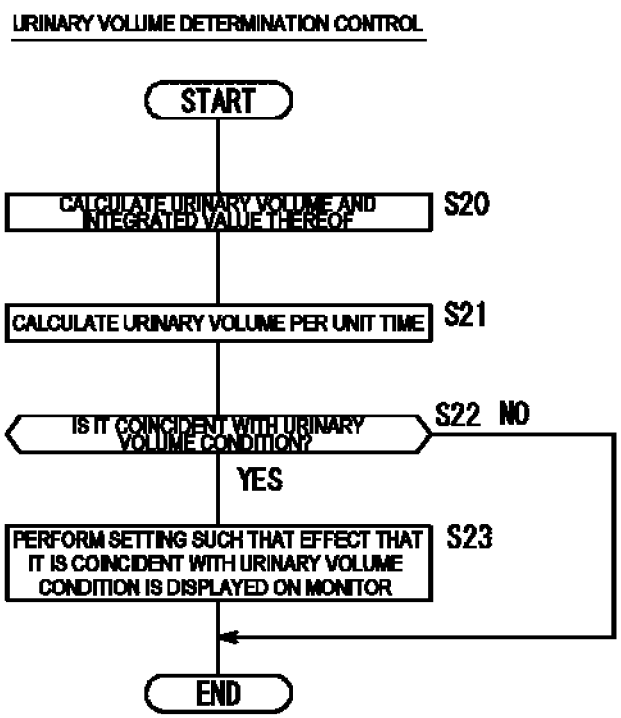
FIG. 9 is a second flowchart illustrating the using method of the oxygen measurement system.

Subsequently, urinary volume determination control (Step S10) is performed. As illustrated in FIG. 9, in the urinary volume determination control (Step S10), first, the urinary output calculation unit 122 calculates the urinary volume and an integrated value of the urinary volume (Step S20). That is, the urinary output calculation unit 122 calculates the urinary volume, on the basis of the output signal of the flow velocity sensor 76. The calculated urinary volume is stored in the storage unit 118. Then, the urinary output calculation unit 122 calculates the integrated value of the urinary volume by adding the urinary volume calculated in the current measurement to the urinary volume stored in the storage unit 118. The integrated value of the urinary volume is stored in the storage unit 118.

After that, the urinary output calculation unit 122 calculates the urinary volume per unit time (for example, per 1 hour), on the basis of the integrated value of the urinary volume (Step S21). Subsequently, the urinary volume determination unit 128 determines whether or not the urinary volume per unit time is coincident (i.e., occurring at the same time) with the urinary volume condition (Step S22).

Specifically, the urinary volume determination unit 128 determines the stage of AKI, whether the first stage, the second stage, or the third stage, based on the calculated urinary volume per unit time corresponds. That is, in a case where the state in which the urinary volume per unit time is less than the first urinary volume determination value, is continued for 6 hours or longer, the urinary volume determination unit 128 determines that the calculated urinary volume per unit is coincident with the first stage. In addition, in a case where the state in which the urinary volume per unit time is less than the first urinary volume determination value, is continued for 12 hours or longer, the urinary volume determination unit 128 determines that the calculated urinary volume per unit is coincident with the second stage. Further, in a case where the state in which the urinary volume per unit time is less than the second urinary volume determination value, is continued for 24 hours or longer or a state in which there is no urinary volume, is continued for 12 hours or longer, the urinary volume determination unit 128 determines that the calculated urinary volume per unit is coincident with the third stage.

In a case where the urinary volume determination unit 128 determines that the calculated volume per unit is coincident with any one of the first stage to the third stage of AKI (Step S22: YES), the display control unit 130 performs setting such that the effect that the calculated urinary volume per unit is coincident with the urinary volume condition (the effect that it is the first stage to the third stage) is displayed on the monitor 114 (Step S23), and proceeds to the processing of Step S11 of FIG. 8. On the other hand, in a case where the urinary volume determination unit 128 determines that the calculated urinary volume per unit is not coincident with any one of the first stage to the third stage of AKI (Step S22: NO), the display control unit 130 proceeds to the processing of Step S11 of FIG. 8.

Figure 10:
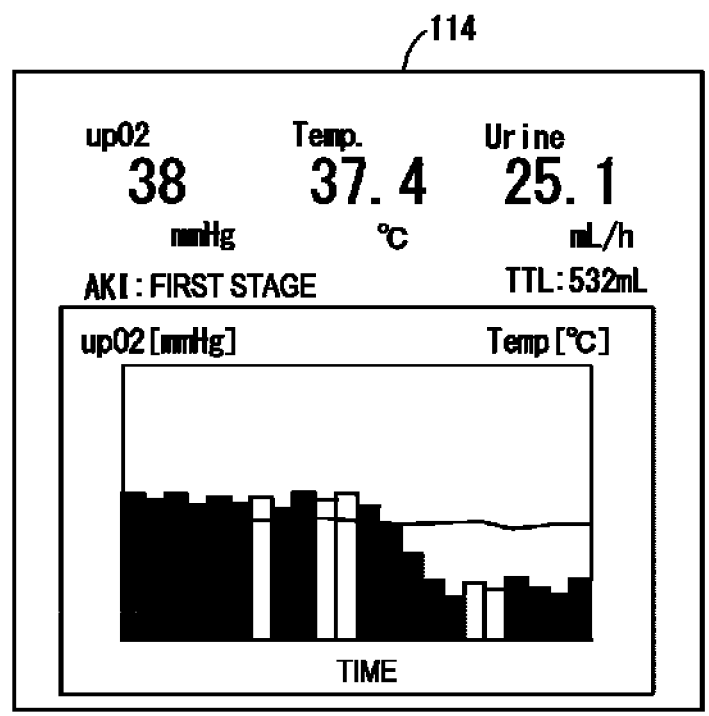
FIG. 10 is a first diagram illustrating a measurement result of the oxygen measurement system, which is displayed on a monitor.

After that, in Step S11, the display control unit 130 displays various information items on the monitor 114. Specifically, as illustrated in FIG. 10, the display control unit 130, for example, displays the oxygen partial pressure, the temperature in the bladder, the urinary volume, and the integrated value of the urinary volume on the monitor 114 as a numerical value, and displays a time change in the oxygen partial pressure and a time change in the temperature in the bladder on the monitor 114 in a graph. In addition, in a case where the urinary volume determination control determines that the calculated urinary volume per unit corresponds to any one of the first stage to the third stage of AKI (Step S22: YES), the display control unit 130 displays the effect on the monitor 114. Furthermore, in a case where the urinary volume determination control determines that the calculated urinary volume per unit does not correspond to any one of the first stage to the third stage of AKI (Step S22: NO), the display control unit 130 does not display AKI on the monitor 114.

In an example of FIG. 10, the oxygen partial pressure is 38 mmHg, the temperature in the bladder is 37.4° C., the urinary volume per unit time is 25.1 mL/h, the integrated urinary volume is 532 ml, and AKI is displayed as the first stage. In addition, the time change in the oxygen partial pressure is displayed in a bar graph, and the time change in the temperature in the bladder is displayed in a line graph. That is, a horizontal axis indicates time, one vertical axis indicates an oxygen partial pressure (mmHg), and the other vertical axis indicates a temperature (° C.). In addition, in the bar graph, a portion, which is blacked out, is a portion displaying the oxygen partial pressure in the first display format, and a portion, which is not blacked out, is a portion displaying the oxygen partial pressure in the second display format. That is, in the bar graph, the oxygen partial pressure of the portion which is blacked out, is the oxygen partial pressure in the urine when the flow velocity V of the urine is greater than or equal to the reference flow velocity V0, and the oxygen partial pressure of the portion which is not blacked out, is the oxygen partial pressure in the urine when the flow velocity V of the urine is less than the reference flow velocity V0.

The first display format and the second display format of the oxygen partial pressure are not limited to the example of FIG. 10. For example, in the bar graph, the first display format may be displayed in a state of not being blacked out, and the second display format may be displayed in a state of being blacked out.

Figure 11A:
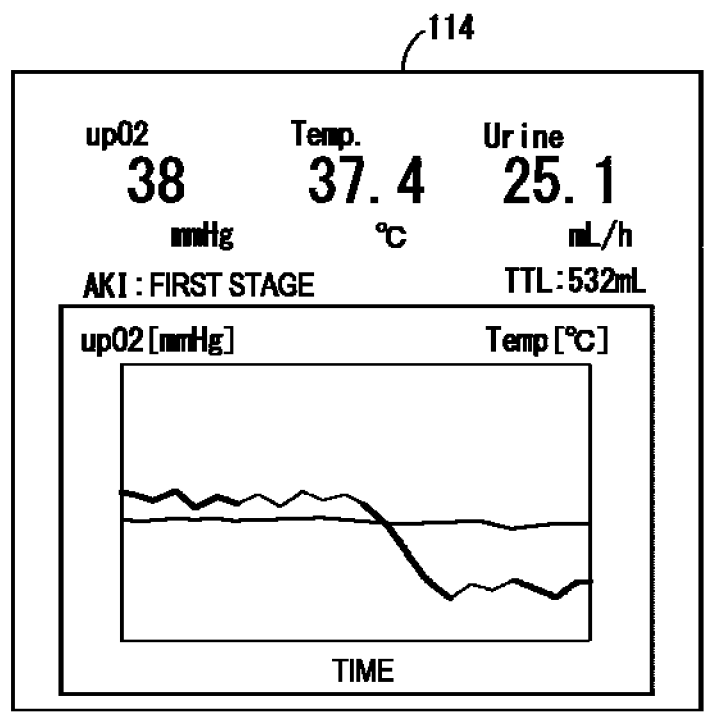
FIG. 11A is a second diagram illustrating the measurement result of the oxygen measurement system, which is displayed on the monitor.

In addition, as illustrated in FIG. 11A, the display control unit 130 may display the time change in the oxygen partial pressure on the monitor 114 in a line graph. In this case, in the line graph, a thick line portion is a portion displaying the oxygen partial pressure in the first display format, and a thin line portion is a portion displaying the oxygen partial pressure in the second display format. Alternatively, for example, the first display format may be displayed with a thin line, and the second display format may be displayed with a thick line.

Figure 11B:
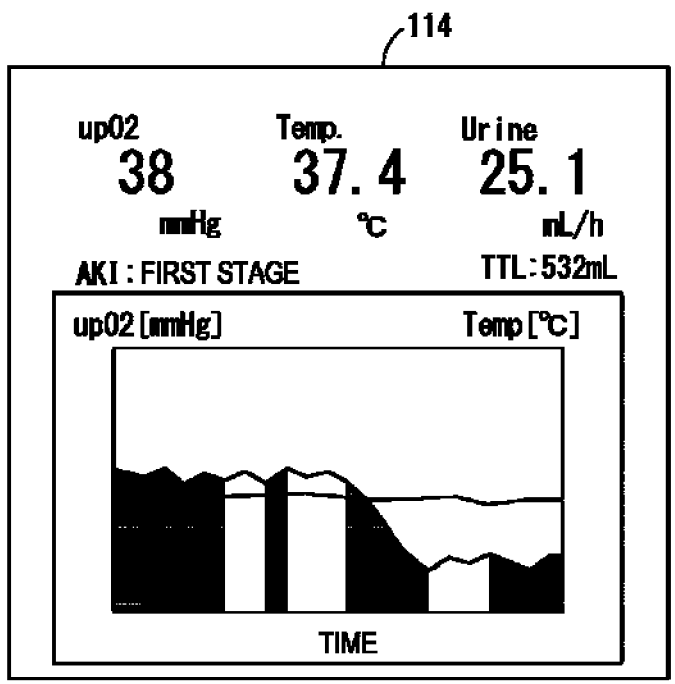
FIG. 11B is a third diagram illustrating the measurement result of the oxygen measurement system, which is displayed on the monitor.

Further, as illustrated in FIG. 11B, in the line graph, a portion of which a lower side from a line segment indicating the value of the oxygen partial pressure is blacked out, may be set to the first display format of the oxygen partial pressure, and a portion of which the lower side is not blacked out, may be set to the second display format of the oxygen partial pressure. Alternatively, for example, the first display format may be displayed in a state where the lower side is not blacked out, and the second display format may be displayed in a state where the lower side is blacked out.

After that, the control unit 116 determines whether or not the stop button 112 is operated (i.e., activated or pushed) (Step S12). In a case where the stop button 112 is not operated (Step S12: NO), the process proceeds to processing after Step S5. On the other hand, in a case where the stop button 112 is operated (Step S12: YES), the control unit 116 stops the operation of the oxygen measurement (Step S13). That is, the emission of the excitation light of the light emitting portion 104 is stopped. In this stage, oxygen measurement processing of the current flowchart is ended.

Next, the effect of this embodiment will be described.

The oxygen measurement device 10A includes the urethral catheter 18a including the flexible hollow shaft 22a, and the oxygen sensor 20a including the oxygen sensor main body 50a capable of detecting the oxygen in the urine. The urine introduction port 28a allowing the urine in the bladder 140 to flow into the urine introduction port 28a, and the urinary passage 74, which is in communication with the urine introduction port 28a and discharges the urine, are disposed in the shaft 22a. The oxygen sensor 20a is disposed in the urethral catheter 18a such that the oxygen sensor main body 50a is in contact with the urine flowing in the urinary passage 74.

Accordingly, the oxygen sensor main body 50a can be in contact with the urine flowing in the urinary passage 74, and thus, it is possible to relatively accurately and reliably measure the oxygen in fresh urine which is discharged from the kidney to the outside of the body through the bladder 140.

The oxygen sensor 20a includes the oxygen sensor main body 50a including the fluorescent body 56, and the substrate 54a coated with the fluorescent body 56, and the optical fiber 58 formed separately from the oxygen sensor main body 50a. The oxygen sensor main body 50a is fixed to the urethral catheter 18a such that at least a part of the fluorescent body 56 is in contact with the urine in the urinary passage 74, and the optical fiber 58 is fixed to the urethral catheter 18a in a state where the distal end surface 58a of the optical fiber 58 is positioned with respect to the fluorescent body 56 such that the fluorescent body 56 can be irradiated with the excitation light, and the fluorescence from the fluorescent body 56 can be received. Accordingly, the oxygen sensor main body 50a including the fluorescent body 56 and the optical fiber 58 can be separately manufactured, and are incorporated in the urethral catheter 18a, and thus, it is possible to measure the oxygen in the urine.

The distal end opening portion 34 of the lumen 30 configuring the urinary passage 74, is formed on the distal end of the shaft 22a. The urethral catheter 18a includes the blocking portion 23a which is fitted into the distal end opening portion 34, and the oxygen sensor main body 50a is fixed to the blocking portion 23a. In this case, the blocking portion 23a to which the oxygen sensor main body 50a is fixed, is fitted into the distal end opening portion 34 from the distal end side of the shaft 22a, and thus, it is possible to rather accurately, easily, and reliably incorporate the oxygen sensor main body 50a with respect to the shaft 22a.

The optical fiber 58 is fixed to the shaft 22a such that the distal end surface 58a of the optical fiber 58 is positioned in the urinary passage 74 and faces the fluorescent body 56. Accordingly, it is possible to efficiently irradiate the fluorescent body 56 with the excitation light from the optical fiber 58, and to efficiently receive the fluorescence from the fluorescent body 56 by the optical fiber 58.

In this embodiment, approximately the entire protruding end surface 38a of the protruding portion 38 is covered with the fluorescent body 56, and thus, it is possible to rather easily position the optical fiber 58 with respect to the fluorescent body 56. In addition, the adhesive agent 66 can be injected from the through hole 68 formed on the outer surface of the shaft 22a at the time of fixing the optical fiber 58, and thus, it is possible to improve the ability to assemble the oxygen measurement device 10, and to help prevent the distal end surface 58a of the optical fiber 58 from being contaminated by the adhesive agent 66.

Figure 12:
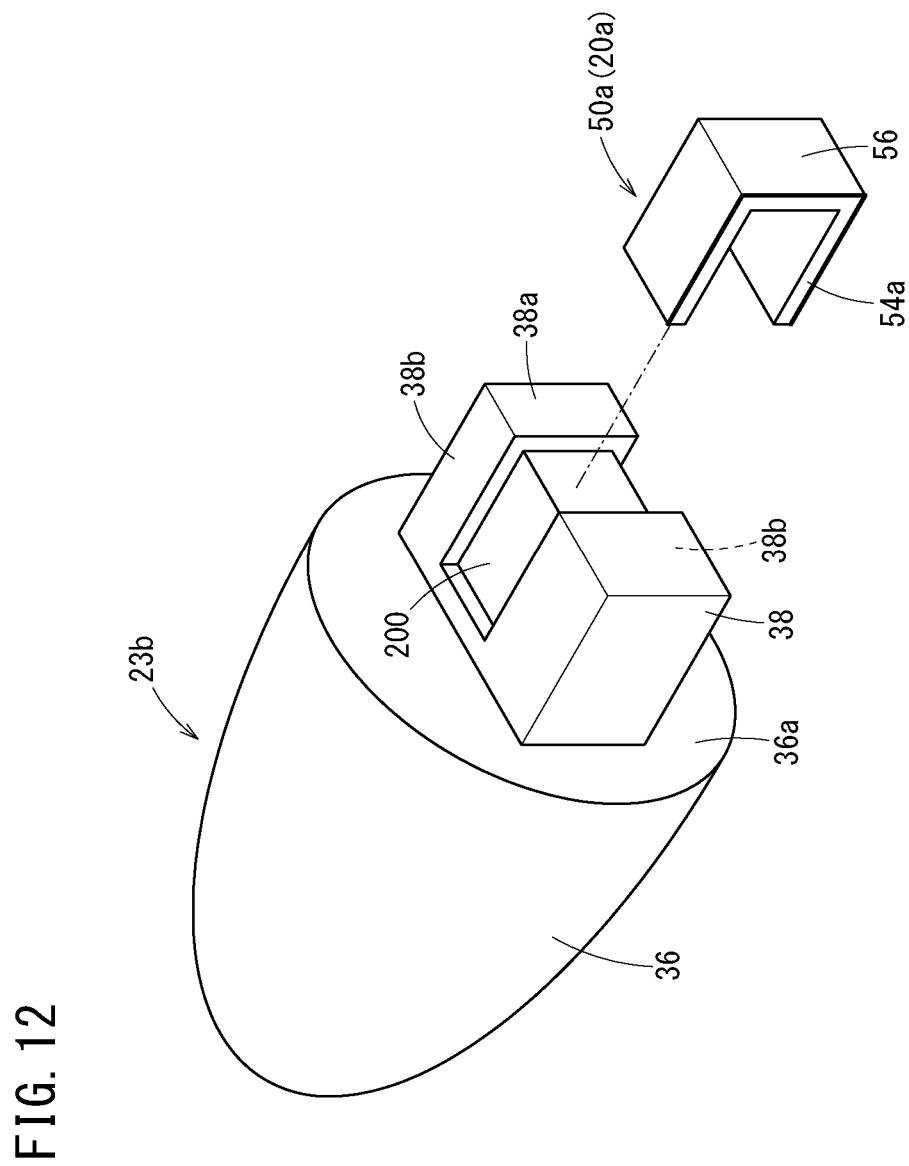
FIG. 12 is a perspective view illustrating another configuration of the blocking portion and the oxygen sensor main body.

As illustrated in FIG. 12, the substrate 54a of the oxygen sensor main body 50a may have a width dimension narrower than the width dimension of the protruding portion 38, and the latch groove 200 into which the substrate 54a bent approximately into a U-shape, is fitted, may be formed in the protruding portion 38 of a blocking portion 23b. The substrate 54a is formed into the shape of a band. The latch groove 200 is positioned in the center of a width direction of the protruding portion 38, and allows each of the side surfaces 38b to extend in a protruding direction of the protruding portion 38, and the protruding end surface 38a to extend over the entire length in the height direction. According to such a configuration, the material of the substrate 54a and the fluorescent body 56 can be reduced, and thus, it is possible to reduce the manufacturing cost of the oxygen sensor main body 50a.

Next, oxygen measurement devices 10B to 10K according to a first modification example to a tenth modification example will be described.

First Modification Example

Next, the oxygen measurement device 10B according to the first modification example will be described. Furthermore, in the oxygen measurement device 10B according to the first modification example, the same reference numerals will be applied to the same constituents as those of the oxygen measurement device 10A described above, and the detailed description of the same reference numerals will be applied to the same constituents as those of the oxygen measurement device 10A described above will be omitted.

Figure 13A:
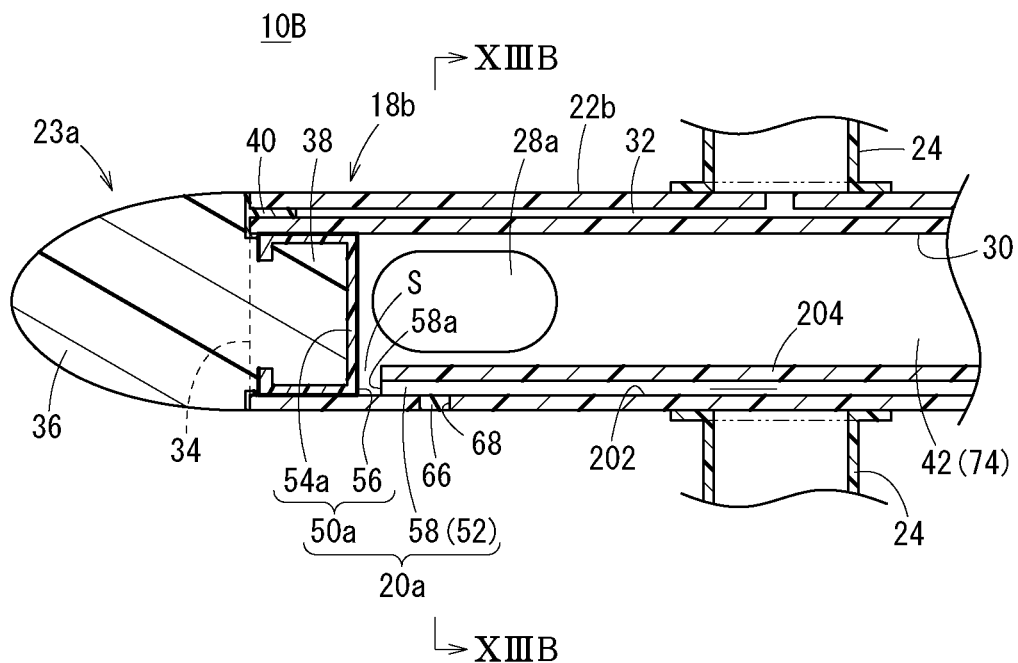
FIG. 13A is a partially omitted longitudinal sectional view of an oxygen measurement device according to a first modification example.
Figure 13B:
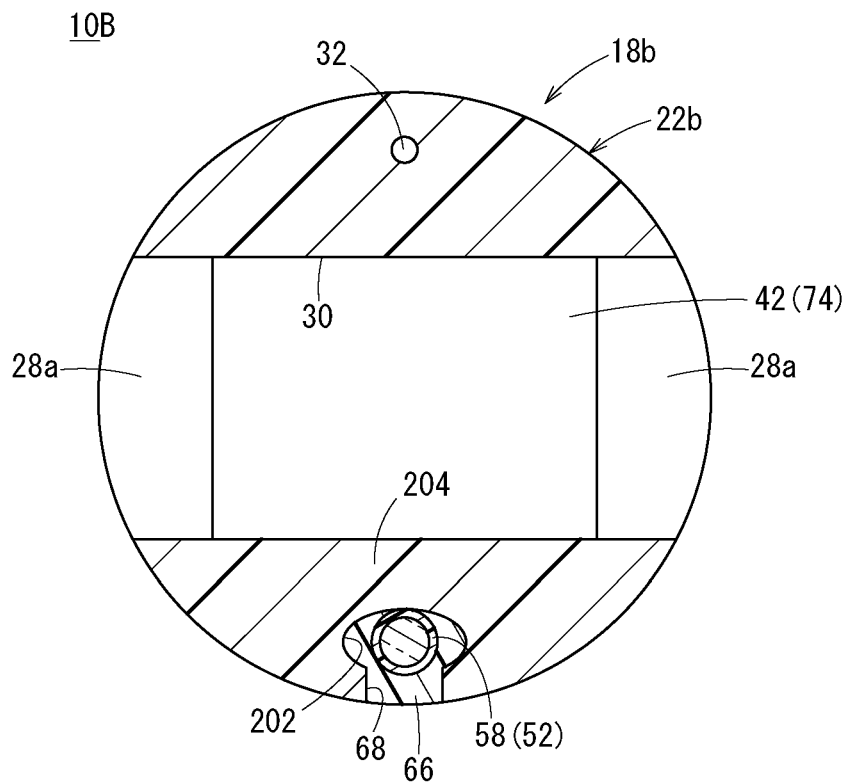
FIG. 13B is a transverse sectional view along line XIIIB-XIIIB of FIG. 13A.

As illustrated in FIG. 13A and FIG. 13B, in the oxygen measurement device 10B according to the first modification example, a urethral catheter 18b is provided. A sensor lumen 202 in which the optical fiber 58 is provided, is formed in a wall portion of a shaft 22b of the urethral catheter 18b. That is, a partition wall 204 is disposed between the urine introduction lumen 42 and the sensor lumen 202. A gap S through which the urine can be discharged, is disposed between a distal end surface of the partition wall 204 and the fluorescent body 56. The optical fiber 58 is fixed to the shaft 22b by the adhesive agent 66 which is filled in the sensor lumen 202 to seal the through hole 68 formed on the outer surface of the distal end portion of the shaft 22b. The through hole 68 is formed in a portion positioned between two urine introduction ports 28a on the outer circumference surface of the shaft 22b.

According to this modification example, the optical fiber 58 is provided in the sensor lumen 202, and thus, it is possible to help prevent the discharge of the urine in the urinary passage 74 from being inhibited by the optical fiber 58. Accordingly, it is possible to rather smoothly discharge the urine in the urinary passage 74.

In this modification example, the same effect is obtained according to the same configuration as that of the oxygen measurement device 10A described above.

Second Modification Example

Next, the oxygen measurement device 100 according to the second modification example will be described. Furthermore, in the oxygen measurement device 100 according to the second modification example, the same reference numerals will be applied to the same constituents as the constituents of the oxygen measurement device 10B according to the first modification example, and the detailed description of the same reference numerals and the same constituents as the constituents of the oxygen measurement device 10B according to the first modification example will be omitted. Furthermore, the same applies to the fourth modification example, the fifth modification example, the ninth modification example, and the tenth modification example described below.

Figure 14A:
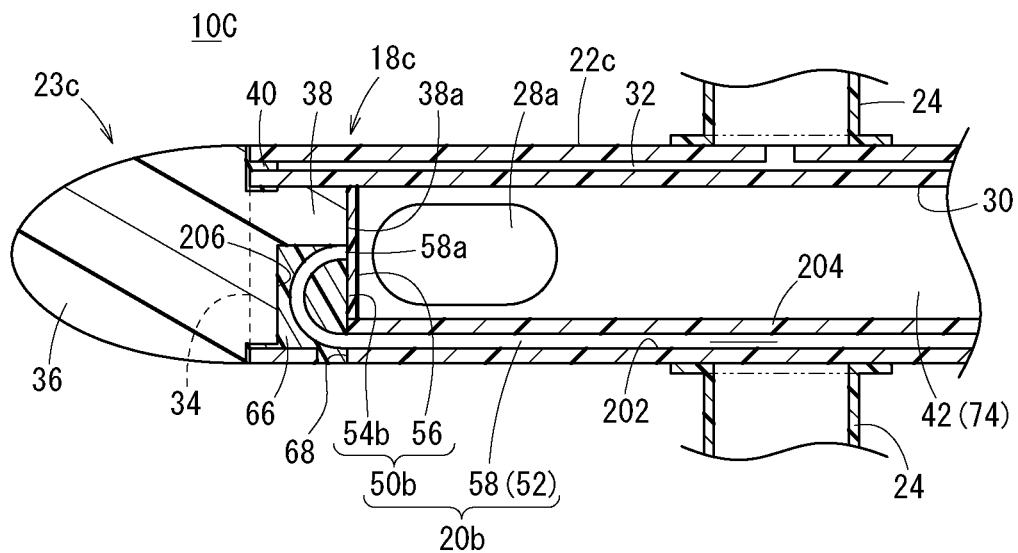
FIG. 14A is a partially omitted longitudinal sectional view of an oxygen measurement device according to a second modification example.
Figure 14B:
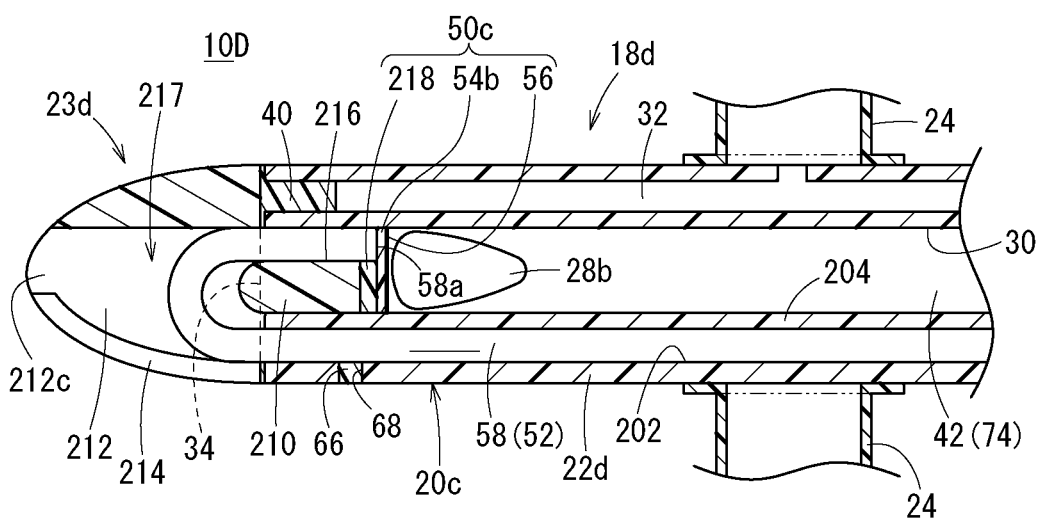
FIG. 14B is a partially omitted longitudinal sectional view of an oxygen measurement device according to a third modification example.
Figure 15A:
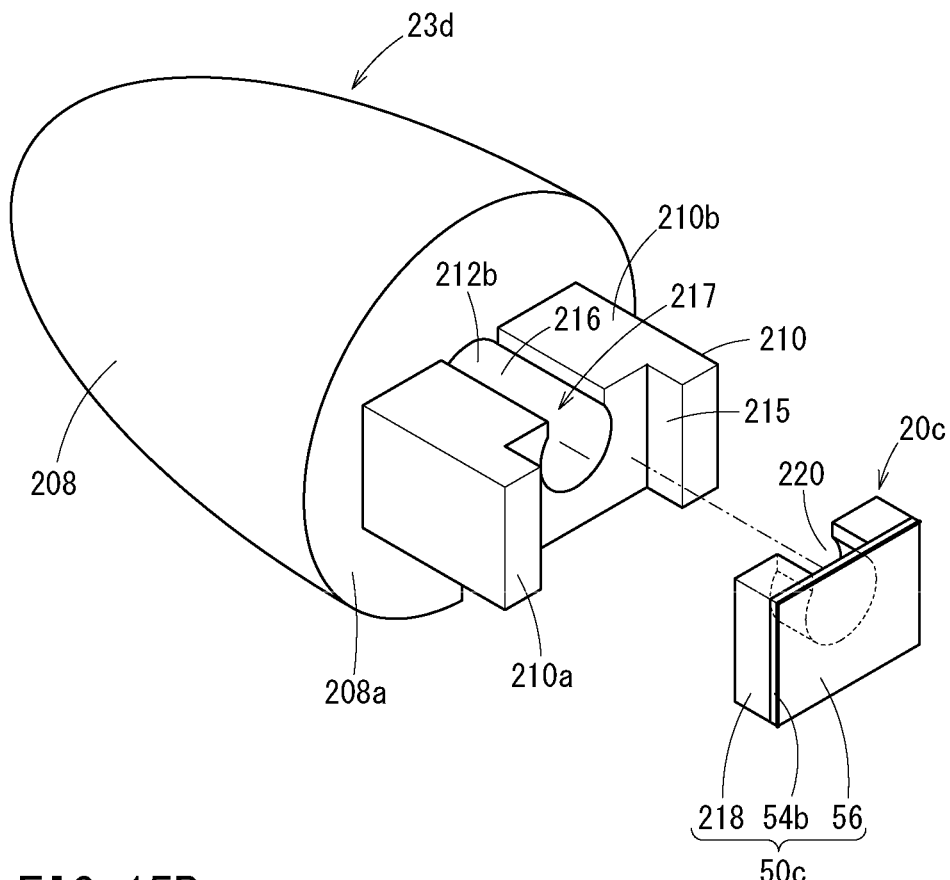
FIG. 15A is a perspective view of a blocking portion and an oxygen sensor main body configuring the oxygen measurement device illustrated in FIG. 14B.
Figure 15B:
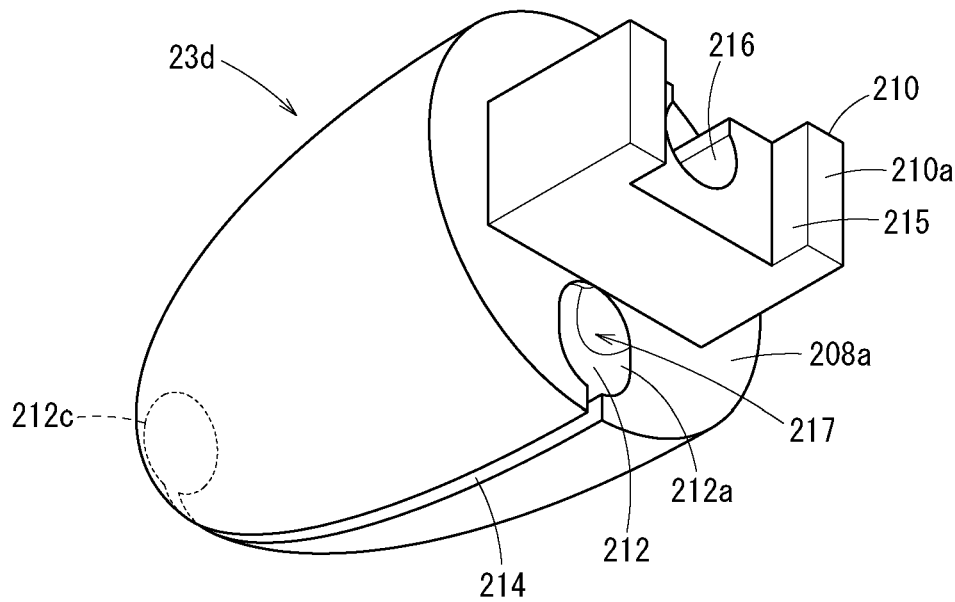
FIG. 15B is a perspective view from another angle of the blocking portion.

As illustrated in FIG. 14A, the oxygen measurement device 100 according to the second modification example includes a urethral catheter 18c and an oxygen sensor 20b. The urethral catheter 18c includes a shaft 22c and a blocking portion 23c. An arrangement hole 206 in which the optical fiber 58 is provided, is formed in the protruding portion 38 of the blocking portion 23c. The partition wall 204 extends to the position of the protruding end surface 38a of the protruding portion 38.

A substrate 54b of an oxygen sensor main body 50b is attached to the protruding end surface 38a of the protruding portion 38 to cover the arrangement hole 206 from the proximal end side, and to allow the fluorescent body 56 to be in contact with the urine in the urinary passage 74. The substrate 54b is configured to be capable of transmitting the excitation light from the optical fiber 58 and the fluorescence from the fluorescent body 56. The fluorescent body 56 is positioned on the distal end side from the urine introduction port 28a.

The optical fiber 58 is fixed to the urethral catheter 18c in a state of being turned back to the proximal end side at 180° on the distal end side from the urinary passage 74 such that the distal end surface 58a of the optical fiber 58 is positioned on a side opposite from the urinary passage 74 sandwiching the oxygen sensor main body 50b. That is, a turned-back portion of the optical fiber 58 is disposed in the arrangement hole 206 of the protruding portion 38. The optical fiber 58 is fixed to the shaft 22c and the blocking portion 23c by injecting the adhesive agent 66 into the arrangement hole 206 from the outside of the shaft 22c through the through hole 68 which is formed on the outer surface of the shaft 22c. The distal end surface 58a of the optical fiber 58 is in contact with a rear surface of the substrate 54b on a side opposite to a surface coated with the fluorescent body 56. Here, the distal end surface 58a of the optical fiber 58 may be close to the rear surface of the substrate 54b.

Next, the assembly of the oxygen sensor 20b with respect to the urethral catheter 18c will be described. Furthermore, in an initial state, the substrate 54b coated with the fluorescent body 56, is fixed to the protruding end surface 38a of the protruding portion 38 by an adhesive agent (not illustrated) or the like. In this modification example, in a state where the optical fiber 58 is inserted into the sensor lumen 202, a distal end of the optical fiber 58 is drawn out in the distal end direction from the distal end opening portion 34 of the shaft 22c. Then, the distal end portion of the optical fiber 58 is disposed in the arrangement hole 206 of the protruding portion 38 in a state of being turned back at 180°. At this time, the distal end surface 58a of the optical fiber 58 is in contact with or close to the rear surface of the substrate 54b. Subsequently, the distal end surface 58a of the shaft 22c, and a wall surface configuring the distal end opening portion 34 are coated with the adhesive agent 40, and thus, the protruding portion 38 is fitted into the distal end opening portion 34. At this time, a portion of the optical fiber 58, which is drawn out in the distal end direction, is pushed by the blocking portion 23c, and is pushed back in the proximal end direction. After that, the adhesive agent 66 is injected into the arrangement hole 206 from the outside of the shaft 22c through the through hole 68, and thus, the optical fiber 58 is fixed to the shaft 22c and the blocking portion 23c. Accordingly, it is possible to rather accurately position the fluorescent body 56 and the distal end surface 58a of the optical fiber 58.

According to this modification example, the optical fiber 58 is fixed to the urethral catheter 18c in the state of being turned back on the distal end side from the urinary passage 74 such that the distal end surface 58a of the optical fiber 58 is positioned on the side opposite to the urinary passage 74 sandwiching the oxygen sensor main body 50b. The base portion is configured to be capable of transmitting the excitation light from the optical fiber 58 and the fluorescence from the fluorescent body 56. For this reason, it is possible to improve the ability to assemble and the accuracy of the oxygen measurement device, and to measure the oxygen in the urine while preventing the distal end surface 58a of the optical fiber 58 from being contaminated due to the contact with the urine.

In addition, the distal end surface 58a of the optical fiber 58 is in contact with the surface of the substrate 54b (the base portion) on a side opposite to the surface coated with the fluorescent body 56. Accordingly, it is possible to reliably bring the fluorescent body 56 into contact with the urine, to efficiently irradiate the fluorescent body 56 with the excitation light from the optical fiber 58, and to efficiently receive the fluorescence from the fluorescent body 56 by the optical fiber 58.

Further, the arrangement hole 206 in which the turned-back portion of the optical fiber 58 is provided, is formed in the blocking portion 23c. Accordingly, it is possible to dispose the optical fiber 58 in a state of being rather easily turned back on the distal end side of the urinary passage 74.

In this modification example, the same effect is obtained according to the same configuration as that of the oxygen measurement devices 10A and 10B described above.

Third Modification Example

Next, the oxygen measurement device 10D according to the third modification example will be described. Furthermore, in the oxygen measurement device 10D according to the third modification example, the same reference numerals will be applied to the same constituents as those of the oxygen measurement device 10C according to the second modification example, and the detailed description of the same reference numerals and the same constituents as those of the oxygen measurement device 10C according to the second modification example will be omitted.

As illustrated in FIG. 14B to FIG. 15B, the oxygen measurement device 10D according to the third modification example includes a urethral catheter 18d and an oxygen sensor 20c. The urethral catheter 18d includes a shaft 22d and a blocking portion 23d. The blocking portion 23d includes a distal end bulging portion 208 and a protruding portion 210. A first hole portion 212 in which the optical fiber 58 can be provided, and a slit 214 which is in communication with the first hole portion 212 and is opened on an outer surface of the distal end bulging portion 208, are formed in the distal end bulging portion 208. The first hole portion 212 includes a first opening portion 212a and a second opening portion 212b which are opened on a proximal end surface 208a of the distal end bulging portion 208, and a third opening portion 212c which is opened on the most-distal end of the distal end bulging portion 208. The first opening portion 212a is in communication with the sensor lumen 202. The second opening portion 212b is positioned approximately in the center of the proximal end surface. The slit 214 extends from the first opening portion 212a to the third opening portion 212c, along the shaft line (i.e., axial) direction.

A rectangular concave portion 215 in which an oxygen sensor main body 50c can be provided, is disposed on a protruding end surface 210a of the protruding portion 210. A second hole portion 216 in communication with the second opening portion 212b, is formed on a side surface 210b of the protruding portion 210. The second hole portion 216 linearly extends from the second opening portion 212b to the bottom of the concave portion 215. The first hole portion 212 and the second hole portion 216 communicate with each other and function as an arrangement hole 217 in which the optical fiber 58 is disposed.

The oxygen sensor main body 50c includes a support portion 218 fixed to the blocking portion 23d. The substrate 54b is fixed to the support portion 218. The support portion 218 is formed into the shape of a rectangular plate, and is fixed to the protruding portion 210 in a state of being provided in the concave portion 215. A positioning hole 220 (a positioning portion) positioning the distal end of the optical fiber 58, is disposed in the support portion 218. The fluorescent body 56 is positioned on the distal end side from the urine introduction port 28b.

The optical fiber 58 is held in the blocking portion 23d in a state of being disposed in the arrangement hole 217. That is, the optical fiber 58 is held in the blocking portion 23d in a state of being disposed in the first opening portion 212a, the first hole portion 212, the second opening portion 212b, and the second hole portion 216. The optical fiber 58 is turned back on the proximal end side at 180° in the first hole portion 212 on the distal end side from the urinary passage 74. In this modification example, the slit 214 and the third opening portion 212c are formed in the blocking portion 23d, and thus, it is possible to rather easily bend the blocking portion 23d when the optical fiber 58 is turned back in the first hole portion 212. The distal end surface 58a of the optical fiber 58 is in contact with the rear surface of the substrate 54b. Here, the distal end surface 58a of the optical fiber 58 may be close to the substrate 54b.

The urine introduction port 28b is formed such that an opening width along a circumferential direction increases towards the distal end direction of the shaft 22d.

Next, the assembly of the oxygen sensor 20c with respect to the urethral catheter 18d will be described. Furthermore, in an initial state, the substrate 54b coated with the fluorescent body 56 is fixed to the support portion 218, and the support portion 218 is fixed (i.e., attached) into the concave portion 215 of the protruding portion 210 by an adhesive agent (not illustrated) or the like. In this modification example, in a state where the optical fiber 58 is inserted into the sensor lumen 202, the distal end of the optical fiber 58 is drawn out in the distal end direction from the distal end opening portion 34 of the shaft 22d.

Then, the blocking portion 23d is held such that the third opening portion 212c is directed towards the distal end of the optical fiber 58, the distal end of the optical fiber 58 is inserted into the blocking portion 23d from the third opening portion 212c to reach the second hole portion 216 through the second opening portion 212b, the distal end of the optical fiber 58 is fitted into the positioning hole 220 such that the distal end surface 58a is disposed to be in contact with or in the vicinity of the rear surface of the substrate 54b, and a wall surface configuring the second hole portion 216 and the optical fiber 58 are coated with an adhesive agent (not illustrated) and are fixed together. After that, the blocking portion 23d is held, the optical fiber 58 is reversed by 180° while confirming that the optical fiber 58 is disposed in the arrangement hole 217 while expanding the slit 214, the optical fiber 58 is disposed in the first opening portion 212a through the first hole portion 212, and the proximal end surface 208a of the blocking portion 23d faces the distal end surface 58a of the shaft 22d.

After that, the distal end surface 58a of the shaft 22d and the wall surface configuring the distal end opening portion 34 are coated with the adhesive agent 40, and thus, the protruding portion 210 is fitted into the distal end opening portion 34. Accordingly, the blocking portion 23d is fixed to the shaft 22d, and thus, the oxygen sensor main body 50c which is fixed to the blocking portion 23d, is fixed to the shaft 22d. At this time, a portion of the optical fiber 58, which is drawn out in the distal end direction, is pushed by the shaft 22d, is pushed back in the distal end direction, and is contained in the arrangement hole 217. Then, the adhesive agent 66 is injected into the sensor lumen 202 from the outside of the shaft 22d through the through hole 68, and thus, the optical fiber 58 is fixed to the shaft 22d. In addition, an adhesive agent (not illustrated) is injected into the arrangement hole 217 from the third opening portion 212c until the third opening portion 212c and the slit 214 are filled with the adhesive agent, and the optical fiber 58 is fixed to the blocking portion 23d. Accordingly, it is possible to improve the ability to assemble, and to accurately position the fluorescent body 56 and the distal end surface 58a of the optical fiber 58.

The distal end of the optical fiber 58 is fitted into the positioning hole 220 of the support portion 218 from the third opening portion 212c through the first hole portion 212, the second opening portion 212b, and the second hole portion 216, in a state where the optical fiber 58 is turned back at 180°, as another assembling method. Subsequently, a portion of the optical fiber 58 on the outside of the distal end bulging portion 208 is pushed towards the slit 214 in a state of being along the slit 214. Then, the width of the slit 214 increases, and the optical fiber 58 is disposed in the first hole portion 212 and the first opening portion 212a.

After that, the distal end surface 58a of the shaft 22d and the wall surface configuring the distal end opening portion 34 are coated with the adhesive agent 40, and the protruding portion 210 is fitted into the distal end opening portion 34. Accordingly, the blocking portion 23d is fixed to the shaft 22d, and thus, the oxygen sensor main body 50c which is fixed to the blocking portion 23d, is fixed to the shaft 22d. At this time, a portion of the optical fiber 58, which extends (i.e., is drawn out) in the distal end direction, is pushed by the blocking portion 23d, and is pushed back in the proximal end direction. Then, the adhesive agent 66 is injected into the sensor lumen 202 from the outside of the shaft 22d through the through hole 68, and thus, the optical fiber 58 is fixed to the shaft 22d. In addition, an adhesive agent (not illustrated) is injected into the arrangement hole 217 from the third opening portion 212c until the third opening portion 212c and the slit 214 are filled with the adhesive agent, and the optical fiber 58 is fixed to the blocking portion 23d. Accordingly, it is possible to accurately position the fluorescent body 56 and the distal end surface 58a of the optical fiber 58.

According to this modification example, the optical fiber 58 is held in the blocking portion 23d in a state of being disposed in the arrangement hole 217. Accordingly, when the blocking portion 23d is fitted into the distal end opening portion 34 of the shaft 22d, it is possible to accurately assemble the optical fiber 58 with respect to the shaft 22d.

In this modification example, the oxygen sensor main body 50c includes the support portion 218 fixed to the blocking portion 23d. The substrate 54b is fixed to the support portion 218. The positioning hole 220 positioning the distal end of the optical fiber 58 is disposed in the support portion 218. For this reason, it is possible to accurately hold a positional relationship between the distal end surface 58a of the optical fiber 58 and the fluorescent body 56. In addition, it is possible to fix the oxygen sensor main body 50c to the blocking portion 23d by gripping the support portion 218.

Further, the fluorescent body 56 is positioned on the distal end side from the urine introduction port 28b, and the urine introduction port 28b is formed such that the opening width along the circumferential direction increases towards the distal end direction of the shaft 22d. Accordingly, it is possible to efficiently guide the urine introduced into the urinary passage 74 from the urine introduction port 28b, to the fluorescent body 56 which is positioned on the distal end side from the urine introduction port 28b.

In this modification example, the same effect is obtained according to the same configuration as that of the oxygen measurement devices 10A to 10C described above. The urine introduction port 28b of this modification example may be disposed in the oxygen measurement devices 10A to 10C described above.

Fourth Modification Example

Figure 16A:
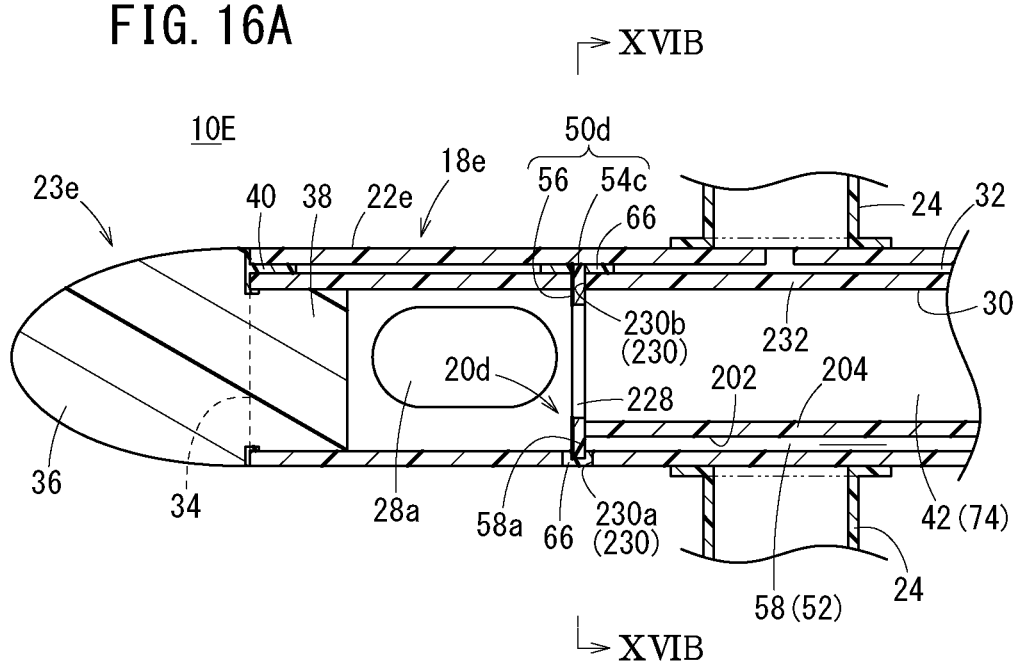
FIG. 16A is a partially omitted longitudinal sectional view of an oxygen measurement device according to a fourth modification example.
Figure 16B:
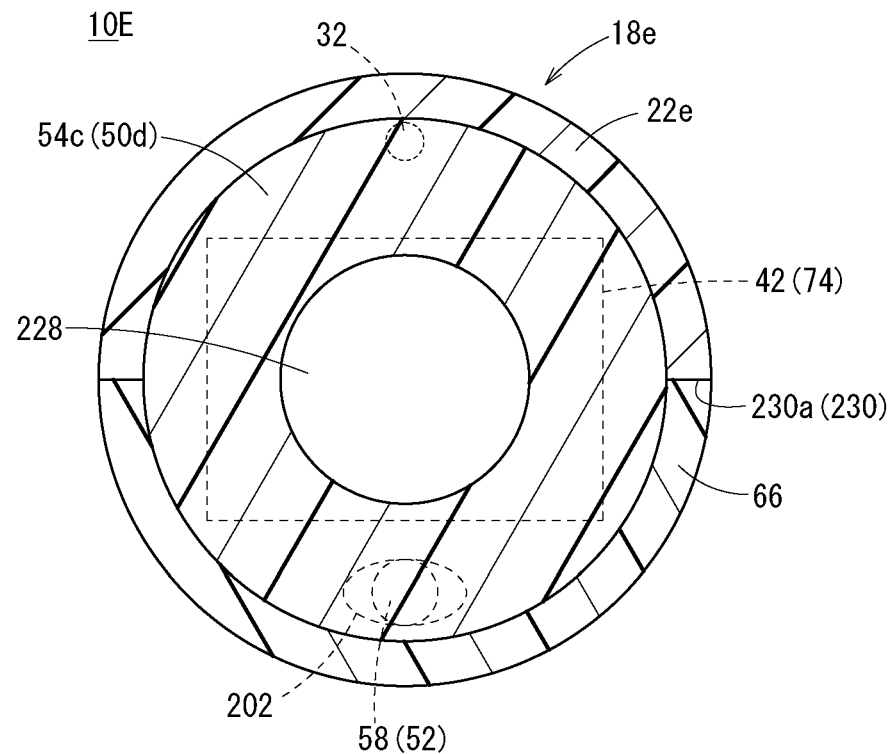
FIG. 16B is a transverse sectional view along line XVIB-XVIB of FIG. 16A.

Next, the oxygen measurement device 10E according to the fourth modification example will be described. As illustrated in FIG. 16A and FIG. 16B, the oxygen measurement device 10E according to the fourth modification example includes a urethral catheter 18e and an oxygen sensor 20d. The urethral catheter 18e includes a shaft 22e and a blocking portion 23e.

An oxygen sensor main body 50d of the oxygen sensor 20d is fixed (i.e., attached) to the shaft 22e such that the fluorescent body 56 is positioned on the proximal end side from the urine introduction port 28a in the urine introduction lumen 42 (the urinary passage 74). A substrate 54c (a base portion) of the oxygen sensor main body 50d is configured to be capable of transmitting the light from the optical fiber 58 and the fluorescence from the fluorescent body 56. The substrate 54c is configured into the shape of a circular ring, and extends in a direction orthogonal to a shaft line of the shaft 22e such that the fluorescent body 56 is positioned on the distal end side from the substrate 54c. That is, the substrate 54c includes an inner hole 228 through which the urine is discharged. Here, the substrate 54c may be formed into the shape of a rectangular ring, insofar as being in the shape of a ring.

A holding hole 230 into which an outer edge portion of the substrate 54c is inserted, is formed on the wall surface configuring the urine introduction lumen 42. The holding hole 230 is opened on an outer surface of the shaft 22e, and includes a first slit 230a having a size through which the oxygen sensor main body 50d can be inserted into the urinary passage 74 from the outside of the shaft 22e, and a second slit 230b formed in a wall portion 232 between the dilation lumen 32 and the urine introduction lumen 42. The first slit 230a extends in a circumferential direction of the shaft 22e, for example, at approximately 180°. The second slit 230b extends up to the dilation lumen 32. That is, a part of the outer edge portion of the substrate 54c is positioned in the dilation lumen 32. Furthermore, the substrate 54c is positioned on the distal end side from the balloon 24. In addition, the distal end surface 58a of the partition wall 204 is in contact with a rear surface of the substrate 54c on a side opposite to a surface in which the fluorescent body 56 is positioned.

The substrate 54c is fixed to the shaft 22e by the adhesive agent 66 which is injected into the first slit 230a and the second slit 230b. The adhesive agent 66 seals a part of the dilation lumen 32, the first slit 230a, and the second slit 230b, and flows into the sensor lumen 202, and thus, the optical fiber 58 is fixed (i.e. attached) to the shaft 22e.

The optical fiber 58 is disposed on the proximal end side from the base portion such that the distal end surface 58a of the optical fiber 58 faces the rear surface of the substrate 54c. The distal end surface 58a of the optical fiber 58 is in contact with the rear surface of the substrate 54c. Here, the distal end surface 58a of the optical fiber 58 may be close to the rear surface of the substrate 54c.

Next, the assembly of the oxygen sensor 20d with respect to the urethral catheter 18e will be described. In this modification example, the optical fiber 58 is inserted into the sensor lumen 202. After that, the oxygen sensor main body 50d is pushed to the first slit 230a from the outside of the shaft 22e, in a state where the outer edge portion of the substrate 54c is coated with the adhesive agent 66. Then, the oxygen sensor main body 50d is inserted into the second slit 230b, and thus, the oxygen sensor main body 50d is held in the holding hole 230. Then, the adhesive agent 66 is injected into the first slit 230a as a through hole, from the outside of the shaft 22e, and thus, the oxygen sensor main body 50d and the optical fiber 58 are fixed to the shaft 22e. Accordingly, it is possible to accurately position the fluorescent body 56 and the distal end surface 58a of the optical fiber 58.

According to this modification example, the fluorescent body 56 is positioned on the proximal end side from the urine introduction port 28a in the urinary passage 74. Accordingly, it is possible to efficiently bring the urine discharged through the urine introduction lumen 42 into contact with the fluorescent body 56.

In this modification example, the substrate 54c is configured to be capable of transmitting the excitation light from the optical fiber 58 and the fluorescence from the fluorescent body 56, and extends in the direction orthogonal to the shaft line of the shaft 22e such that the fluorescent body 56 is positioned on the distal end side from the substrate 54c. The optical fiber 58 is disposed on the proximal end side from the base portion such that the distal end surface 58a of the optical fiber 58 faces the rear surface of the base portion on the side opposite from the surface coated with the fluorescent body 56. Accordingly, it is possible to efficiently bring the urine in the urinary passage 74 into contact with the fluorescent body 56. In addition, it is possible to efficiently irradiate the fluorescent body 56 with the excitation light from the optical fiber 58, and to efficiently receive the fluorescence from the fluorescent body 56 by the optical fiber 58.

Further, the substrate 54c is configured into the shape of a ring. For this reason, it is possible to rather smoothly discharge the urine in the urine introduction lumen in a proximal end direction of the shaft 22e through the inner hole of the substrate 54c.

According to this modification example, the holding hole 230 into which the outer edge portion of the base portion is inserted, is formed on the wall surface configuring the urine introduction lumen 42. Accordingly, it is possible to hold the substrate 54c in a state where the substrate 54c extends in the direction orthogonal to the shaft line of the shaft 22e, by a rather simple configuration.

In addition, the holding hole 230 is opened on the outer surface of the shaft 22e, and includes the first slit 230a having a size through which the oxygen sensor main body 50d can be inserted into the urinary passage 74 from the outside of the shaft 22e, and the oxygen sensor main body 50d is fixed to the shaft 22e by the adhesive agent 66 filled to seal the first slit 230a. In this case, it is possible to rather simply and accurately assemble the oxygen sensor main body 50d from the outside of the shaft 22e.

In this modification example, the same effect is obtained according to the same configuration as that of the oxygen measurement devices 10A to 10D described above.

Fifth Modification Example

Figure 17A:
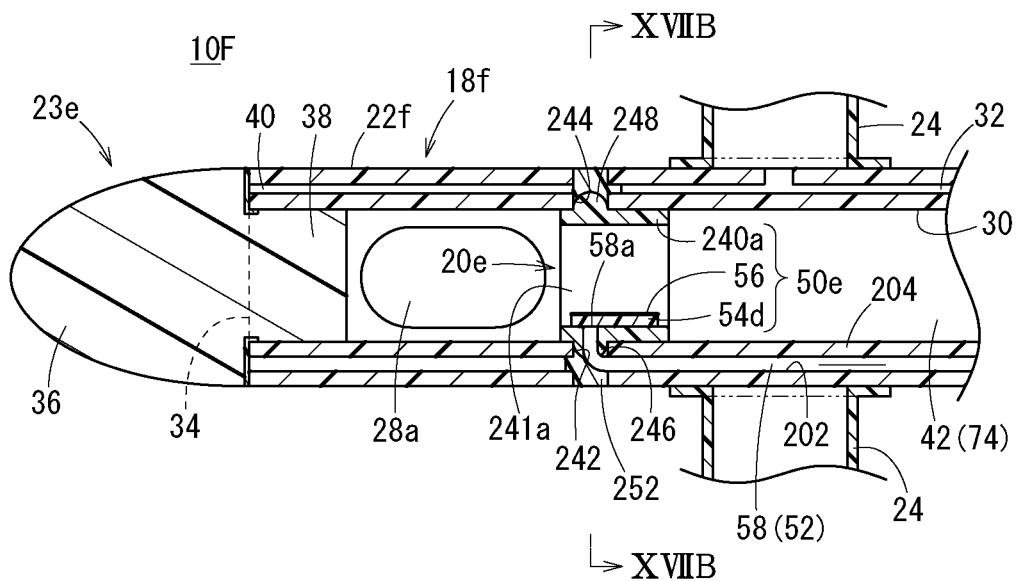
FIG. 17A is a partially omitted longitudinal sectional view of an oxygen measurement device according to a fifth modification example.
Figure 17B:
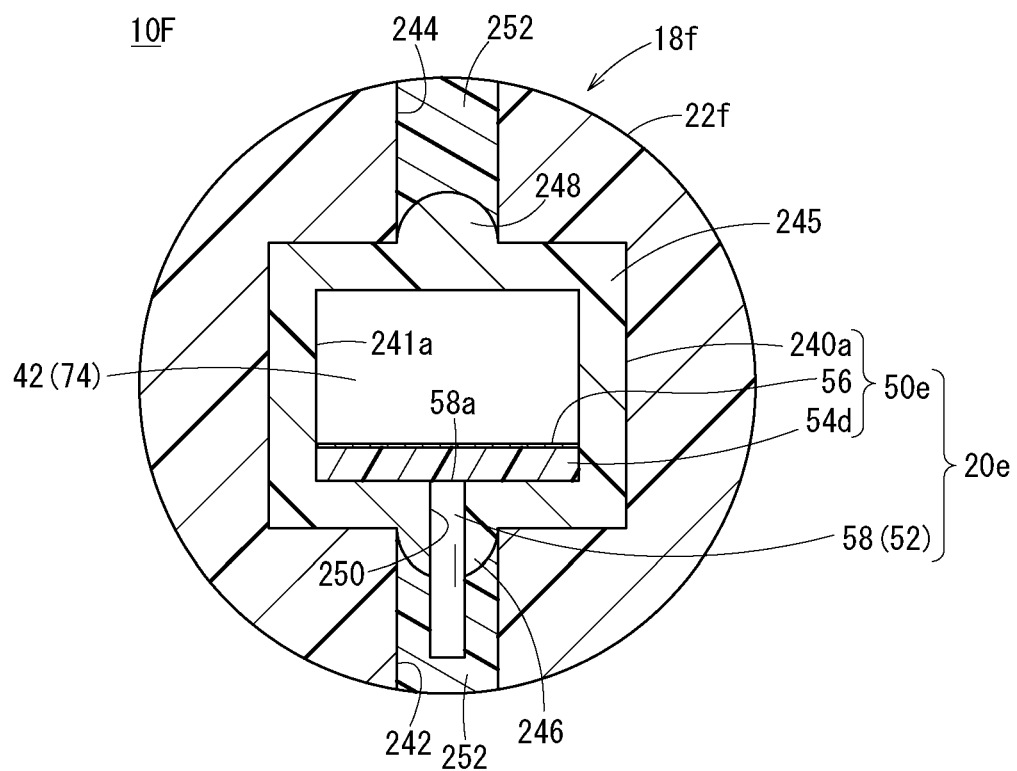
FIG. 17B is a transverse sectional view along line XVIIB-XVIIB of FIG. 17A.

Next, the oxygen measurement device 10F according to the fifth modification example will be described. As illustrated in FIG. 17A and FIG. 17B, the oxygen measurement device 10F according to the fifth modification example includes a urethral catheter 18f and an oxygen sensor 20e. The urethral catheter 18f includes a shaft 22f and the blocking portion 23e.

An oxygen sensor main body 50e of the oxygen sensor 20e is fixed to the shaft 22f such that the fluorescent body 56 is positioned on the proximal end side from the urine introduction port 28a in the urine introduction lumen 42 (the urinary passage 74). A substrate 54d (a base portion) of the oxygen sensor main body 50e is made of glass, polyethylene, or the like, which is capable of transmitting the excitation light from the optical fiber 58 and the fluorescence from the fluorescent body 56. The substrate 54d is configured into the shape of a flat plate. The oxygen sensor main body 50e includes a support portion 240a which is fixed to the shaft 22f. The substrate 54d is fixed to the support portion 240a. The support portion 240a can be fabricated from the same material as that of the shaft 22f, or glass, a resin material, or the like, into the shape of a rectangular ring, and has a shape according to the sectional shape of the urine introduction lumen 42. That is, an outer surface of the support portion 240a is in contact with the wall surface configuring the urine introduction lumen 42. The support portion 240a is disposed on the proximal end side from the urine introduction port 28a in the urine introduction lumen 42. The substrate 54d is fixed (i.e., attached) to a wall surface configuring an inner hole 241a of the support portion 240a in a state where the substrate 54d extends in a shaft line direction of the shaft 22f. That is, the fluorescent body 56 is positioned in the inner hole 241a of the support portion 240a.

The support portion 240a includes two convex portions 246 and 248 (a second engagement portion) which are positioned in the shaft 22f by being fitted into two support holes 242 and 244 (a first engagement portion) as a through hole disposed on the wall surface configuring the urine introduction lumen 42. Two support holes 242 and 244 are positioned on opposite sides by sandwiching the support portion 240a between the two support holes 242 and 244. The support hole 242 is a through hole which extends up to an outer surface of the shaft 22f to traverse the sensor lumen 202. The support hole 244 is a through hole which extends up to the outer surface of the shaft 22f to traverse the dilation lumen 32.

The convex portions 246 and 248 are semispherical protrusions protruding to the outside from the outer surface of the support portion main body 245. A positioning hole 250 (a positioning portion) into which the distal end of the optical fiber 58 is fitted, is disposed in the support portion main body 245 and the convex portion 246. The positioning hole 250 is opened on a surface to which the substrate 54d is fixed, in the wall surface configuring the inner hole 241a of the support portion 240a.

The optical fiber 58 is provided in the sensor lumen 202, the support hole 242, and the positioning hole 250. The distal end surface 58a of the optical fiber 58 is in contact with a rear surface of the substrate 54d. Here, the distal end surface 58a of the optical fiber 58 may be close to the rear surface of the substrate 54d. The support portion 240a and the optical fiber 58 are fixed (i.e., attached) to the shaft 22f by an adhesive agent 252 filled to seal the support holes 242 and 244.

Next, the assembly of the oxygen sensor 20e with respect to the urethral catheter 18f will be described. Furthermore, in an initial state, the substrate 54d coated with the fluorescent body 56, is fixed to the support portion 240a by an adhesive agent (not illustrated) or the like. In this modification example, in a state where the optical fiber 58 is inserted into the sensor lumen 202, the distal end of the optical fiber 58 is drawn out in the distal end direction from the distal end opening portion 34 of the shaft 22f. In such a state, the optical fiber 58 is inserted into the support hole 242. Then, in a state where the distal end of the optical fiber 58 is fitted into the positioning hole 250 of the support portion 240a, the support portion 240a is inserted from the distal end opening portion 34 of the shaft 22f, and the convex portion 246 is fitted into the support hole 242, and the convex portion 248 is fitted into the support hole 244. At this time, a portion of the optical fiber 58, which is drawn out (i.e., extend outward) in the distal end direction, is pushed by the support portion 240a, and is pushed back in the proximal end direction. Then, the adhesive agent 252 is injected into each of the support holes 242 and 244 from the outside of the shaft 22f, and thus, the support portion 240a and the optical fiber 58 are fixed to the shaft 22f. Accordingly, it is possible to accurately position the fluorescent body 56 and the distal end surface 58a of the optical fiber 58. After that, the protruding portion 38 of the blocking portion 23e is fitted into the distal end opening portion 34 of the shaft 22f.

Furthermore, the optical fiber 58 may be in a state of being drawn out (i.e., extending) from the support hole 242 through the sensor lumen 202, the support portion 240a may be inserted from the distal end opening portion 34 of the shaft 22f, the convex portion 246 may be fitted into the support hole 242, and the convex portion 248 may be fitted into the support hole 244, and then, the distal end of the optical fiber 58 is fitted into the positioning hole 250 of the support portion 240a, and the portion of the optical fiber 58, which is drawn out from the support hole 242, may be pushed back in the proximal end direction, as another assembling method.

According to this modification example, the oxygen sensor main body 50e includes the support portion 240a which is fixed to the shaft 22f. The substrate 54d is fixed to the support portion 240a, and the positioning hole 250 positioning the distal end of the optical fiber 58, is disposed in the support portion 240a. Accordingly, it is possible to accurately hold a positional relationship between the distal end surface 58a of the optical fiber 58 and the fluorescent body 56. In addition, it is possible to incorporate the oxygen sensor main body 50e in the urinary passage 74 by gripping the support portion 240a.

In this modification example, the support holes 242 and 244 are disposed on the wall surface configuring the urinary passage 74, and the convex portions 246 and 248 to be positioned in the shaft 22f by being fitted into (engaged with) the support holes 242 and 244, are disposed in the support portion 240a. Accordingly, it is possible to accurately incorporate the oxygen sensor main body 50e in the urinary passage 74.

In addition, the support portion 240a is configured into the shape of a ring, and the fluorescent body 56 is positioned in the inner hole 241a of the support portion 240a. For this reason, the urine in the urinary passage 74 can be brought into contact with the fluorescent body 56 while discharging the urine in the inner hole 241a of the support portion 240a.

Further, the substrate 54d extends along the shaft line direction of the shaft 22f. Accordingly, it is possible to prevent the discharge of the urine in the inner hole 241a of the support portion 240a from being inhibited by the substrate 54d, compared to a case where the substrate 54d extends along a direction orthogonal to a shaft line of the shaft 22f.

In this modification example, the same effect is obtained according to the same configuration as that of the oxygen measurement devices 10A to 10E described above.

In this modification example, the first engagement portion is a convex portion which is formed on the wall surface configuring the urine introduction lumen 42, and the second engagement portion is a hole portion formed in the support portion 240a, into which the convex portion is fitted.

Sixth Modification Example

Next, the oxygen measurement device 10G according to the sixth modification example will be described. Furthermore, in the oxygen measurement device 10G according to the sixth modification example, the same reference numerals will be applied to the same constituents as those of the oxygen measurement device 10F according to the fifth modification example, and the detailed description of the same reference numerals and the same constituents as those of the oxygen measurement device 10F according to the fifth modification example will be omitted. The same applies to the seventh modification example and the eighth modification example described below.

Figure 18A:
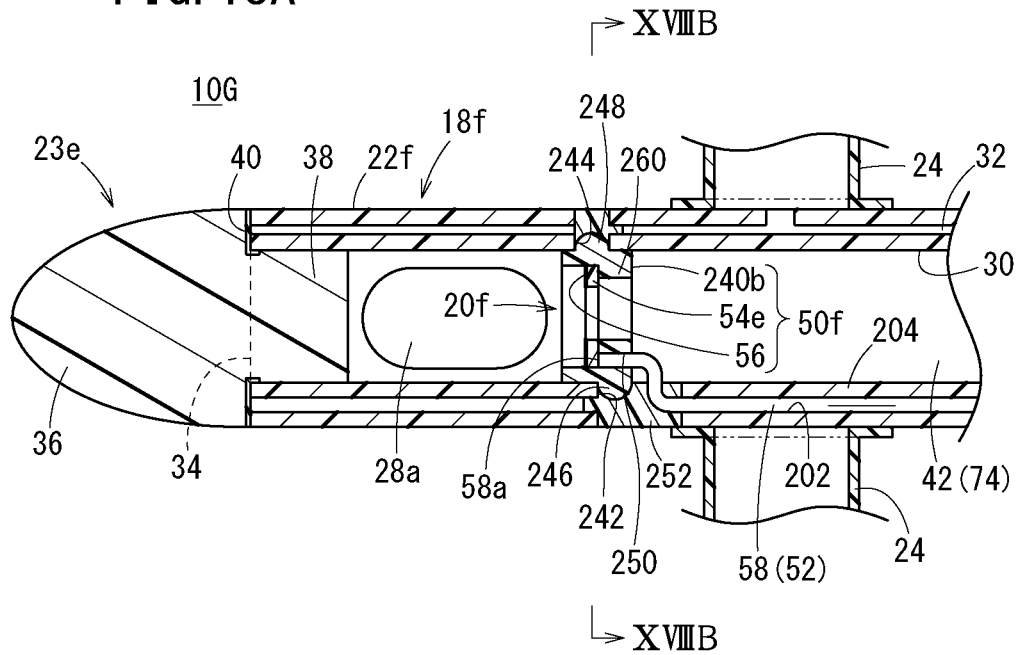
FIG. 18A is a partially omitted longitudinal sectional view of an oxygen measurement device according to a sixth modification example.
Figure 18B:
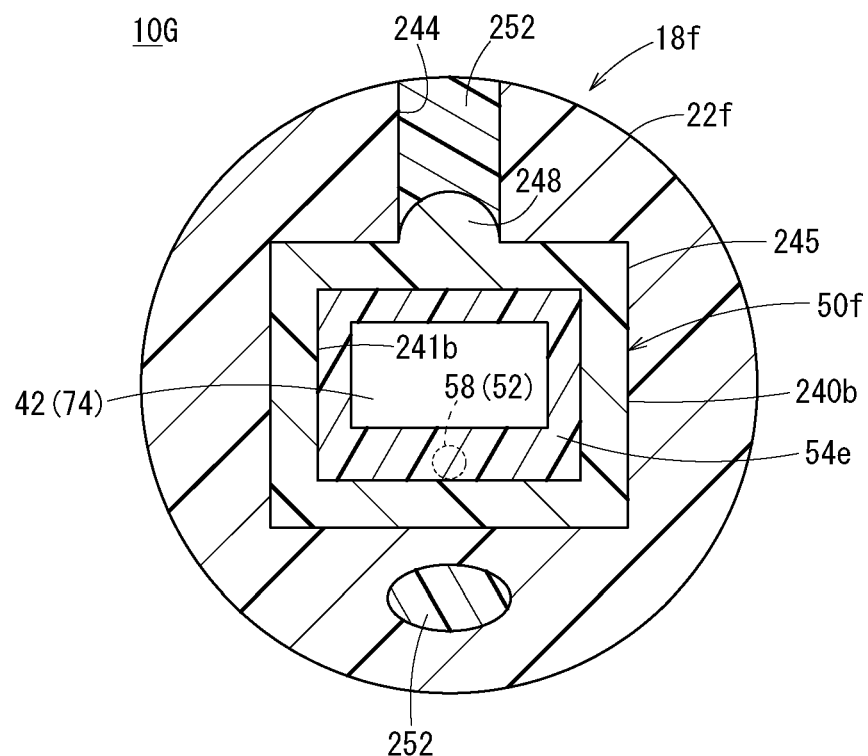
FIG. 18B is a transverse sectional view along line XVIIIB-XVIIIB of FIG. 18A.

As illustrated in FIG. 18A and FIG. 18B, the oxygen measurement device 10G according to the sixth modification example includes an oxygen sensor 20f. A substrate 54e (a base portion) of an oxygen sensor main body 50f configuring the oxygen sensor 20f, is configured into the shape of a rectangular ring, extends in a direction orthogonal to the shaft line direction of the shaft 22f, and is disposed in an inner hole 241b of a support portion 240b such that the fluorescent body 56 is positioned on the distal end side. A support protrusion 260 which inwardly protrudes and supports a rear surface of the substrate 54e, is disposed on a wall surface of the inner hole 241b of the support portion 240b. The positioning hole 250 in which the distal end of the optical fiber 58 is fitted into a rear surface side of the substrate 54e, is formed in the support portion 240b. The distal end surface 58a of the optical fiber 58 is contact with the rear surface of the substrate 54e. Here, the distal end surface 58a of the optical fiber 58 may be close to the rear surface of the substrate 54e.

In a case of using such an oxygen sensor 20f, the fluorescent body 56 extends in the direction orthogonal to the shaft line of the shaft 22f, and thus, it is possible to efficiently bring the urine introduced into the urine introduction lumen 42 from the urine introduction port 28a, into contact with the fluorescent body 56.

In this modification example, the same effect is obtained according to the same configuration as that of the oxygen measurement devices 10A to 10F described above.

Seventh Modification Example

Figure 19A:
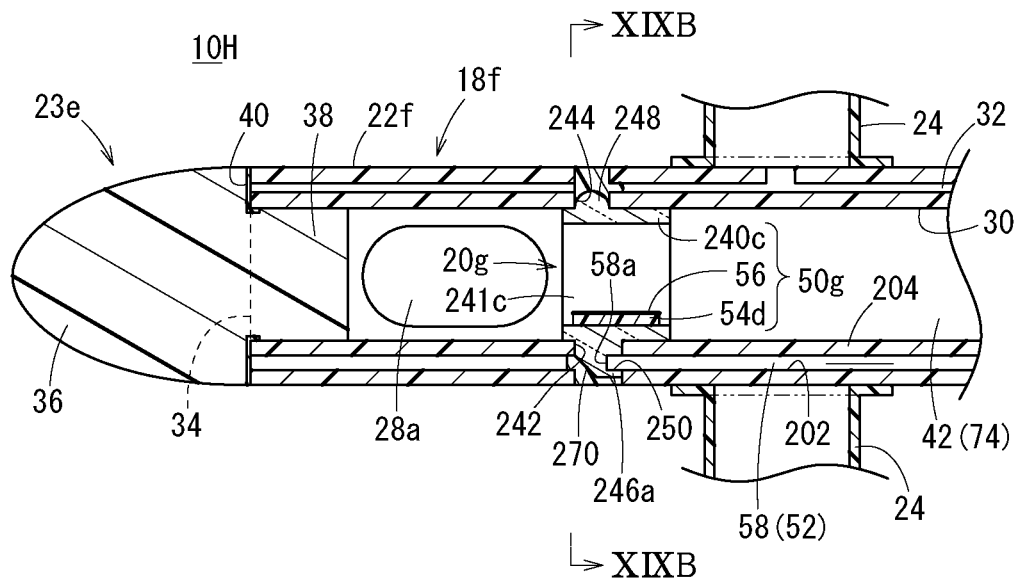
FIG. 19A is a partially omitted longitudinal sectional view of an oxygen measurement device according to a seventh modification example.
Figure 19B:
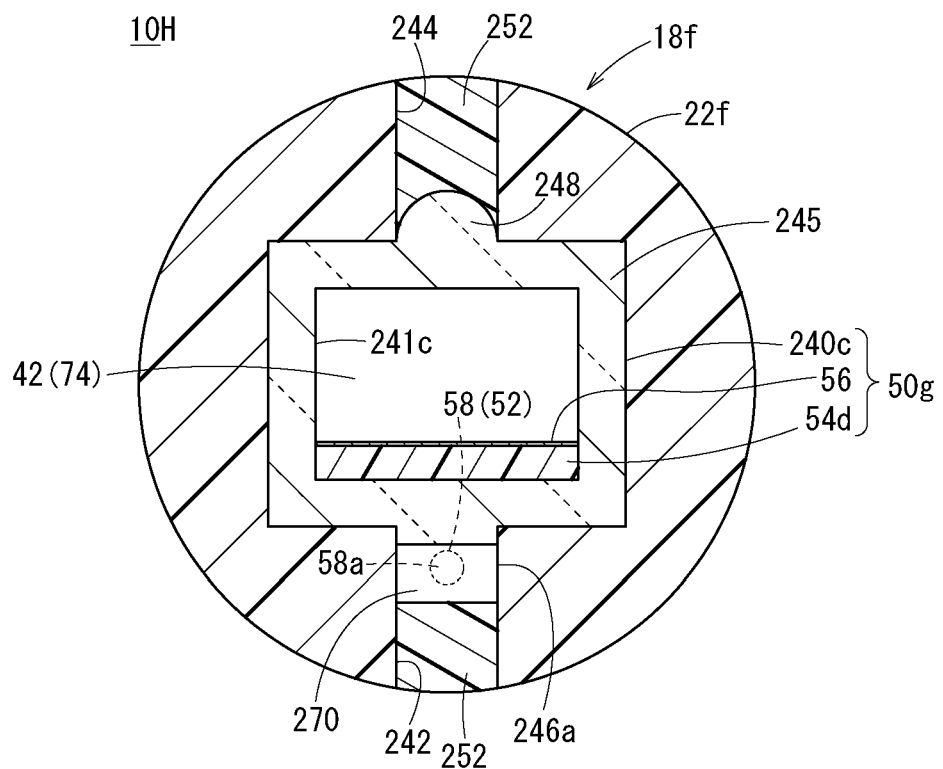
FIG. 19B is a transverse sectional view along line XIXB-XIXB of FIG. 19A.

Next, the oxygen measurement device 10H according to the seventh modification example will be described. As illustrated in FIG. 19A and FIG. 19B, the oxygen measurement device 10H according to the seventh modification example includes an oxygen sensor 20g. A support portion 240c of an oxygen sensor main body 50g configuring the oxygen sensor 20g, can be fabricated from a material which is capable of transmitting the excitation light from the optical fiber 58 and the fluorescence from the fluorescent body 56. Examples of such a material include the same material as that of the substrate 54d. The substrate 54d is fixed to a wall surface configuring an inner hole 241c of the support portion 240c in a state where the substrate 54d extends in the shaft line direction of the shaft 22f. A convex portion 246a protruding in the sensor lumen 202 is disposed in the support portion 240c, and the positioning hole 250 into which the distal end of the optical fiber 58 is fitted, is formed in the convex portion 246a. The distal end surface 58a of the optical fiber 58 is directed towards the distal end direction in a state where the distal end of the optical fiber 58 is fitted into the positioning hole 250. That is, the optical fiber 58 is fitted into the positioning hole 250 in a state where the optical fiber 58 linearly extends from the sensor lumen 202. That is, the fluorescent body 56 is positioned in a direction intersecting with (a direction orthogonal to) a direction directed by the distal end surface 58a of the optical fiber 58.

A reflection portion 270 which guides the excitation light from the optical fiber 58 to the fluorescent body 56 and guides the fluorescence from the fluorescent body 56 into the optical fiber 58, is formed in the convex portion 246a. The reflection portion 270, for example, can be configured as a mirror in which a plane obtained by obliquely cutting out a part of the convex portion 246a, is coated with a metal film. Here, the reflection portion 270 may have any configuration insofar as being capable of reflecting the excitation light from the optical fiber 58 and the fluorescence from the fluorescent body 56.

In a case of using such an oxygen sensor 20g, for example, it is possible to irradiate the fluorescent body 56 with the excitation light from the optical fiber 58 by the reflection portion 270, and to receive the fluorescence from the fluorescent body 56 by the optical fiber 58, without bending the optical fiber 58.

In this modification example, the same effect is obtained according to the same configuration as that of the oxygen measurement devices 10A to 10G described above.

Eighth Modification Example

Figure 20A:
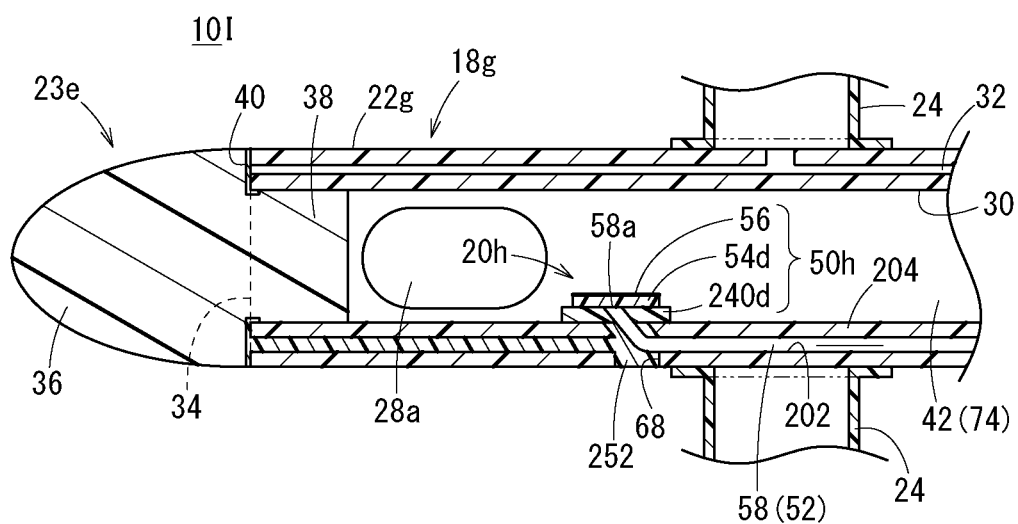
FIG. 20A is a partially omitted longitudinal sectional view of an oxygen measurement device according to an eighth modification example.
Figure 20B:
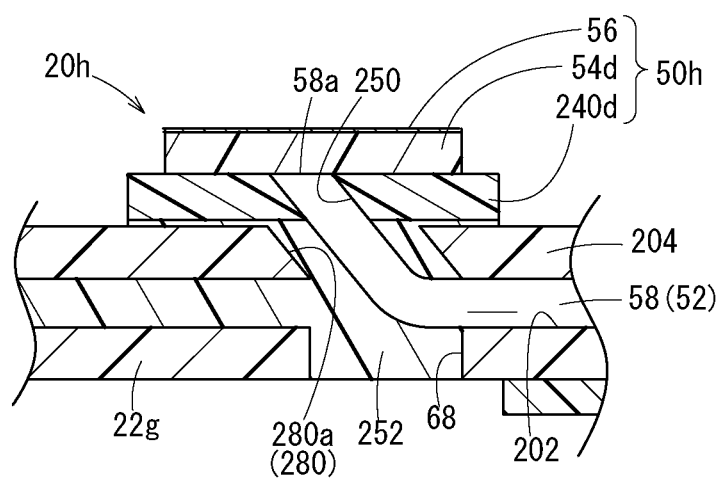
FIG. 20B is an enlarged view of the vicinity of the oxygen sensor main body of FIG. 20A.

Next, the oxygen measurement device 10I according to the eighth modification example will be described. As illustrated in FIG. 20A and FIG. 20B, the oxygen measurement device 10I according to the eighth modification example includes a urethral catheter 18g and an oxygen sensor 20h. The urethral catheter 18g includes a shaft 22g and the blocking portion 23e.

An oxygen sensor main body 50h of the oxygen sensor 20h is fixed to the shaft 22g such that the fluorescent body 56 is positioned on the proximal end side from the urine introduction port 28a in the urine introduction lumen 42. The substrate 54d of the oxygen sensor main body 50h is configured into the shape of a flat plate, extends in a shaft line direction of the shaft 22g, and is fixed to a flat plate support portion 240d such that the fluorescent body 56 is directed inwardly to the urine introduction lumen 42. The positioning hole 250 (the positioning portion) into which the distal end of the optical fiber 58 is fitted, is formed in the support portion 240d. The positioning hole 250 is positioned on a rear surface side of the substrate 54d.

The distal end of the optical fiber 58 is fitted into the positioning hole 250 in a state where the optical fiber 58 is inserted into an insertion hole 280 formed in the partition wall 204. A wall surface 280a configuring the insertion hole 280 is sloped in a distal end direction from the sensor lumen 202 side towards the urine introduction lumen 42 side. The distal end surface 58a of the optical fiber 58 is in contact with the rear surface of the substrate 54d in a state where the distal end of the optical fiber 58 is fitted into the positioning hole 250. Here, the distal end surface 58a of the optical fiber 58 may be close to the rear surface of the substrate 54d. The support portion 240d and the optical fiber 58 are fixed (i.e., attached) to the shaft 22g by the adhesive agent 252 filled to seal the through hole 68 and the insertion hole 280, which are formed on an outer surface of the shaft 22g.

Next, the assembly of the oxygen sensor 20h with respect to the urethral catheter 18g will be described. Furthermore, in an initial state, the substrate 54d coated with the fluorescent body 56, is fixed to the support portion 240d by an adhesive agent (not illustrated) or the like. In this modification example, in a state where the optical fiber 58 is inserted into the sensor lumen 202, the distal end of the optical fiber 58 is drawn out in the distal end direction from the distal end opening portion 34 of the shaft 22g. In such a state, the optical fiber 58 is inserted into the insertion hole 280. Then, in state where the distal end of the optical fiber 58 is fitted into the positioning hole 250 of the support portion 240d, and a rear surface of the support portion 240d is coated with the adhesive agent, the support portion 240d is inserted from the distal end opening portion 34 of the shaft 22g while the optical fiber 58 is pulled back in a proximal end direction, and is brought into contact with the wall surface configuring the urine introduction lumen 42 such that the insertion hole 280 is covered from the urine introduction lumen 42 side. Then, the adhesive agent 252 is injected into the sensor lumen 202 and the insertion hole 280 from the outside of the shaft 22g through the through hole 68, and thus, the support portion 240d and the optical fiber 58 are fixed to the shaft 22g. Accordingly, it is possible to accurately position the fluorescent body 56 and the distal end surface 58a of the optical fiber 58. After that, the protruding portion 38 of the blocking portion 23e is fitted into the distal end opening portion 34 of the shaft 22g.

In this modification example, the same effect is obtained according to the same configuration as that of the oxygen measurement devices 10A to 10H.

Figure 21A:
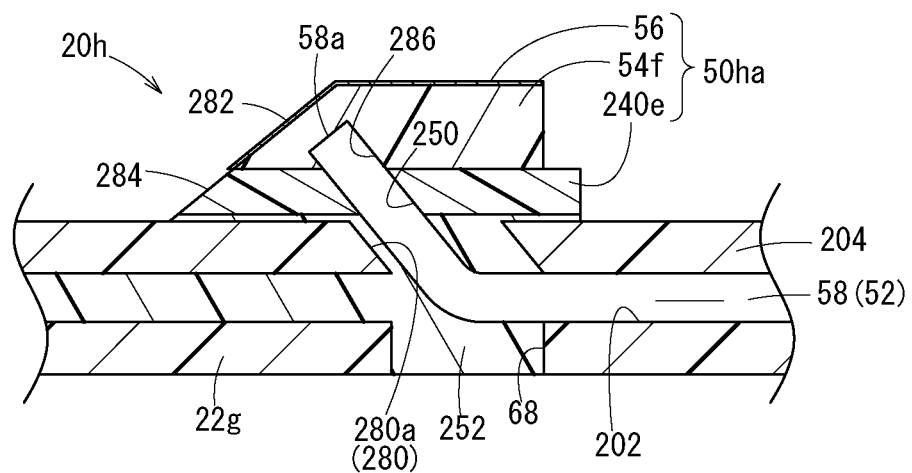
FIG. 21A is an enlarged view illustrating a configuration example of an oxygen sensor main body illustrated in FIG. 20B.

In this modification example, the oxygen sensor 20h may include an oxygen sensor main body 50ha illustrated in FIG. 21A. A slope 282 is formed on the distal end of the shaft 22g in the shaft line direction, on a substrate 54f of the oxygen sensor main body 50ha, and a slope 284 is formed on the distal end of the shaft 22g in the shaft line direction, in a support portion 240e. Each of the slopes 282 and 284 is sloped in a direction opposite to the sensor lumen 202 (inwardly to the shaft 22g) towards the proximal end direction of the shaft 22g. The slope 282 and the slope 284 are flush with each other. The fluorescent body 56 is applied to the slope 282, and a surface continuous from the slope 282 in the proximal end direction. A concave portion 286 continuous to the positioning hole 250 of the support portion 240e, is formed on a rear surface of the substrate 54f. The distal end of the optical fiber 58 is fitted into the concave portion 286 and the positioning hole 250. In addition, the distal end surface 58a of the optical fiber 58 is parallel to the slope 282 (the fluorescent body 56 applied to the slope 282), in a state where the distal end of the optical fiber 58 is fitted into the concave portion 286 and the positioning hole 250. Furthermore, the sensor lumen 202 extends up to the distal end of the shaft 22g.

In a case of using such an oxygen sensor 20h, the fluorescent body 56 applied to the slope 282, extends to be sloped inwardly to the shaft 22g towards the proximal end direction of the shaft 22g, and thus, it is possible to efficiently bring the urine in the urine introduction lumen into contact with the fluorescent body 56.

Figure 21B:
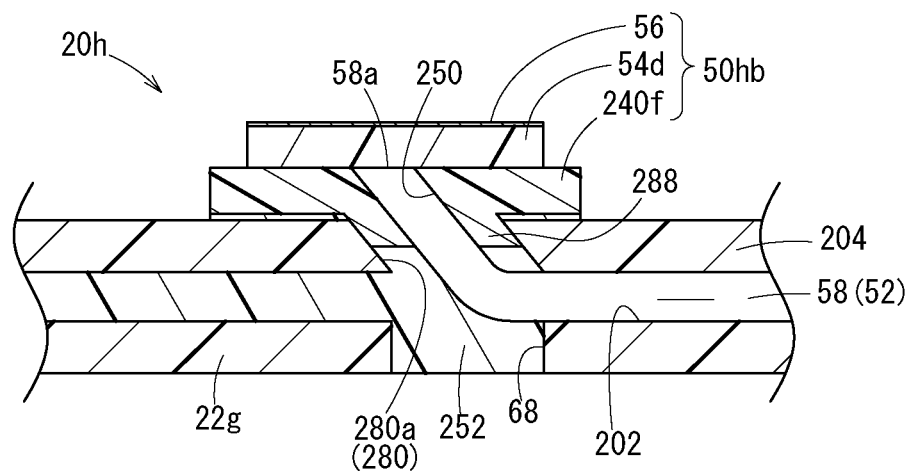
FIG. 21B is an enlarged view illustrating another configuration example of the oxygen sensor main body.

In addition, the oxygen sensor 20h may include an oxygen sensor main body 50hb illustrated in FIG. 21B. A protruding portion 288 to be fitted into the insertion hole 280, is disposed in a support portion 240f of the oxygen sensor main body 50hb. In this case, it is possible to rather easily and accurately position the support portion 240f in the insertion hole 280.

In this modification example, in the urethral catheter 18g, the through hole 68 may be omitted. In this case, in a state where the support portions 240d to 240f are positioned on the wall surface configuring the urine introduction lumen 42, the adhesive agent 252 is injected from the distal end opening portion of the sensor lumen 202. Accordingly, the sensor lumen 202 and the insertion hole 280 are filled with the adhesive agent 252, and thus, the support portions 240d to 240f and the optical fiber 58 can be fixed (i.e., attached) to the shaft 22g.

Ninth Modification Example

Next, the oxygen measurement device 10J according to the ninth modification example will be described. As illustrated in FIG. 22A and FIG. 22B, the oxygen measurement device 10J according to the ninth modification example includes a urethral catheter 18h and an oxygen sensor 300.

The sensor lumen 202 which is opened in a portion positioned in a proximal end direction of the shaft 22h, in a wall surface configuring a urine introduction port 28c, is formed in a shaft 22h of the urethral catheter 18h. The oxygen sensor 300 is configured as a fluorescent oxygen sensor, and includes an oxygen sensor main body 302 capable of detecting the oxygen in the urine, and a transfer portion 304 extending along the shaft 22h in which the oxygen sensor main body 302 is integrally disposed on a distal end. That is, the oxygen sensor main body 302 is integrally disposed on the distal end of the transfer portion 304. The transfer portion 304 is configured of an optical fiber, and the oxygen sensor main body 302 is configured by including a fluorescent body. Here, the oxygen sensor 300 may be configured as an electrode type oxygen sensor. In this case, the transfer portion 304 is electrically connected to the oxygen sensor main body 302.

A distal end surface 302a of the oxygen sensor main body 302 is positioned in the urine introduction port 28c. In the urine introduction port 28c, an opening width along a circumferential direction of the distal end is greater than an opening width along a circumferential direction of a proximal end. In other words, the urine introduction port 28c is formed such that an opening width along the circumferential direction increases towards the distal end direction of the shaft 22h.

According to this modification example, the oxygen sensor main body 302 is integrally disposed on (fixed to) the distal end of the transfer portion 304, and thus, it is possible to rather easily assemble the oxygen sensor 300 with respect to the shaft 22h.

In addition, the oxygen sensor main body 302 is positioned in the urine introduction port 28c. For this reason, the oxygen sensor main body 302 can be brought into contact with the urine flowing from the urine introduction port 28c.

Further, the transfer portion 304 is provided in the sensor lumen 202, and thus, it is possible to help prevent the discharge of the urine in the urinary passage 74 from being inhibited by the transfer portion 304.

In this modification example, the oxygen sensor main body 302 is positioned on the proximal end of the urine introduction port 28c, that is, a portion having a narrow opening width. For this reason, it is possible to stably (i.e., reliably) measure the oxygen in the urine in a portion of the urine introduction port 28c of which the shape is hardly deformed even in a case of receiving an external force, and to help prevent the sensor from being broken due to the deformation. Furthermore, the oxygen sensor main body 302 and the transfer portion 304 may be assembled in the sensor lumen 202 in a state of being separated from each other in advance, may be positioned in or fitted into the sensor lumen 202, and then, may be fixed by injecting an adhesive agent through a through hole (not illustrated).

Figure 23:
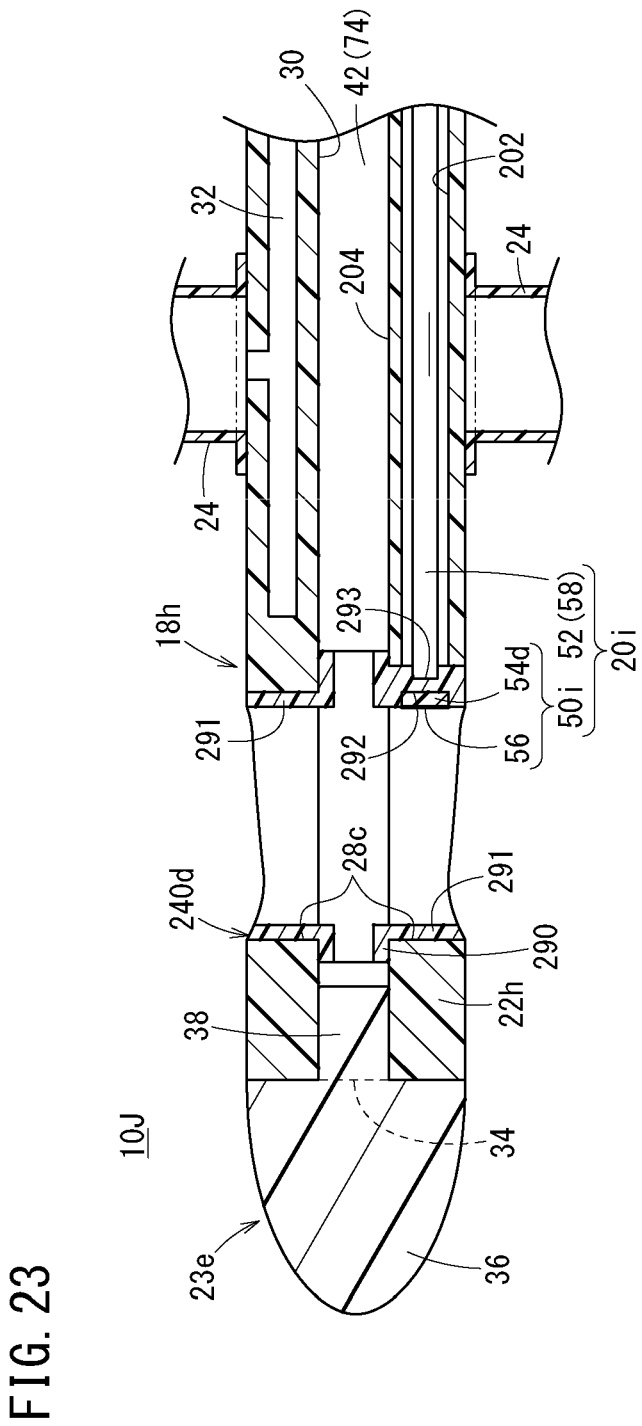
FIG. 23 is a longitudinal sectional view illustrating a configuration example of the oxygen measurement device of FIG. 22A.

As illustrated in FIG. 23, the oxygen measurement device 10J may include an oxygen sensor 20i, instead of the oxygen sensor 300. The oxygen sensor 20i includes an oxygen sensor main body 50i, a transfer portion 52 (an optical fiber 58), and a support portion 240d supporting the oxygen sensor main body 50i. The oxygen sensor main body 50i is formed by applying the fluorescent body 56 onto a front surface of the substrate 54d on a flat plate. The support portion 240d is fabricated of a material having transparency such that the excitation light and the fluorescence can be transmitted, and includes a hollow support portion main body 290 which is disposed in the urine introduction lumen 42, and a set of hollow protruding portions 291 which extend in opposite directions to each other from the support portion main body 290, and are disposed in each of the urine introduction ports 28c. The lumen of the support portion main body 290 extends along the shaft line direction of the shaft 22h over the entire length of the support portion main body 290, and communicates with the lumen of each of the protruding portions 291. An outer surface of the protruding portion 291 is in contact with a wall surface configuring the urine introduction port 28c to cover the opening portion on the distal end side of the sensor lumen 202. A protruding length of the protruding portion 291 is set to be the same as a length dimension of the urine introduction port 28c along a diameter direction of the shaft 22h (a thickness dimension of the shaft 22h). For this reason, the protruding portion 291 does not protrude to the outside from the urine introduction port 28c.

A concave portion 292 is formed on the distal end side of the sensor lumen 202, in an inner surface of the protruding portion 291. The substrate 54d is fixed to the concave portion 292 by an adhesive agent (not illustrated) or the like in a state of the substrate 54d being fitted into the concave portion 292, such that the fluorescent body 56 is in contact with the urine discharged through the lumen of the protruding portion 291. A positioning concave portion 293 into which the distal end of the optical fiber 58 is fitted into, is formed in a portion covering the sensor lumen 202 in the outer surface of the protruding portion 291 (a side opposite to the concave portion 292).

Next, the assembly of the oxygen sensor 20i with respect to the urethral catheter 18h will be described. Furthermore, in an initial state, the substrate 54d coated with the fluorescent body 56, is fixed (i.e., attached) to the support portion 240d by an adhesive agent (not illustrated) or the like. In this case, in a state where the optical fiber 58 is inserted into the sensor lumen 202, the distal end of the optical fiber 58 is drawn out (extends outward) from the opening portion of the sensor lumen 202 on the distal end side in the distal end direction, by a fitted length. Then, the support portion 240d is inserted from the distal end opening portion 34 of the shaft 22h, and the protruding portion 291 is fitted into the urine introduction port 28c. At this time, the distal end of the optical fiber 58 is fitted into the positioning concave portion 293 of the support portion 240d. After that, the support portion 240d, the optical fiber 58, and the sensor lumen 202 adhere to each other by using an adhesive agent (not illustrated). As necessary, a portion of the optical fiber 58, which is drawn out in the distal end direction, is pushed by the support portion 240d, and is pushed back in the proximal end direction. In addition, the support portion 240d and the shaft 22h adhere to each other by using an adhesive agent (not illustrated), as necessary. According to such a configuration, the same effect as that of the embodiments described above is obtained. Furthermore, the distal end of the optical fiber 58 may be inserted from the distal end opening portion 34 of the shaft 22h in a state of being fitted in advance into the positioning concave portion 293 of the support portion 240d.

Tenth Modification Example

Next, the oxygen measurement device 10K according to the tenth modification example will be described. As illustrated in FIG. 24A, the oxygen measurement device 10K according to the tenth modification example includes a urethral catheter 18i and the oxygen sensor 300. The oxygen sensor 300 is the same as that described in the ninth modification example.

The urine introduction lumen 42 which extends in an axial direction of the shaft 22i, the sensor lumen 202 in which the transfer portion 304 of the oxygen sensor 300 is provided, and a lateral urine introduction lumen 310 which is in communication with the urine introduction lumen 42, and is disposed on the distal end side of the sensor lumen 202, are formed in a shaft 22i of the urethral catheter 18i. The lateral urine introduction lumen 310 is positioned on the proximal end side from the urine introduction port 28a. The oxygen sensor 300 extends in the lateral urine introduction lumen 310 such that the oxygen sensor main body 302 is positioned in the urine introduction lumen 42. The distal end of the oxygen sensor main body 302 is positioned in the vicinity of the proximal end side of the urine introduction port 28a. Furthermore, the distal end of the sensor lumen 202 is filled with an adhesive agent (not illustrated), which seals the sensor lumen 202, and fixes (i.e., attaches) the transfer portion 304 to the shaft 22i.

According to this modification example, the transfer portion 304 is provided in the sensor lumen 202, and thus, it is possible to help prevent the discharge of the urine in the urine introduction lumen 42 from being inhibited by the transfer portion 304. Accordingly, it is possible to rather smoothly discharge the urine in the urine introduction lumen 42. In addition, it is possible to efficiently bring the oxygen sensor main body 302 into contact with the urine in the urine introduction lumen 42.

In the oxygen measurement device 10K, as illustrated in FIG. 24B, the lateral urine introduction lumen 310 may be in communication with distal end of the urine introduction lumen 42. That is, the lateral urine introduction lumen 310 is in the same position as that of the distal end of the urine introduction port 28a, in a shaft line direction of the shaft 22i. In this case, the transfer portion 304 is turned back on the proximal end side, for example, at 180° from the lateral urine introduction lumen 310 towards the urine introduction lumen 42, and thus, the oxygen sensor main body 302 is positioned on the proximal end side of the urine introduction port 28a. Accordingly, it is possible to efficiently bring the oxygen sensor main body 302 into contact with the urine introduced into the urine introduction lumen 42 from the urine introduction port 28a.

Figure 25:
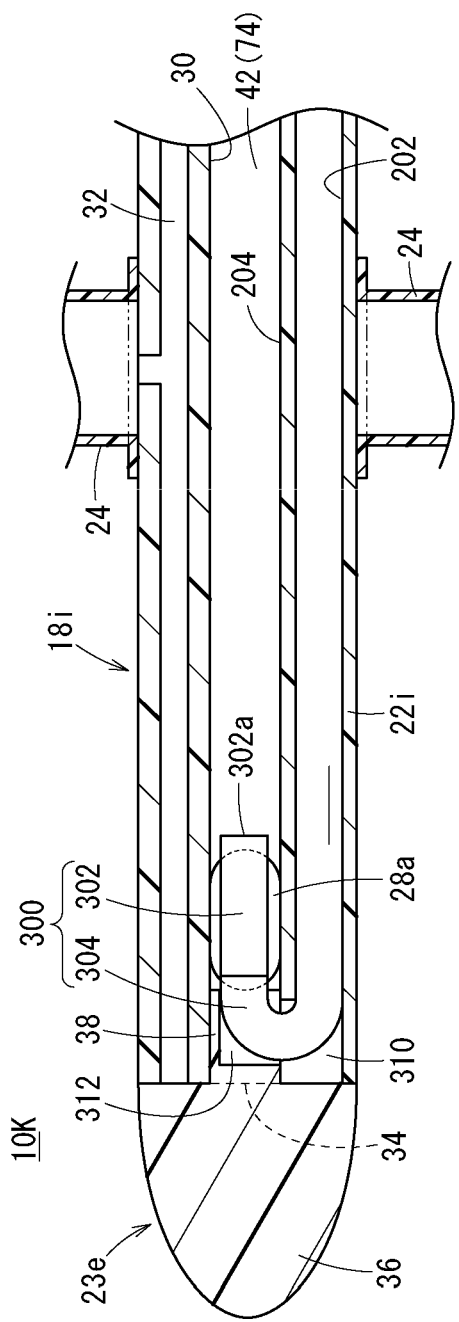
FIG. 25 is a longitudinal sectional view illustrating another configuration example of the oxygen measurement device illustrated in FIG. 24A.

In addition, as illustrated in FIG. 25, an arrangement hole 312 in which the turned-back portion of the transfer portion 304 is disposed, may be formed in the protruding portion 38 of the blocking portion 23e. In this case, the protruding portion 38 holds the turned-back portion of the transfer portion 304. Accordingly, it is possible to help suppress positional displacement of the oxygen sensor main body 302 in the urine introduction lumen 42.

Second Embodiment

Next, an oxygen measurement system 12A according to a second embodiment will be described. Furthermore, in the oxygen measurement system 12A according to this embodiment, the same reference numerals will be applied to the same constituents as those of the oxygen measurement system 12 described above, and the detailed description of the same reference numerals and the same constituents as those of the oxygen measurement system 12 described above will be omitted.

Figure 26:
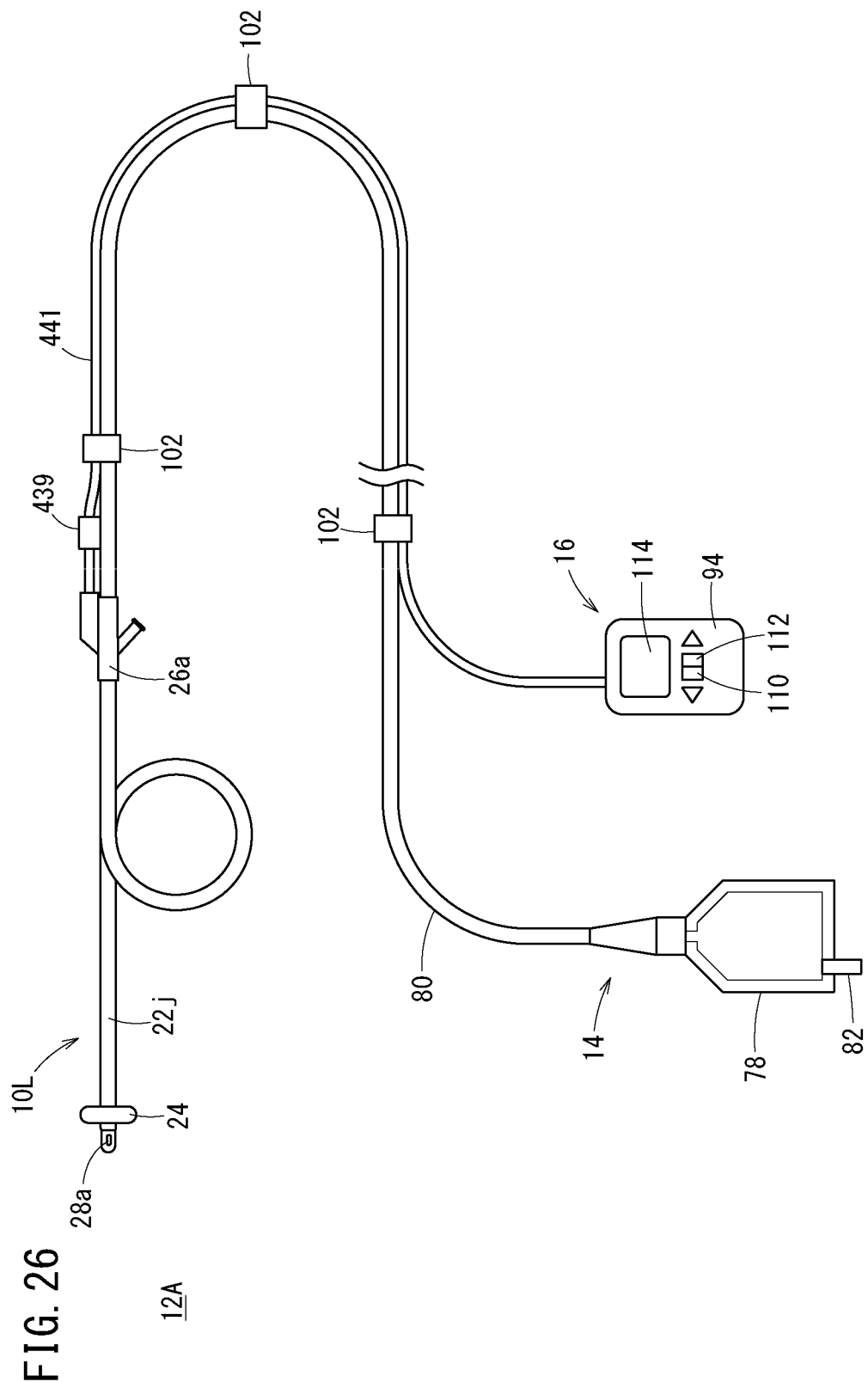
FIG. 26 is a schematic view illustrating a schematic configuration of an oxygen measurement system including an oxygen measurement device according to a second embodiment of the disclosure.

The oxygen measurement system 12A illustrated in FIG. 26 is configured to measure the oxygen partial pressure (the oxygen concentration) in the urine which is discharged into the bladder 140 from the kidney, in order to predict the state of the kidney, and includes an oxygen measurement device 10L, a urine collection bag 14 (a urine collection container), and a monitoring system 16.

Figure 27:
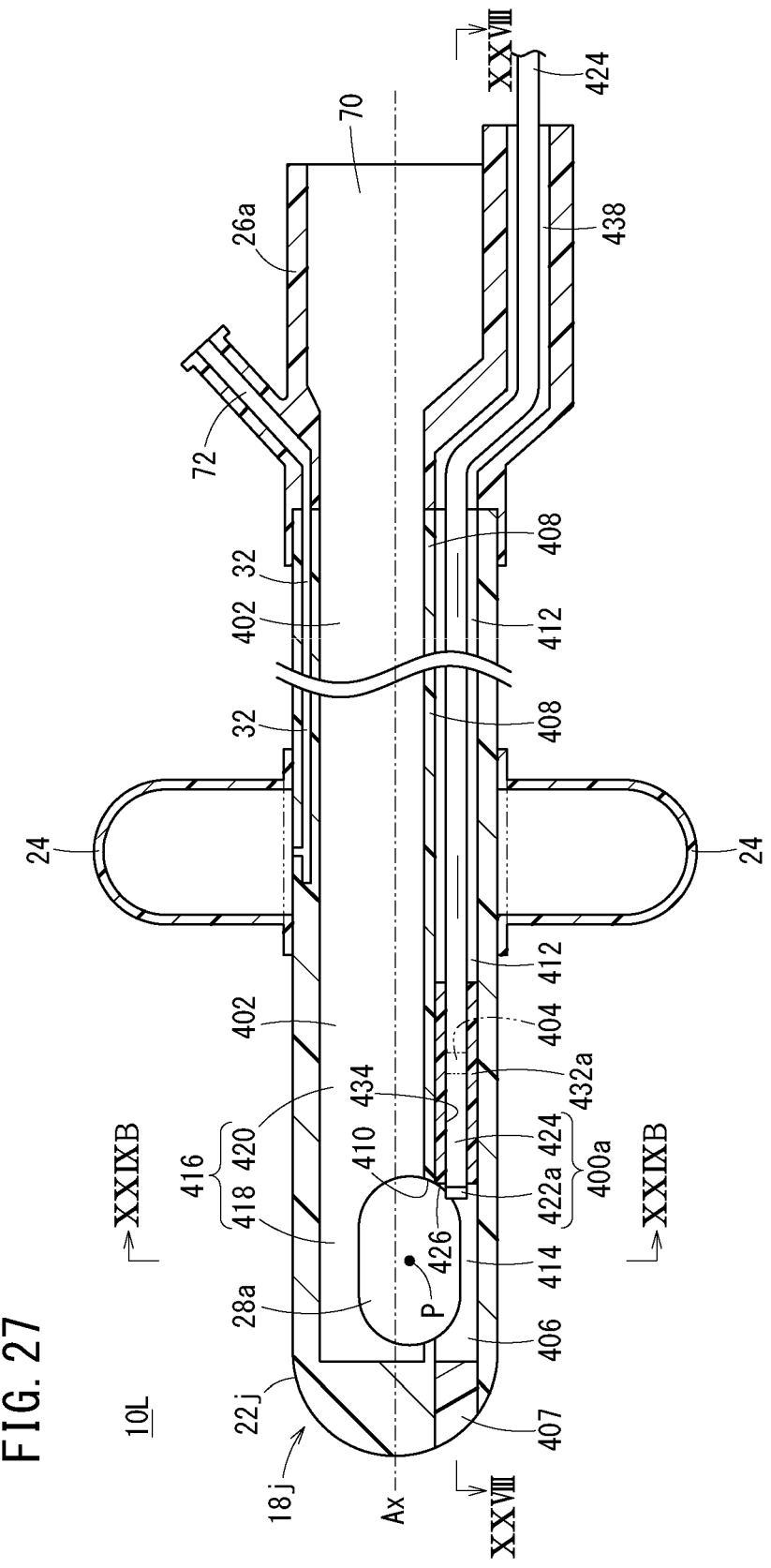
FIG. 27 is a partially omitted longitudinal sectional view of the oxygen measurement device of FIG. 26.

As illustrated in FIG. 26 and FIG. 27, the oxygen measurement device 10L includes a urethral catheter 18j and an oxygen sensor 400a. The urethral catheter 18j is a medical device which is indwelt in the living body at the time of being used, and urinates the urine in the bladder 140 to the urine collection bag 14 disposed on the outside of the body. The urethral catheter 18j includes a thin and elongated hollow shaft 22j, a balloon 24 disposed in a distal end portion of the shaft 22j, and a hub 26a disposed in a proximal end portion of the shaft 22j.

The shaft 22j is an elongated tube of which the most-distal end is in the shape of a hemisphere. The shaft 22j has suitable flexibility and suitable stiffness such that a distal end portion of the urethral catheter 18j can be smoothly inserted into the bladder 140 through the urethra 144. The shaft 22j material, for example, can include the same material as that of the shaft 22a described above.

As illustrated in FIG. 27, two urine introduction ports 28a allowing the urine in the bladder 140 to flow into the shaft 22j, a urine introduction lumen 402 which extends along a shaft line direction of the shaft 22j, and functions as a urination flow path, a lateral lumen 406 in which the oxygen sensor 400a and a temperature sensor 404 are provided, and the dilation lumen 32 for circulating the dilation fluid in the balloon 24, are formed in the shaft 22j.

Each of the urine introduction ports 28a is opened in a portion on a distal end side from the balloon 24, in an outer circumference surface of the shaft 22j. In an illustrated example, two urine introduction ports 28a are disposed in positions facing each other (refer to FIG. 27 and FIG. 28B). The shape, the size, the position, and the number of urine introduction ports 28a can be set as desired.

The urine introduction lumen 402 is disposed such that a shaft line Ax (i.e., axial direction) of the shaft 22j is positioned in the urine introduction lumen 402. A distal end of the urine introduction lumen 402 is positioned on the distal end side from the urine introduction port 28a in the shaft 22j, and a proximal end of the urine introduction lumen 402 is opened on the proximal end of the shaft 22j. The urine introduction lumen 402 is in communication with the urine introduction port 28a.

The lateral lumen 406 extends along the shaft line (i.e., axial) direction of the shaft 22j in parallel with the urine introduction lumen 402. A distal end of the lateral lumen 406 is opened on a distal end surface (a hemisphere surface) of the shaft 22j, and a proximal end of the lateral lumen 406 is opened on the proximal end of the shaft 22j. Furthermore, an opening portion 426 of the distal end of the lateral lumen 406 is blocked by a blocking member 407. A transverse sectional area of the lateral lumen 406 is less than a flow path sectional area of the urine introduction lumen 402.

A partition wall 408 extending along the urine introduction lumen 402 is disposed between the urine introduction lumen 402 and the lateral lumen 406. A through hole 410 allowing the urine introduction lumen 402 and the lateral lumen 406 to be in communication with each other, is disposed in a distal end portion of the partition wall 408.

The urine introduction port 28a is opened on an inner surface of a distal end portion of the lateral lumen 406. That is, the lateral lumen 406 communicates with the urine introduction port 28a without passing through the urine introduction lumen 402. In other words, the urine introduction port 28a is positioned to straddle both of the urine introduction lumen 402 and the lateral lumen 406. That is, the urine introduction port 28a is disposed such that a center P is positioned on the lateral lumen 406 side from the shaft line Ax of the shaft 22j. Thus, in a case where the urine introduction port 28a straddles both of the urine introduction lumen 402 and the lateral lumen 406, a process of forming the urine introduction port 28a and a process of forming the through hole 410 can be simultaneously performed, and thus, it is possible to reduce manufacturing man-hours of the urethral catheter 18j.

The proximal end side from the through hole 410 in the lateral lumen 406, functions as a sensor lumen 412 in which the oxygen sensor 400a and the temperature sensor 404 are provided. The distal end side from the sensor lumen 412 in the lateral lumen 406, functions as a lateral urine introduction lumen 414 through which the urine flowing from the urine introduction port 28a is discharged. In the following description, the urine introduction lumen 402, the through hole 410, and the lateral urine introduction lumen 414 may be collectively referred to as a urinary passage 416. That is, the urine flowing from the urine introduction port 28a is flowing in the urinary passage 416. In addition, a region of the urinary passage 416 in which the urine introduction port 28a is positioned (the distal end portion of the urine introduction lumen 402, the through hole 410, and the lateral urine introduction lumen 414) may be referred to as a first urinary passage portion 418, and a region on the proximal end side from the through hole 410 in the urinary passage 416, may be referred to as a second urinary passage portion 420.

Figure 28:
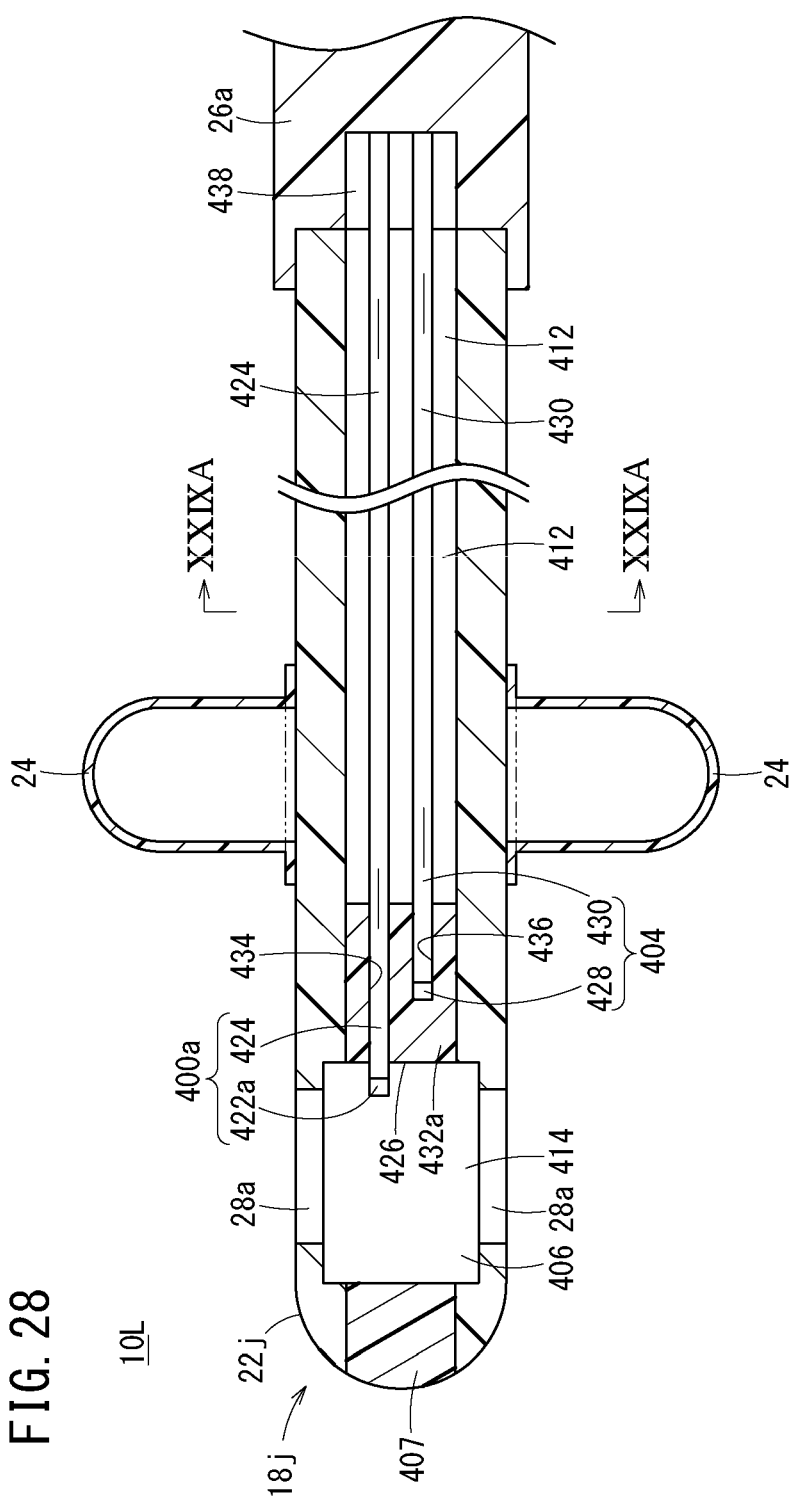
FIG. 28 is a longitudinal sectional view along line XXVIII-XXVIII of FIG. 27.

As illustrated in FIG. 27 and FIG. 28, the sensor lumen 412 is shorter than the urine introduction lumen 402. The oxygen sensor 400a provided in the sensor lumen 412, is configured as a so-called fluorescent oxygen sensor, and includes an oxygen sensor main body 422a (an oxygen probe) capable of detecting the oxygen in the urine, and a transfer portion 424 (an oxygen transfer portion) optically connected to the oxygen sensor main body 422a. The oxygen sensor main body 422a includes a glass optical fiber or a plastic optical fiber. In this case, the core of the optical fiber is exposed to a distal end surface of the oxygen sensor main body 422a. Here, the oxygen sensor 400a may be configured as an electrode type oxygen sensor 400a. In this case, the transfer portion 424 is electrically connected to the oxygen sensor main body 422a. Here, the transfer portion 424 is not limited to an optical and electrical portion, and may be a magnetic or mechanical portion.

The oxygen sensor main body 422a is positioned in the lateral urine introduction lumen 414 (the urinary passage 416). Specifically, the oxygen sensor main body 422a is positioned on the proximal end side from the center of the urine introduction port 28a, and is adjacent to a direction orthogonal to the shaft line direction of the shaft 22j with respect to the urine introduction port 28a. That is, the oxygen sensor main body 422a is adjacent to the proximal end side of the urine introduction port 28a. In other words, the oxygen sensor main body 422a is adjacent to the through hole 410 in the direction orthogonal to the shaft line direction of the shaft 22j. That is, the oxygen sensor main body 422a is not exposed to the outside of the shaft 22j.

The transfer portion 424 is a cable for optically connecting the oxygen sensor main body 422a and the monitoring system 16 together. The transfer portion 424 is optically connected to the oxygen sensor main body 422a through the opening portion 426 of the sensor lumen 412 on the distal end side. In an illustrated example, the opening portion 426 of the sensor lumen 412 is directed towards the shaft line direction (the distal end side) of the shaft 22j. In addition, an opening area of the opening portion 426 of the sensor lumen 412 is less than an opening area of the urine introduction port 28a. Further, the opening portion 426 of the sensor lumen 412 is positioned in the direction orthogonal to the shaft line direction of the shaft 22j with respect to the urine introduction port 28a.

The temperature sensor 404 provided in the sensor lumen 412, includes a temperature sensor main body 428 (a temperature probe) for detecting the temperature of the urine flowing in the urinary passage 416, and a transfer portion 430 (a temperature transfer portion) electrically connected to the temperature sensor main body 428.

The temperature sensor main body 428 is positioned between the oxygen sensor main body 422a and the balloon 24. That is, the temperature sensor main body 428 is positioned in the bladder 140 at the time of using the urethral catheter 18j. The transfer portion 430 is a cable for electrically connecting the temperature sensor main body 428 and the monitoring system 16 together. The transfer portion 430 is juxtaposed (i.e., placed side by side) with the transfer portion 424 in the sensor lumen 412.

The position of the temperature sensor main body 428 can be set as desired. For example, the temperature sensor main body 428 may be adjacent to the oxygen sensor main body 422a in the direction orthogonal to the shaft line direction of the shaft 22j. That is, the temperature sensor main body 428 may be positioned in the urinary passage 416. In addition, the transfer portion 424 and the transfer portion 430 may be integrated into one cable on the inside and the outside of the sensor lumen 412. In this case, it is possible to simplify the wiring of the transfer portion 424 and the transfer portion 430.

A fixing portion 432a (a distal end side fixing portion) for fixing the oxygen sensor 400a and the temperature sensor 404 to the inner surface configuring the sensor lumen 412, is disposed in the sensor lumen 412. The fixing portion 432a is disposed in a distal end portion of the sensor lumen 412. The fixing portion 432a is liquid-tightly in contact with the inner surface of the sensor lumen 412 such that the flow of the urine from the urinary passage 416 to the proximal end side from the fixing portion 432a in the sensor lumen 412 is inhibited.

Specifically, the material of fixing portion 432a, is preferably fabricated from a material that is flexible, and a distal end portion of the transfer portion 424 is inserted (i.e., liquid-tightly inserted) into the insertion hole 434 of the fixing portion 432a, and the fixing portion 432 is fitted (i.e. liquid-tightly fitted) into the distal end portion of the sensor lumen 412 in a state where the temperature sensor main body 428 and a distal end portion of the transfer portion 430 are inserted into a hole 436 of the fixing portion 432a. A distal end of the insertion hole 434 is positioned in the vicinity of the urine introduction port 28a and the oxygen sensor main body 422a.

Figure 29A:
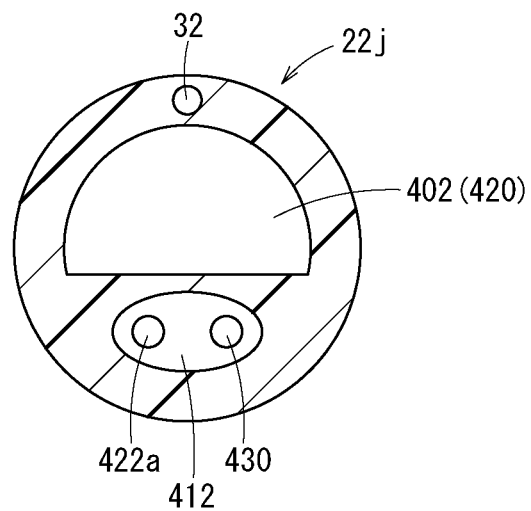
FIG. 29A is a transverse sectional view along line XXIXA-XXIXA FIG. 28.
Figure 29B:
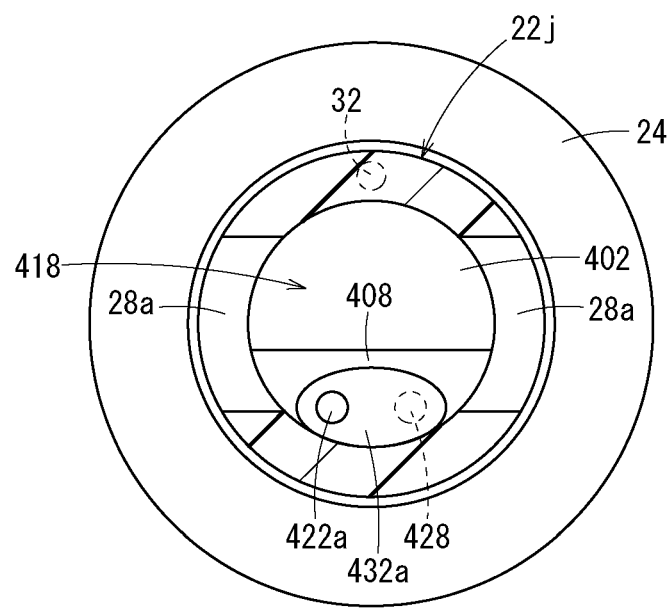
FIG. 29B is a transverse sectional view along line XXIXB-XXIXB of FIG. 27.

The fixing portion 432a is fabricated from the same material as that of the shaft 22j. The same material can include silicone or an adhesive agent containing silicone. In addition, the fixing portion 432a may be fixed to the inner surface configuring the sensor lumen 412 by an adhesive agent. A flow path sectional area of the first urinary passage portion 418 (a transverse sectional area orthogonal to the shaft line direction of the shaft 22j) is greater than a flow path sectional area of the second urinary passage portion 420 (a transverse sectional area) (refer to FIG. 29A and FIG. 29B).

In FIG. 27, the dilation lumen 32 is disposed in a wall portion on a side opposite to the lateral lumen 406 with respect to the urine introduction lumen 402. The distal end side of the dilation lumen 32 is in communication with the balloon 24, and the proximal end of the dilation lumen 32 is opened on the proximal end of the shaft 22j.

The hub 26a is integrally molded with a resin material into the shape of a hollow member. The urination port 70, the balloon dilation port 72, and a port 438 for disposing a sensor, are disposed on the hollow portion of the hub 26a. The transfer portion 424 and the transfer portion 430 are inserted into the port 438 for disposing a sensor. The oxygen transfer portion 424 and the transfer portion 430 are electrically and/or optically connected to a transfer cable 441 through a connecter 439 on the outside of the hub 26a (refer to FIG. 26). Furthermore, the transfer cable 441 is electrically and/or optically connected to the monitor main body portion 94.

In the oxygen measurement device 10L described above, the oxygen sensor main body 422a is positioned in the urinary passage 416. For this reason, the oxygen sensor main body 422a can be brought into contact with the urine flowing in the urinary passage 416. Accordingly, it is possible to rather accurately and reliably measure oxygen in fresh urine which is discharged from the kidney to the outside of the body through the urethral catheter 18j, through the bladder 140, but not the urine continuously remaining in the bladder 140. In addition, the displacement of the oxygen sensor main body 422a with respect to the shaft 22j can be suppressed by the fixing portion 432a, and thus, it is possible to improve a measurement accuracy of the oxygen sensor 400a.

Further, the transfer portion 424 and the transfer portion 430 are provided in the sensor lumen 412, and thus, it is possible to help prevent the discharge of the urine in the urinary passage 416 from being inhibited by the transfer portion 424 and the transfer portion 430. Accordingly, it is possible to rather smoothly discharge (urinate) the urine in the urinary passage 416.

In addition, a distal end portion of the oxygen sensor 400a (an end portion of the transfer portion 424 on the oxygen sensor main body 422a side) is fixed to the inner surface configuring the sensor lumen 412 by the fixing portion 432a, and thus, it is possible to efficiently suppress the displacement of the oxygen sensor main body 422a with respect to the shaft 22j. Accordingly, it is possible to improve the measurement accuracy of the oxygen sensor 400a.

In addition, a distal end portion of the temperature sensor 404 is fixed to the inner surface configuring the sensor lumen 412 by the fixing portion 432a, and thus, it is possible to efficiently suppress the displacement of the temperature sensor main body 428 with respect to the shaft 22*j*. Accordingly, it is possible to improve a measurement accuracy of the temperature sensor 404.

Further, the fixing portion 432*a* inhibits the flow of the urine from the urinary passage 416 to the proximal end side from the fixing portion 432*a* in the sensor lumen 412. In other words, the fixing portion 432*a* is disposed such that the distal end portion of the sensor lumen 412 is sealed in a state where the transfer portion 424 is inserted into the sensor lumen 412. Accordingly, it is possible to efficiently discharge the urine in the urinary passage 416. In addition, the periphery of the oxygen sensor main body 422*a* can be filled with the urine, and thus, it is possible to reliably bring the urine flowing in the urinary passage 416 into contact with the oxygen sensor main body 422*a*.

According to the oxygen measurement device 10L, the fixing portion 432*a* is made of a flexible material, and thus, it is possible to smoothly insert the shaft 22*j* into the bladder 140. In the oxygen measurement device 10L, the fixing portion 432*a* is positioned in the sensor lumen 412, and thus, it is possible to help prevent the discharge of the urine in the urinary passage 416 from being inhibited by the fixing portion 432*a*.

In the oxygen measurement device 10L, the flow path sectional area of the urinary passage 416 is greater than the transverse sectional area of the sensor lumen 412, and thus, it is possible to rather smoothly discharge the urine in the urinary passage 416.

In addition, at least a part of the urinary passage 416 extends along the shaft line direction of the shaft 22*j* to be parallel to the sensor lumen 412, and thus, it is possible to make a shape change and a stiffness change in a longitudinal direction of the shaft 22*j* comparatively small. Accordingly, when the shaft 22*j* is inserted into the bladder 140, the shaft 22*j* can be prevented from being buckled (i.e., bent or twisted) or the urinary passage 416 can be prevented from being blocked, and thus, it is possible to stably discharge the urine in the urinary passage 416.

According to the oxygen measurement device 10L, the sensor lumen 412 includes the opening portion 426 for exposing the oxygen sensor main body 422*a* into the urinary passage 416. For this reason, it is possible to provide the oxygen sensor main body 422*a* in the urinary passage 416 while providing the transfer portion 424 in the sensor lumen 412.

In addition, the opening portion 426 of the sensor lumen 412 on the distal end side is directed towards the shaft line direction of the shaft 22*j*, and thus, it is possible to position the oxygen sensor main body 422*a* in the urinary passage 416 without bending the transfer portion 424.

In the oxygen measurement device 10L, the flow path sectional area of the first urinary passage portion 418 is larger than the flow path sectional area of the second urinary passage portion 420, and thus, it is possible to allow the urine in the bladder 140 to efficiently flow into the first urinary passage portion 418 from the urine introduction port 28*a*. In addition, the oxygen sensor main body 422*a* is positioned in the first urinary passage portion 418, and thus, it is possible to reliably bring the urine flowing into the first urinary passage portion 418 from the bladder 140 through the urine introduction port 28*a* into contact with the oxygen sensor main body 422*a*.

In addition, the distal end of the insertion hole 434 of the fixing portion 432*a* is positioned in the vicinity of the urine introduction port 28*a*, and thus, it is possible to rather easily position the oxygen sensor main body 422*a* in the vicinity of the urine introduction port 28*a*.

According to the oxygen measurement device 10L, the oxygen sensor main body 422*a* is adjacent to the urine introduction port 28*a*, and thus, it is possible to reliably bring the urine flowing into the urinary passage 416 from the urine introduction port 28*a* into contact with the oxygen sensor main body 422*a*. In addition, the oxygen sensor main body 422*a* is adjacent to the proximal end side of the urine introduction port 28*a* (not positioned in the urine introduction port 28*a*), and thus, even in a case where the shaft 22*j* is buckled (i.e., bent or twisted) in the position of the urine introduction port 28*a*, it is possible to help prevent the oxygen sensor main body 422*a* from being broken.

Further, the oxygen sensor main body 422*a* is positioned in the direction orthogonal to the shaft line (i.e., axial) direction of the shaft 22*j* with respect to the urine introduction port 28*a*, and thus, it is possible to efficiently bring the urine flowing into the urinary passage 416 from the urine introduction port 28*a* into contact with the oxygen sensor main body 422*a*.

According to the oxygen measurement device 10L, the oxygen sensor main body 422*a* is positioned on the distal end side from the balloon 24, and thus, it is possible to position the oxygen sensor main body 422*a* in the bladder 140. Accordingly, it is possible to detect the oxygen in the urine in a comparatively stable environment (an environment in which a temperature change or the like is comparatively small). In addition, the shaft 22*j* can be held with respect to the bladder 140 by the balloon 24, and thus, it is possible to suppress the displacement of the oxygen sensor main body 422*a* in the bladder 140.

According to the oxygen measurement device 10L, the center P of the urine introduction port 28*a* is positioned on the sensor lumen 412 from the shaft line Ax of the shaft 22*j*, and thus, it is possible to rather easily position the oxygen sensor main body 422*a* to be adjacent to the urine introduction port 28*a*. In addition, the urine introduction port 28*a* is disposed in a portion of the shaft 22*j*, which is positioned on the distal end side from the sensor lumen 412, and thus, it is possible to reliably bring the urine flowing into the urinary passage 416 from the bladder 140 through the urine introduction port 28*a* into contact with the oxygen sensor main body 422*a*.

The oxygen measurement system 12A may include oxygen measurement devices 10La to 10Lt described below, instead of the oxygen measurement device 10L. Furthermore, in the oxygen measurement devices 10La to 10Lt, the same reference numerals will be applied to the same constituents as those of the oxygen measurement device 10L described above, and the detailed description of the same reference numerals and the same constituents as those of the oxygen measurement device 10L described above will be omitted. Furthermore, in the oxygen measurement devices 10La to 10Lt, actions and effects the same as or similar to those of the oxygen measurement device 10La, can be obtained with respect to the portions common to oxygen measurement device 10L.

Figure 30:
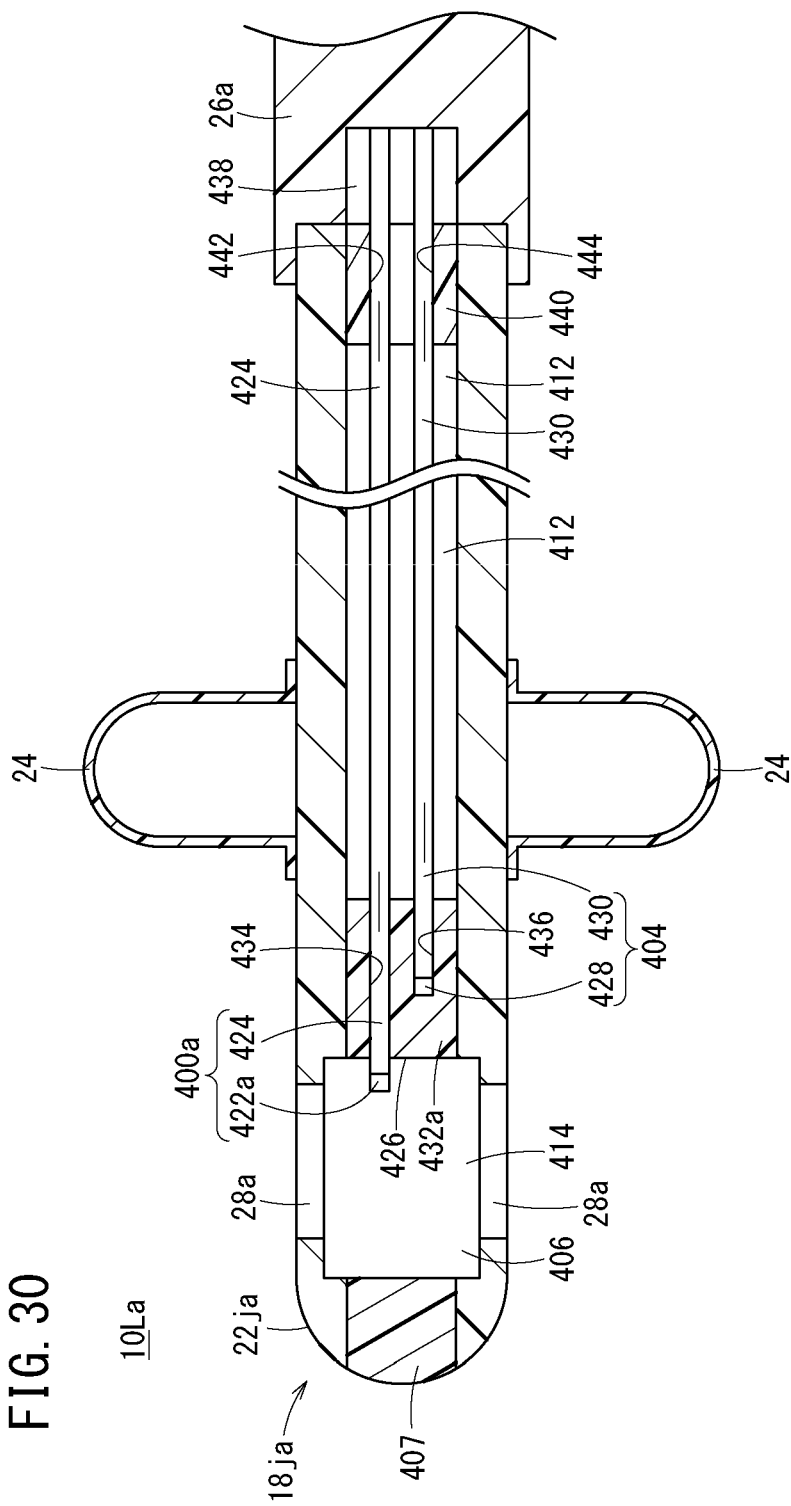
FIG. 30 is a sectional view illustrating a first configuration example of the oxygen measurement device of FIG. 27.

A fixing portion 440 (a proximal end side fixing portion) is disposed on a proximal end portion of the sensor lumen 412, in a shaft 22*ja* of a urethral catheter 18*ja* configuring the oxygen measurement device 10La illustrated in FIG. 30. The fixing portion 440 is made of a flexible material, inserts a proximal end portion of the transfer portion 424 into the insertion hole 442 of the fixing portion 440, and is fitted into the proximal end portion of the sensor lumen 412 in a state where a proximal end portion of the transfer portion 430 is inserted into an insertion hole 444 of the fixing portion 440. In this case, even in a case where an external force acts on the transfer portion 424 and the transfer portion 430, it is possible to suppress the displacement of the oxygen sensor main body 422a and the temperature sensor main body 428 with respect to the shaft 22ja. Accordingly, it is possible to improve a measurement accuracy of the oxygen sensor main body 422a and the temperature sensor main body 428. The fixing portion 440 may be configured to be more flexible than the fixing portion 432a positioned on the distal end side. The expansion and contraction of the urethral catheter 18ja are absorbed, and thus, it is possible to help prevent the oxygen sensor 400a from being broken.

Figure 31:
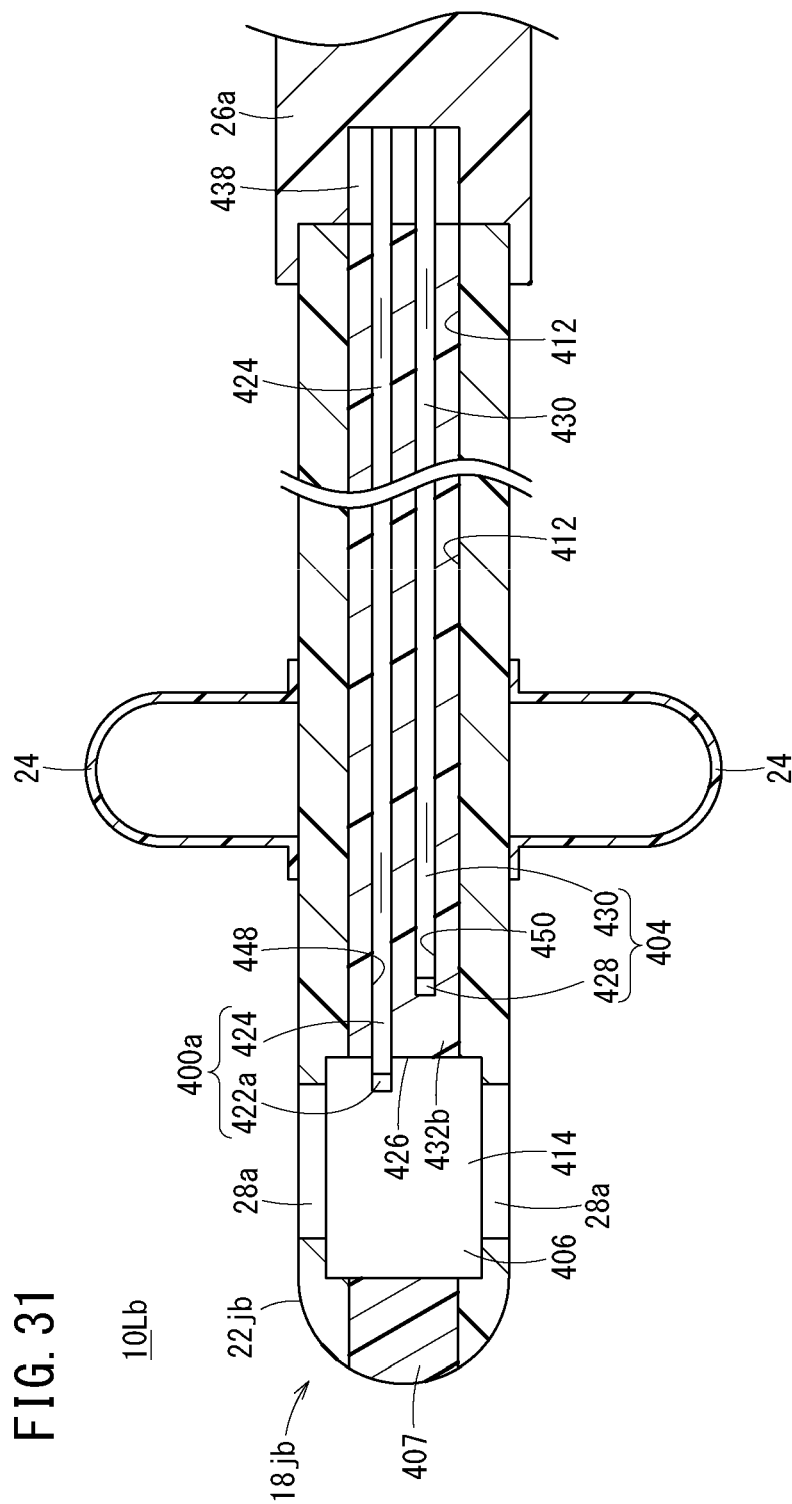
FIG. 31 is a sectional view illustrating a second configuration example of the oxygen measurement device of FIG. 27.

A fixing portion 432b is disposed in a shaft 22jb of a urethral catheter 18jb configuring the oxygen measurement device 10Lb illustrated in FIG. 31, instead of the fixing portion 432a. The fixing portion 432b extends over the entire length to seal the entire sensor lumen 412. The fixing portion 432b is made of a flexible material, inserts the transfer portion 424 into an insertion hole 448 of the fixing portion 432b, and is fixed to the wall surface configuring the sensor lumen 412 in a state where the transfer portion 430 is inserted into a hole 450 of the fixing portion 432b. According to such a configuration, it is possible to effectively suppress the displacement of the oxygen sensor main body 422a and the temperature sensor main body 428 with respect to the shaft 22jb.

Figure 32:
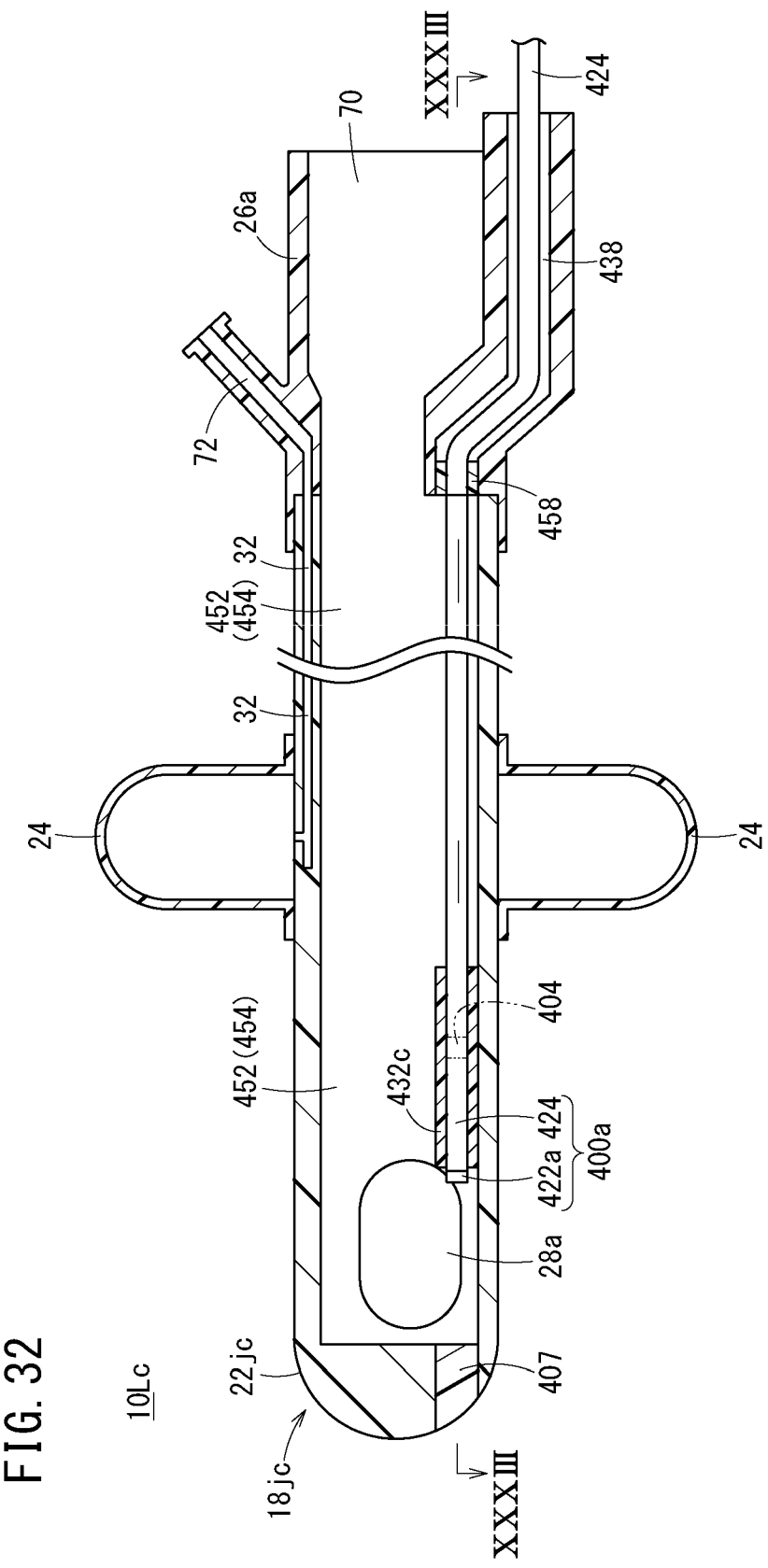
FIG. 32 is a sectional view illustrating a third configuration example of the oxygen measurement device of FIG. 27.
Figure 33:
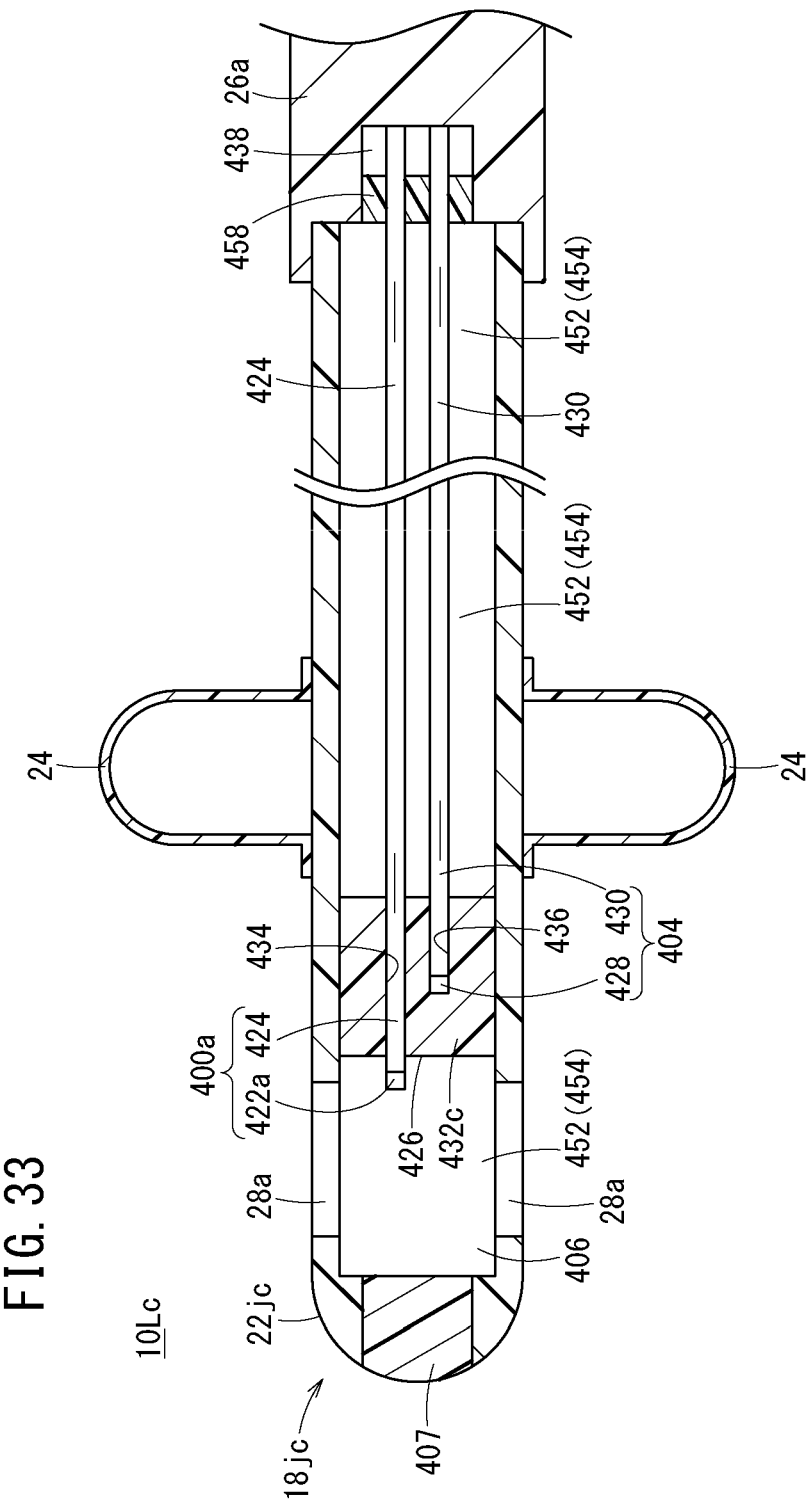
FIG. 33 is a longitudinal sectional view along line XXXIII-XXXIII of FIG. 32.

In a shaft 22jc of a urethral catheter 18jc configuring the oxygen measurement device 10Lc illustrated in FIG. 32 and FIG. 33, the partition wall 408 (refer to FIG. 27) described above is omitted. That is, the lateral lumen 406 as illustrated in FIG. 27 is not disposed, but a urine introduction lumen 452 is disposed in the shaft 22jc. In this case, the urine introduction lumen 452 functions as a urinary passage 454. The oxygen sensor 400a and the temperature sensor 404 are provided in the urinary passage 454. A fixing portion 432c fixing the distal end portion of the transfer portion 424 and the distal end portion of the temperature sensor 404 (the temperature sensor main body 428 and the distal end portion of the transfer portion 430) to a wall surface configuring the urinary passage 454, is disposed in the urinary passage 454. Furthermore, in the urethral catheter 18jc, a seal member 458 for preventing the urine in the urinary passage 454 from being leaked to the outside through the port 438 for disposing a sensor, is provided in the port 438 for disposing a sensor.

In addition, the fixing portion 432c is separated from an inner surface of the urinary passage 454, which faces the fixing portion 432c. In other words, the fixing portion 432c is separated from a portion facing a portion of the inner surface configuring the urinary passage 454, which is in contact with the fixing portion 432c. Accordingly, the discharge of the urine in the urinary passage 454 can be prevented from being inhibited by the fixing portion 432c, and thus, it is possible to smoothly discharge the urine in the urinary passage 454.

Figure 34:
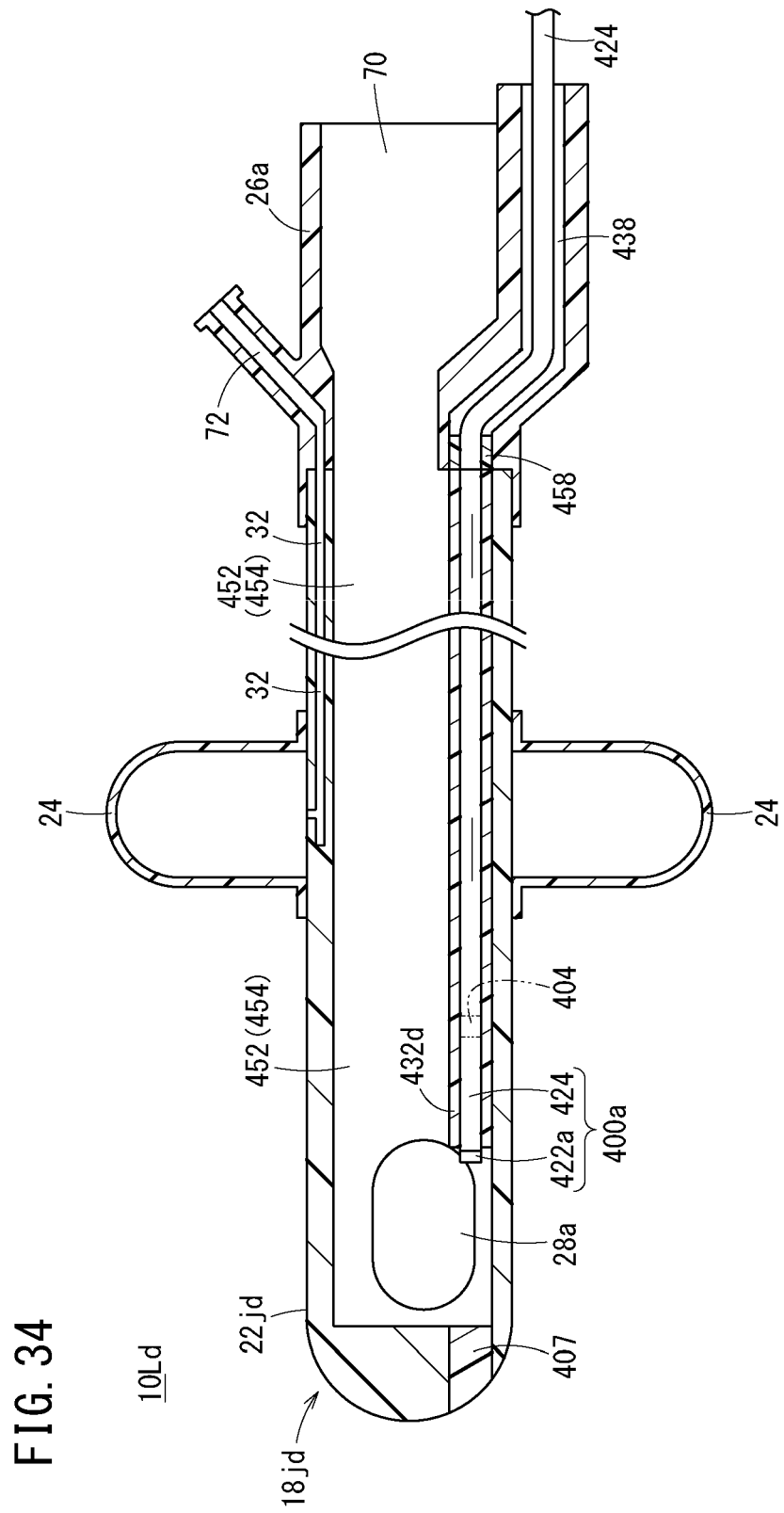
FIG. 34 is a sectional view illustrating a fourth configuration example of the oxygen measurement device of FIG. 27.

In accordance with an embodiment, the fixing portion 432d is disposed in a shaft 22jd of a urethral catheter 18jd configuring the oxygen measurement device 10Ld illustrated in FIG. 34, instead of the fixing portion 432c of the urethral catheter 18jc illustrated in FIG. 32. The fixing portion 432d is disposed to cover the transfer portion 424 and the temperature sensor 404 in the urinary passage 454. In this case, it is possible to more smoothly discharge the urine in the urinary passage 454.

Figure 35:
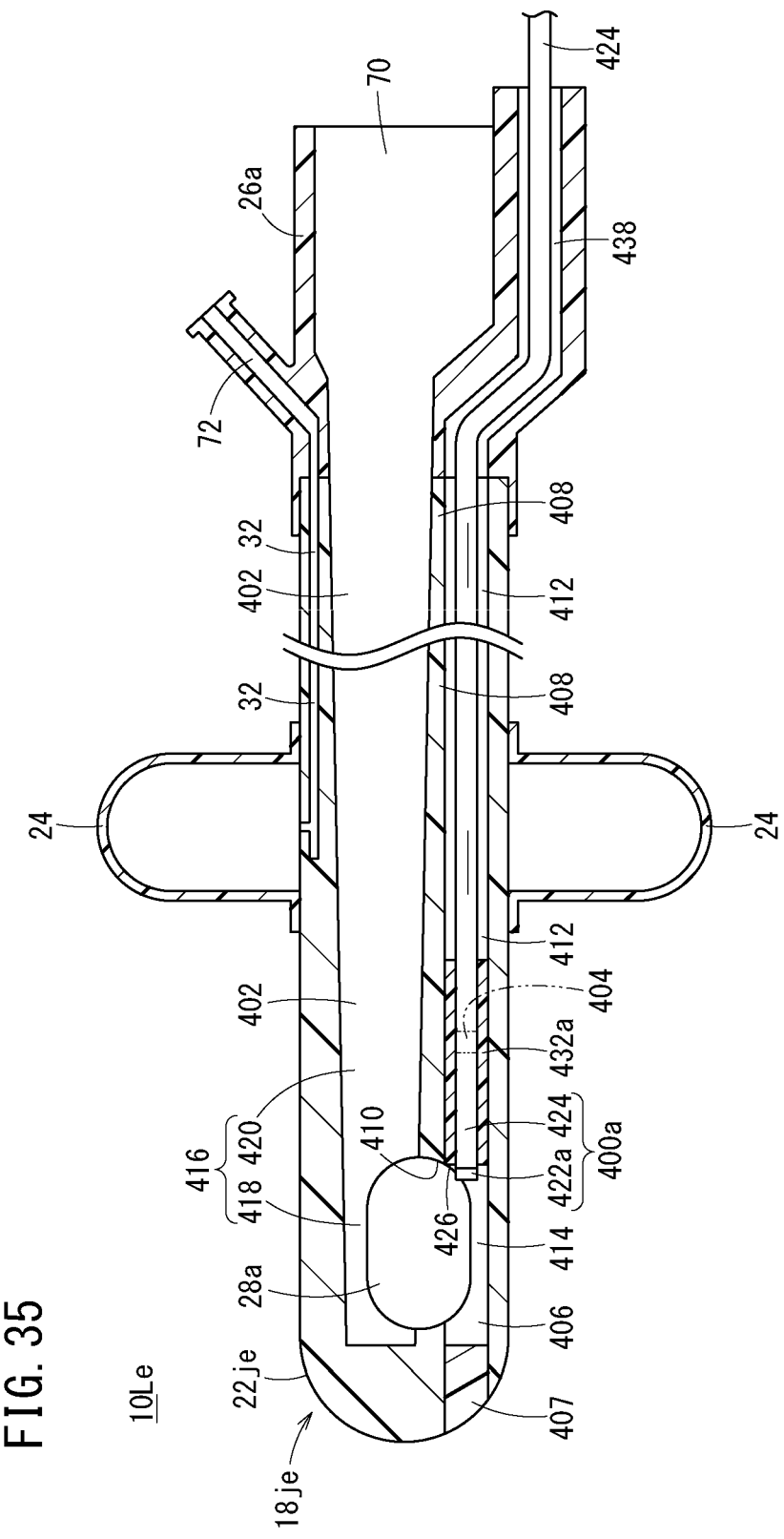
FIG. 35 is a sectional view illustrating a fifth configuration example of the oxygen measurement device of FIG. 27.

In a shaft 22je of a urethral catheter 18je configuring the oxygen measurement device 10Le illustrated in FIG. 35, the flow path sectional area of the second urinary passage portion 420 gradually increases towards the proximal end side. According to such a configuration, it is possible to rather smoothly discharge the urine in the second urinary passage portion 420 towards the proximal end of the shaft 22je. In the urethral catheter 18je, the flow path sectional area of the second urinary passage portion 420 may gradually increase towards the proximal end side. That is, in the second urinary passage portion 420, a flow path sectional area on the proximal end side may be greater than a flow path sectional area on the distal end side.

Figure 36A:
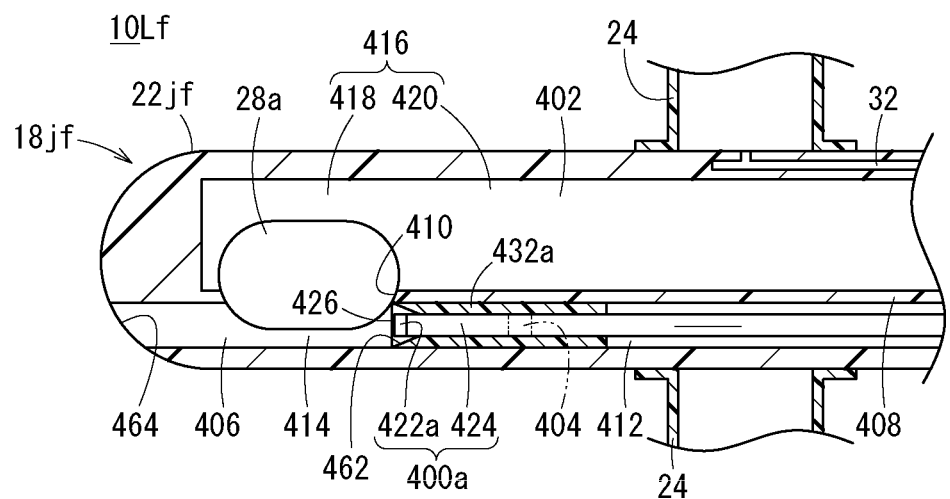
FIG. 36A is a sectional view illustrating a sixth configuration example of the oxygen measurement device of FIG. 27.

In a shaft 22jf of a urethral catheter 18jf configuring the oxygen measurement device 10Lf illustrated in FIG. 36A, a concave portion 462 is disposed on a surface of the fixing portion 432a, which is exposed to the urinary passage 416 side, and the oxygen sensor main body 422a is positioned in the concave portion 462. In addition, in the urethral catheter 18jf, the blocking member 407 described above (refer to FIG. 27) is omitted. For this reason, the urine in the bladder 140 flows from an opening portion 464 of the lateral lumen 406 on the distal end side.

According to such a configuration, it is possible to reliably bring the urine flowing in the urinary passage 416 into contact with the oxygen sensor main body 422a. In the urethral catheter 18jf, the oxygen sensor main body 422a may be positioned on the outside of the concave portion 462 in the urinary passage 416.

Figure 36B:
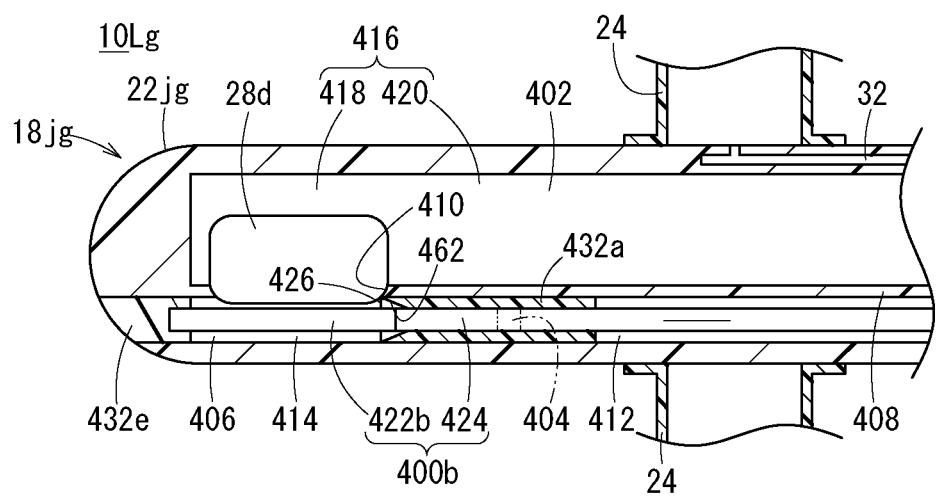
FIG. 36B is a sectional view illustrating a seventh configuration example of the oxygen measurement device of FIG. 27.

An oxygen sensor 400b and a urine introduction port 28d are disposed in a shaft 22jg of a urethral catheter 18jg configuring the oxygen measurement device 10Lg illustrated in FIG. 36B, instead of the oxygen sensor 400a and the urine introduction port 28a illustrated in FIG. 36A. An oxygen sensor main body 422b of the oxygen sensor 400b extends to the distal end side from the urine introduction port 28d.

In addition, a fixing portion 432e fixing a distal end portion of the oxygen sensor main body 422b to an inner surface configuring the distal end portion of the lateral lumen 406, is disposed in the lateral lumen 406. The fixing portion 432e seals the distal end portion of the lateral lumen 406. A urine introduction port 28d is different from the urine introduction port 28a described above in that the urine introduction port 28d is in the shape of a rectangle. According to such a configuration, it is possible to effectively suppress the displacement of the oxygen sensor main body 422b with respect to the shaft 22jg.

Figure 37A:
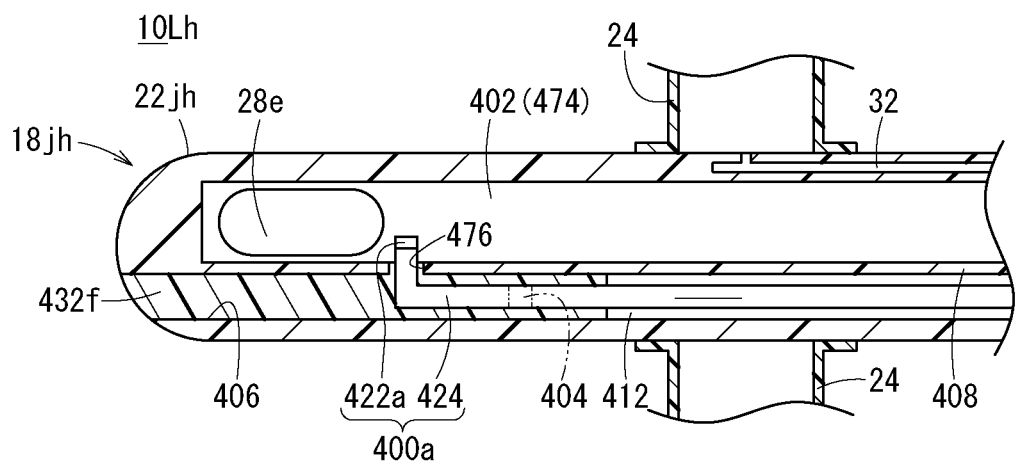
FIG. 37A is a sectional view illustrating an eighth configuration example of the oxygen measurement device of FIG. 27.

A urine introduction port 28e is disposed in a shaft 22jh of a urethral catheter 18jh configuring the oxygen measurement device 10Lh illustrated in FIG. 37A, instead of the urine introduction port 28a illustrated in FIG. 36A. The urine introduction port 28e is in communication only with the urine introduction lumen 402, and does not straddle the lateral lumen 406. In addition, the urine introduction lumen 402 and the lateral lumen 406 are not in communication with each other. For this reason, the entire urine introduction lumen 402 can function as a urinary passage 474, and the urine does not flow into the distal end side from the sensor lumen 412 in the lateral lumen 406.

In addition, an opening portion 476 for positioning the oxygen sensor main body 422a in the urinary passage 474, penetrates through the partition wall 408. That is, the opening portion 476 is directed towards a direction orthogonal to a shaft line direction of the shaft 22jh. The transfer portion 424 is bent to the urinary passage 474 side on the distal end side, and extends to the urinary passage 474 through the opening portion 476. In the urinary passage 474, the oxygen sensor main body 422a is positioned on the proximal end side from the urine introduction port 28e.

A fixing portion 432*f* is disposed in the shaft 22*jh*, instead of the fixing portion 432*a* illustrated in FIG. 36A. The fixing portion 432*f* is disposed to seal the distal end side of the lateral lumen 406 (the distal end side from the sensor lumen 412), and to seal the opening portion 476. Furthermore, the fixing portion 432*f* fixes (i.e., attaches) the distal end portion of the transfer portion 424 and the distal end portion of the temperature sensor 404 to the inner surface configuring the sensor lumen 412.

According to such a configuration, the oxygen sensor main body 422*a* is positioned on the proximal end side from the urine introduction port 28*e*, and thus, even in a case where the shaft 22*jh* is buckled (i.e., bent or twisted) in the position of the urine introduction port 28*e*, it is possible to reliably prevent the oxygen sensor main body 422*a* from being broken. In addition, it is possible to reliably bring the urine flowing in the urinary passage 474 to the proximal end side from the urine introduction port 28*e* into contact with the oxygen sensor main body 422*a*.

Figure 37B:
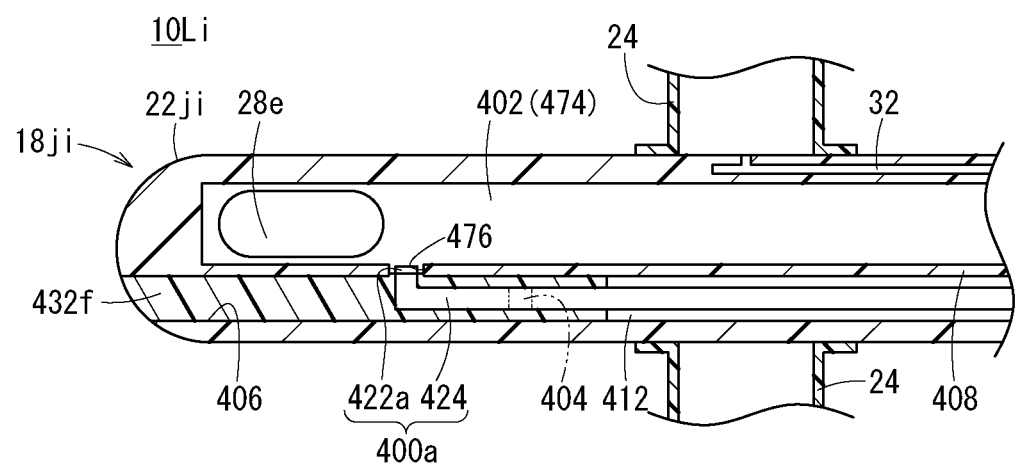
FIG. 37B is a sectional view illustrating a ninth configuration example of the oxygen measurement device of FIG. 27.

In a shaft 22*ji* of a urethral catheter 18*ji* configuring the oxygen measurement device 10Li illustrated in FIG. 37B, the urethral catheter 18*ji* is different from the urethral catheter 18*jh* illustrated in FIG. 37A, only in that the fixing portion 432*f* is configured not to block the opening portion 476, and the oxygen sensor main body 422*a* is positioned in the opening portion 476. According to such a configuration, the same effect as that of the urethral catheter 18*jh* illustrated in FIG. 37A is obtained.

Figure 38A:
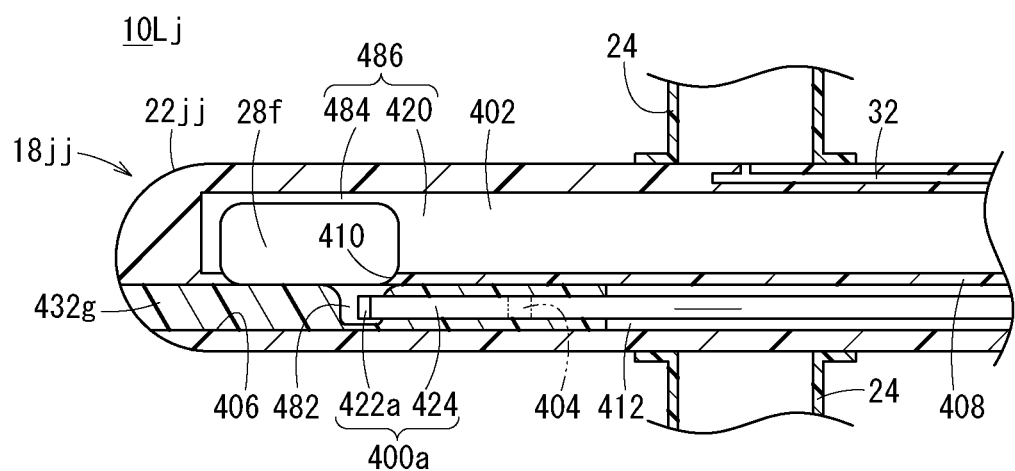
FIG. 38A is a sectional view illustrating a tenth configuration example of the oxygen measurement device of FIG. 27.

A urine introduction port 28*f* and a fixing portion 432*g* are disposed in a shaft 22*jj* of a urethral catheter 18*jj* configuring the oxygen measurement device 10Lj illustrated in FIG. 38A, instead of the urine introduction port 28*a* and the fixing portion 432*a* illustrated in FIG. 36A. The urine introduction port 28*f* is in communication only with the urine introduction lumen 402 and the through hole 410, and does not straddle the lateral lumen 406.

In addition, a concave portion 482 for exposing the oxygen sensor main body 422*a* into the urinary passage 416, is disposed in the fixing portion 432*g*. The concave portion 482 is in communication with the urine introduction port 28*f* through the through hole 410.

In the shaft 22*jj*, the distal end side of the urine introduction lumen 402, the through hole 410, and the concave portion 482 function as a first urinary passage portion 484, and the proximal end side of the urine introduction lumen 402 from the through hole 410 functions as a second urinary passage portion 420. Then, the first urinary passage portion 484 and the second urinary passage portion 420 form a urinary passage 486. Furthermore, the fixing portion 432*g* fixes (i.e., attaches) the distal end portion of the transfer portion 424 and the distal end portion of the temperature sensor 404 to the inner surface configuring the sensor lumen 412. According to such a configuration, the oxygen sensor main body 422*a* can be brought into contact with the urine flowing in the urinary passage 486.

Figure 38B:
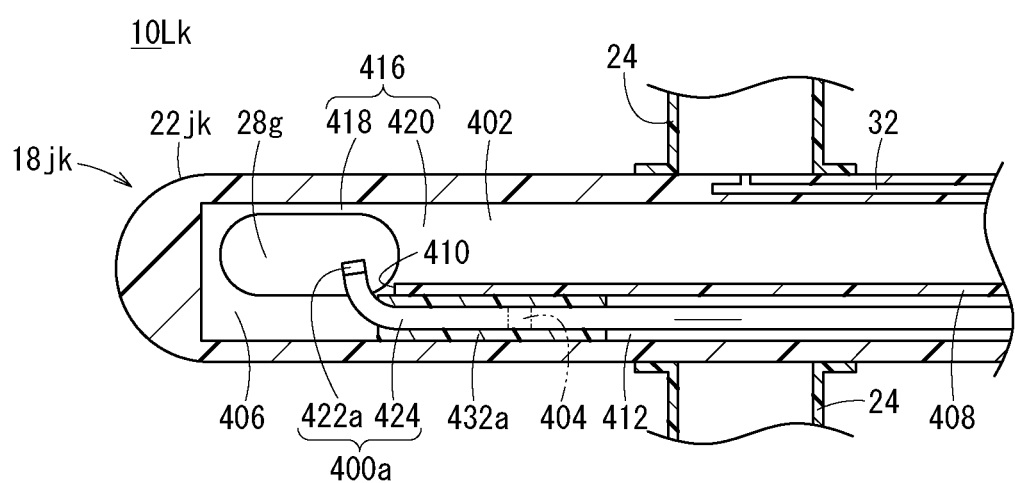
FIG. 38B is a sectional view illustrating an eleventh configuration example of the oxygen measurement device of FIG. 27.

A urine introduction port 28*g* is disposed in a shaft 22*jk* of a urethral catheter 18*jk* configuring the oxygen measurement device 10Lk illustrated in FIG. 38B, instead of the urine introduction port 28*a* illustrated in FIG. 27. The urine introduction port 28*g* straddles the urine introduction lumen 402 and the through hole 410, and is not positioned on the inner surface configuring the lateral lumen 406. In addition, the distal end of the lateral lumen 406 is in the same position as that of the distal end of the urine introduction lumen 402, in a shaft line direction of the shaft 22*jk*. That is, the lateral lumen 406 does not penetrate through the distal end of the shaft 22*jk*.

The transfer portion 424 is bent to the urine introduction lumen 402 side in the urinary passage 416, and the oxygen sensor main body 422*a* is positioned in the urine introduction lumen 402. Specifically, the oxygen sensor main body 422*a* is adjacent to the urine introduction port 28*g* in a direction orthogonal to the shaft line direction of the shaft 22*jk*. Furthermore, the fixing portion 432*a* extends to the distal end side from the partition wall 408. According to such a configuration, the oxygen sensor 400*a* can be brought into contact with the urine flowing in the urinary passage 416.

Figure 39A:
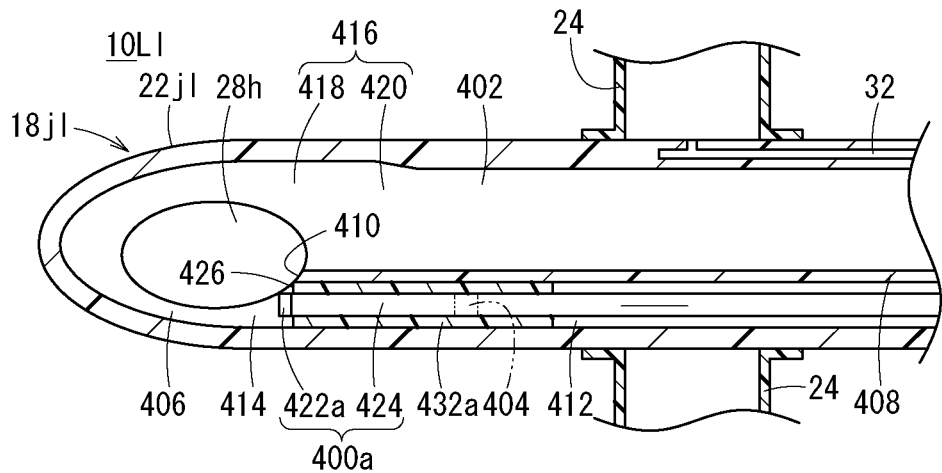
FIG. 39A is a sectional view illustrating a twelfth configuration example of the oxygen measurement device of FIG. 27.

In a shaft 22*jl* of a urethral catheter 18*jl* configuring the oxygen measurement device 10L1 illustrated in FIG. 39A, the shape of a distal end portion is different from the shape of the distal end portion of the shaft 22*j* described above. The curvature of the distal end surface of the shaft 22*jl* is greater than the curvature of the distal end surface of the shaft 22*jl*. In addition, an elliptical urine introduction port 28*h* is disposed in the shaft 22*jl*, instead of the urine introduction port 28*a* illustrated in FIG. 27. According to such a configuration, the oxygen sensor 400*a* can be brought into contact with the urine flowing in the urinary passage 416.

Figure 39B:
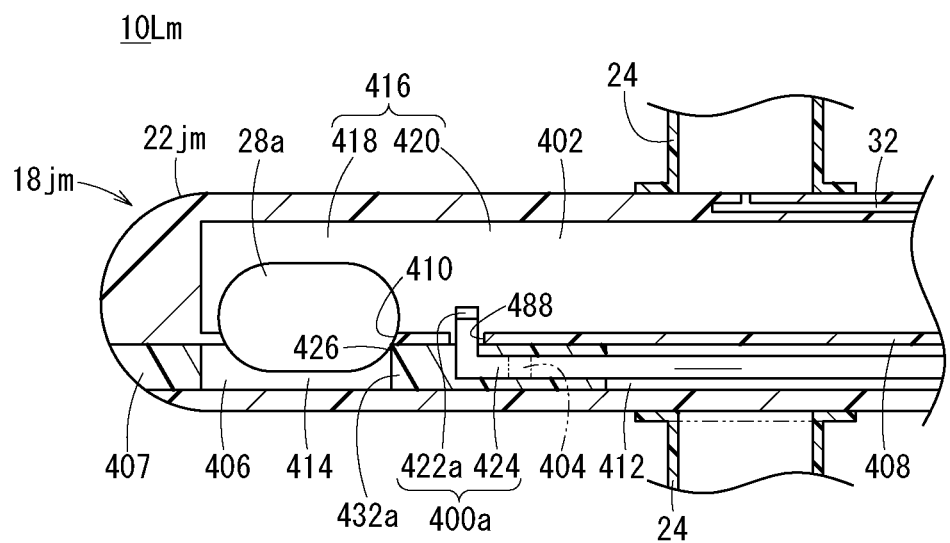
FIG. 39B is a sectional view illustrating a thirteenth configuration example of the oxygen measurement device of FIG. 27.

In a shaft 22*jm* of a urethral catheter 18*jm* configuring the oxygen measurement device 10Lm illustrated in FIG. 39B, an opening portion 488 for positioning the oxygen sensor main body 422*a* in a urine introduction lumen 402 is disposed in a partition wall 408. That is, the opening portion 488 is directed towards a direction orthogonal to a shaft line direction of the shaft 22*jm*. The transfer portion 424 is bent to the urinary passage 416 side on the distal end side, and extends to the urinary passage 416 through the opening portion 488. For this reason, the oxygen sensor main body 422*a* is positioned on the proximal end side from the urine introduction port 28*a*, in the second urinary passage portion 420.

According to such a configuration, even in a case where the urinated volume is comparatively small, it is possible to reliably bring the urine flowing in the urinary passage 416 into contact with the oxygen sensor main body 422*a*.

Figure 40A:
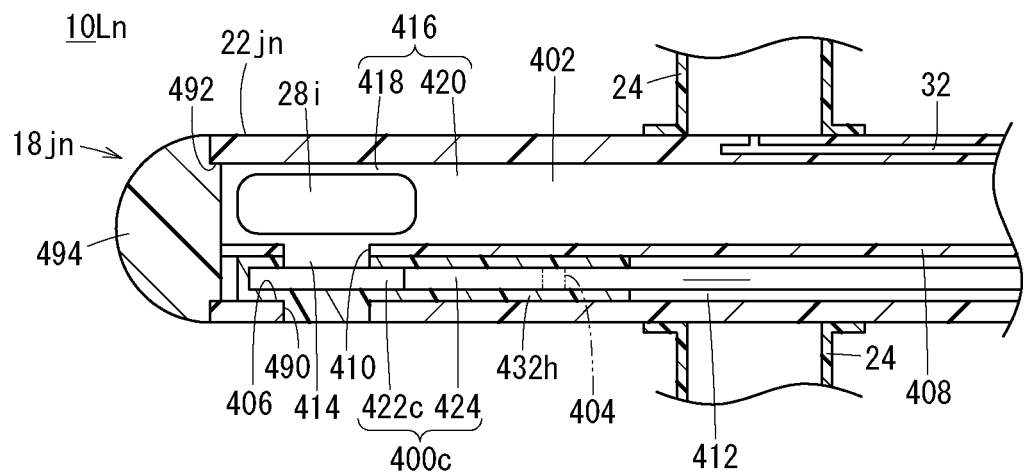
FIG. 40A is a sectional view illustrating a fourteenth configuration example of the oxygen measurement device of FIG. 27.

In a shaft 22*jn* of a urethral catheter 18*jn* configuring the oxygen measurement device 10Ln illustrated in FIG. 40A, a distal end is opened, and a hole 490 (a through hole) is disposed on an outer circumference surface on the distal end side. An opening portion 492 on the distal end of the shaft 22*jn* is blocked by a blocking member 494. The blocking member 494 may be integrally disposed in the shaft 22*jn*. The hole 490 faces the through hole 410.

In addition, an oxygen sensor 400*c*, a urine introduction port 28*i*, and a fixing portion 432*h* (an adhesive agent) are disposed in the shaft 22*jn*, instead of the oxygen sensor 400*a*, the urine introduction port 28*a*, and the fixing portion 432*a*, illustrated in FIG. 27. An oxygen sensor main body 422*c* of the oxygen sensor 400*c* extends to a distal end side of the urine introduction port 28*i* along a shaft line (i.e., axial) direction of the shaft 22*jn*. The urine introduction port 28*i* is in communication with the urine introduction lumen 402, and does not straddle the through hole 410 and the lateral lumen 406. That is, the urine introduction port 28*i* is in communication with the lateral urine introduction lumen 414 through the urine introduction lumen 402 and the through hole 410. Furthermore, the urine introduction port 28*i* extends to the distal end side and the proximal end side from the through hole 410. In other words, the through hole 410 and the hole 490 are positioned in a direction orthogonal to the shaft line direction of the shaft 22*jn* with respect to the urine introduction port 28*i*.

The fixing portion 432*h* fixes the oxygen sensor 400*c* to the shaft 22*jn*, in a state of blocking the hole 490. Specifically, the fixing portion 432*h* is disposed in the distal end portion and the proximal end portion of the oxygen sensor main body 422*c*, and the transfer portion 424. Accordingly, it is possible to effectively hold the oxygen sensor main body 422*c* in the lateral urine introduction lumen 414. A portion of an intermediate portion of the oxygen sensor main body 422*c* in an extending direction, which faces the through hole 410, is exposed to the lateral urine introduction lumen 414. Furthermore, the fixing portion 432*h* may be disposed only one of the distal end portion and the proximal end portion of the oxygen sensor main body 422*c*.

According to such a configuration, it is possible to easily dispose the fixing portion 432*h* in the lateral lumen 406 through the hole 490 disposed on the outer circumference surface of the shaft 22*jn*. Accordingly, it is possible to reduce manufacturing man-hours of the urethral catheter 18*jn*. In addition, the hole 490 is blocked by the fixing portion 432*h*, and thus, the urine flowing into the urinary passage 416 from the urine introduction port 28*i* is not leaked to the outside of the urethral catheter 18*jn* through the hole 490.

Figure 40B:
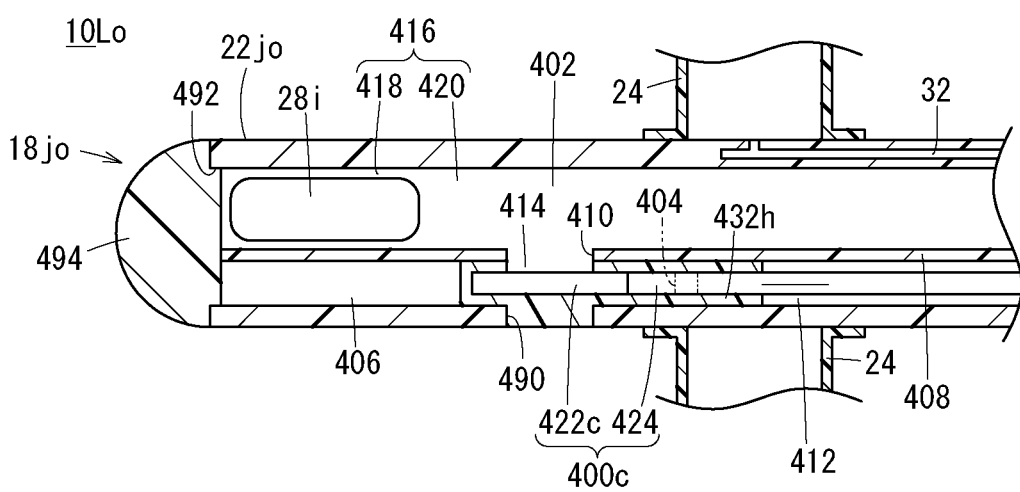
FIG. 40B is a sectional view illustrating a fifteenth configuration example of the oxygen measurement device of FIG. 27.

In a shaft 22*jo* of a urethral catheter 18*jo* configuring the oxygen measurement device 10Lo illustrated in FIG. 40B, the urethral catheter 18*jo* is different from the urethral catheter 18*jn* illustrated in FIG. 40A in that the through hole 410 and the hole 490 are positioned on the proximal end side from the urine introduction port 28*i*. In addition, in a shaft line direction of the shaft 22*jo*, the distal end of the oxygen sensor main body 422*c* is positioned on the proximal end of the urine introduction port 28*i*. According to such a configuration, the same effect as that of the urethral catheter 18*jn* illustrated in FIG. 40A is obtained.

Figure 41A:
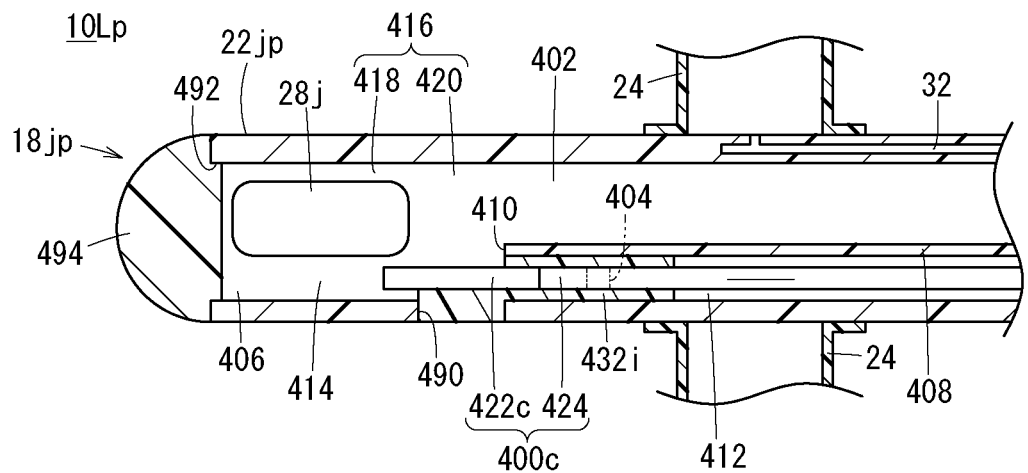
FIG. 41A is a sectional view illustrating a sixteenth configuration example of the oxygen measurement device of FIG. 27.

In a shaft 22*jp* of a urethral catheter 18*jp* configuring the oxygen measurement device 10Lp illustrated in FIG. 41A, the urethral catheter 18*jp* is different from the urethral catheter 18*jn* illustrated in FIG. 40A in that a urine introduction port 28*j* and a fixing portion 432*i* (an adhesive agent) are disposed instead of the urine introduction port 28*i* and the fixing portion 432*h*. The urine introduction port 28*j* straddles the urine introduction lumen 402 and the through hole 410, and does not straddle the lateral lumen 406. In addition, the through hole 410 extends up to a proximal end side of the urine introduction port 28*j*, and the hole 490 is positioned on the proximal end side from the urine introduction port 28*j*. In addition, in a shaft line direction of the shaft 22*jp*, the distal end of the oxygen sensor main body 422*c* is positioned on the proximal end side of the urine introduction port 28*j*.

The fixing portion 432*i* blocks the hole 490, and is disposed in the proximal end portion and the transfer portion 424 of the oxygen sensor main body 422*c*. According to such a configuration, the same effect as that of the urethral catheter 18*jn* illustrated in FIG. 40A is obtained.

Figure 41B:
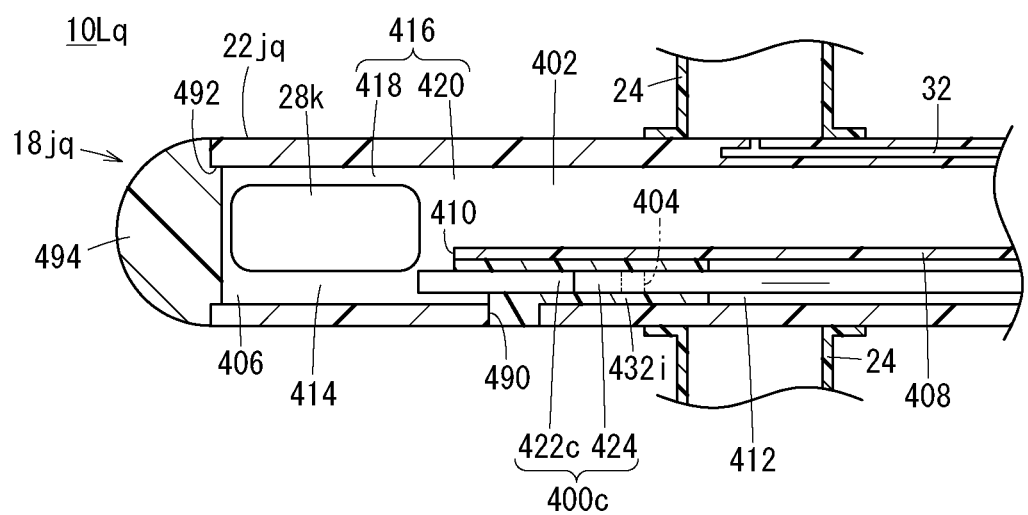
FIG. 41B is a sectional view illustrating a seventeenth configuration example of the oxygen measurement device of FIG. 27.

In a shaft 22*jq* of a urethral catheter 18*jq* configuring the oxygen measurement device 10Lq illustrated in FIG. 41B, the urethral catheter 18*jq* is different from the urethral catheter 18*jp* illustrated in FIG. 41A in that a urine introduction port 28*k* is disposed instead of the urine introduction port 28*j*. The urine introduction port 28*k* straddles the urine introduction lumen 402, the through hole 410, and the lateral urine introduction lumen 414. In addition, in a shaft line direction of the shaft 22*jq*, the distal end of the oxygen sensor main body 422*c* is positioned on a proximal end of the urine introduction port 28*k*. The hole 490 is positioned on the proximal end side from the urine introduction port 28*k* and the through hole 410. According to such a configuration, the same effect as that of the urethral catheter 18*jn* illustrated in FIG. 40A is obtained.

Figure 42A:
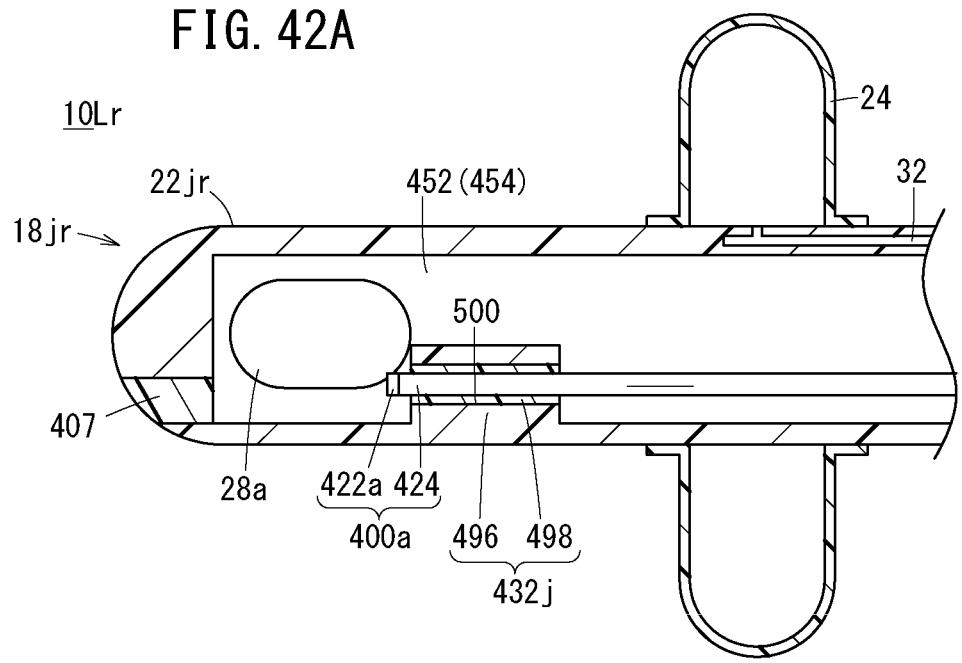
FIG. 42A is a sectional view illustrating an eighteenth configuration example of the oxygen measurement device of FIG. 27.

In a shaft 22*jr* of a urethral catheter 18*jr* configuring the oxygen measurement device 10Lr illustrated in FIG. 42A, the urethral catheter 18*jr* is different from the urethral catheter 18*jc* illustrated in FIG. 32 in that a fixing portion 432*j* is disposed instead of the fixing portion 432*c*. The fixing portion 432*j* includes a support portion 496 protruding from an inner surface of the urine introduction lumen 452, and an engagement portion 498 (an attachment portion) for attaching the transfer portion 424 to the support portion 496. An insertion hole 500 into which the transfer portion 424 is inserted, is disposed in the support portion 496.

The engagement portion 498 is attached to an outer circumference surface of the transfer portion 424, and is attached to an inner surface configuring the insertion hole 500. Accordingly, the oxygen sensor 400*a* is reliably fixed (i.e., attached) to the shaft 22*jr*. That is, the engagement portion 498 constantly holds a distance between the oxygen sensor main body 422*a* and the support portion 496.

Figure 42B:
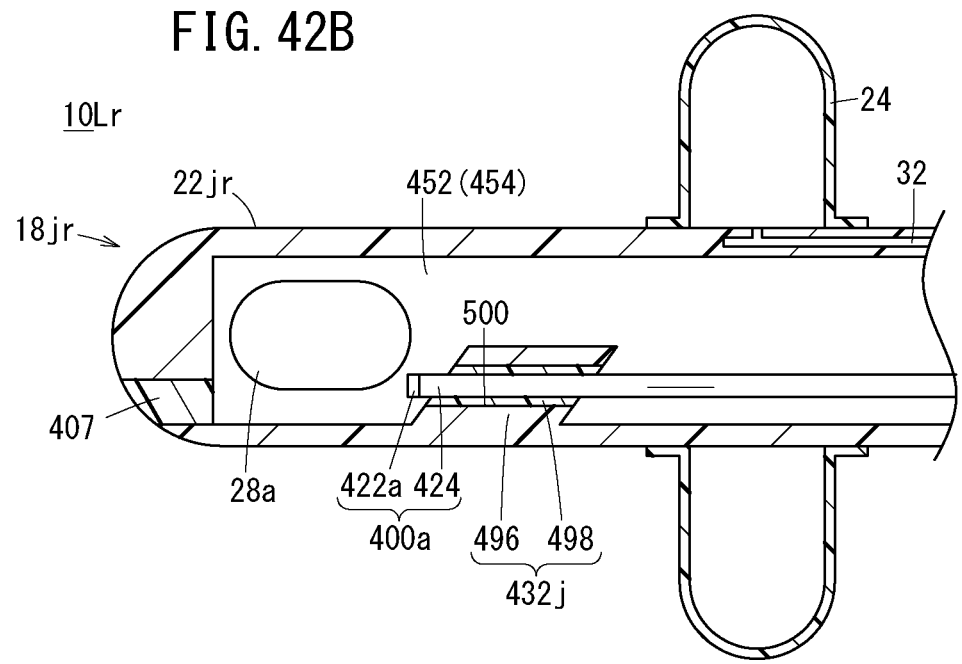
FIG. 42B is a sectional view illustrating a nineteenth configuration example of the oxygen measurement device of FIG. 27.

The support portion 496 may be a rigid body, or may have flexibility. In a case where the support portion 496 has flexibility, as illustrated in FIG. 42B, for example, the support portion 496 can be elastically deformed even in a case where the transfer portion 424 is stretched to the proximal end side, and thus, it is possible to prevent the oxygen sensor 400*a* from being broken. In addition, in this case, the support portion 496 and the engagement portion 498 may be relatively moved in a shaft line direction of the shaft 22*jr*. The support portion 496 and the engagement portion 498 may be made of the same material, or may be made of materials different from each other.

Figure 43A:
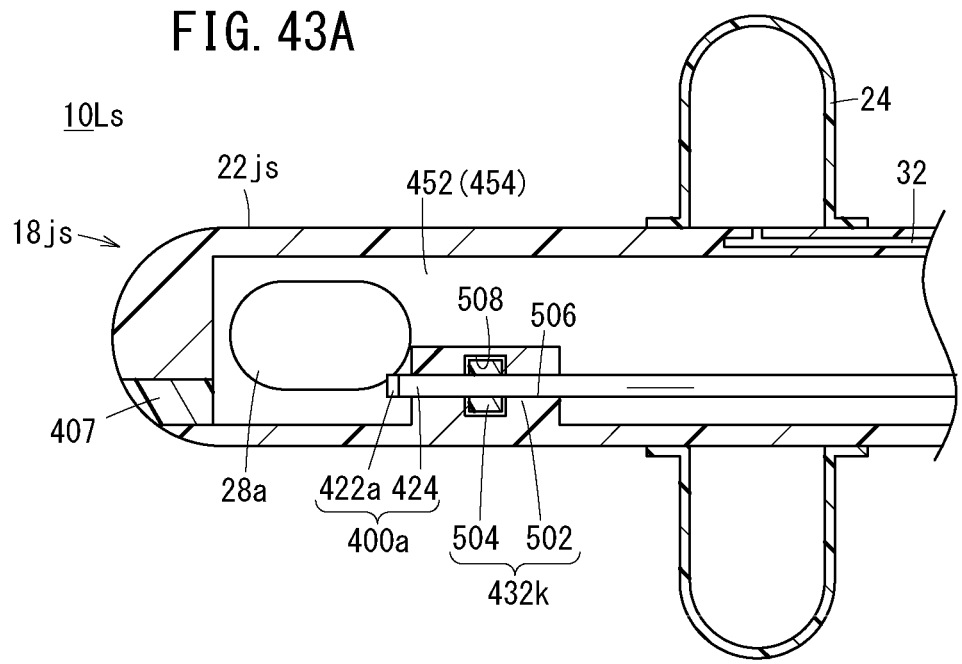
FIG. 43A is a sectional view illustrating a twentieth configuration example of the oxygen measurement device of FIG. 27.

In a shaft 22*js* of a urethral catheter 18*js* configuring the oxygen measurement device 10Ls illustrated in FIG. 43A, the urethral catheter 18*js* is different from the urethral catheter 18*jr* illustrated in FIG. 42A in that a fixing portion 432*k* is disposed instead of the fixing portion 432*j*. The fixing portion 432*k* includes a support portion 502 protruding from the inner surface of the urine introduction lumen 452, and an engagement portion 504 for engaging the transfer portion 424 with the support portion 502. An insertion hole 506 into which the transfer portion 424 is inserted, is disposed in the support portion 502. A concave portion 508 in which the engagement portion 504 is provided, is disposed on an inner surface configuring the insertion hole 506. In such a configuration, it is possible to fix the oxygen sensor 400*a* to the shaft 22*js*. Furthermore, in an illustrated example, the engagement portion 504 is not attached to the inner surface of the concave portion 508, but may be attached to the inner surface of the concave portion 508.

Figure 43B:
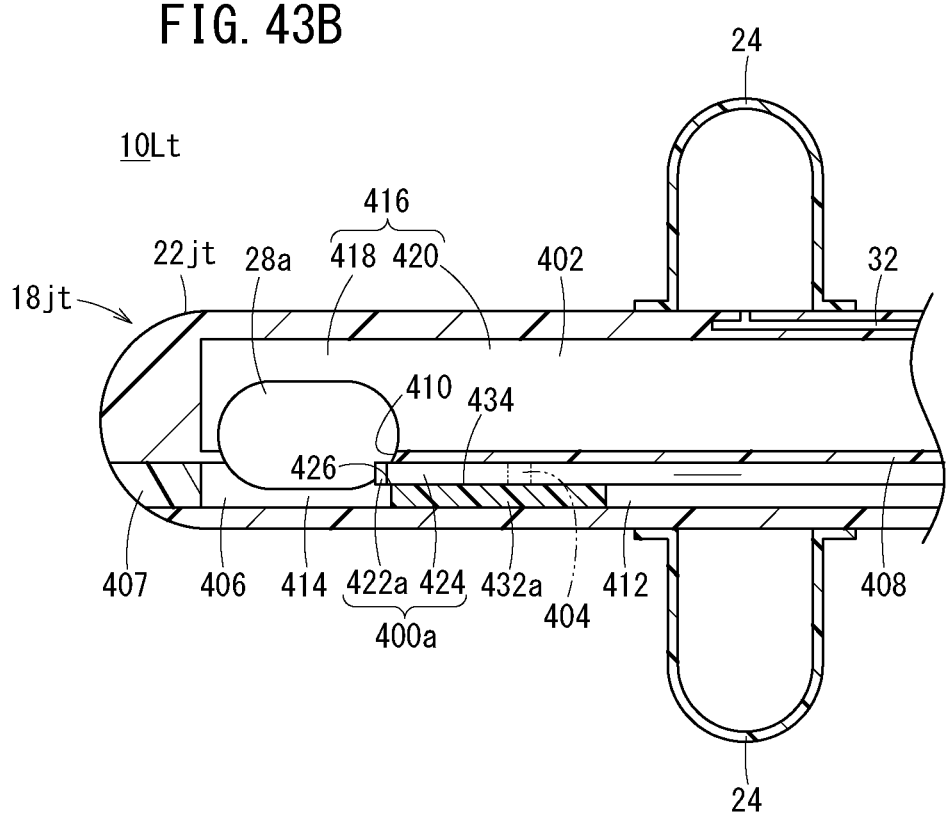
FIG. 43B is a sectional view illustrating a twenty-first configuration example of the oxygen measurement device of FIG. 27.

In a shaft 22*jt* of a urethral catheter 18*jt* configuring the oxygen measurement device 10Lt illustrated in FIG. 43B, the urethral catheter 18*jt* is different from the urethral catheter 18*j* illustrated in FIG. 27 in that the insertion hole 434 of the fixing portion 432*a* is positioned on the urine introduction lumen 402 side. In other words, the insertion hole 434 is disposed on an outer surface of the fixing portion 432*a* on the urine introduction lumen 402 side. That is, in the inner surface configuring the sensor lumen 412, a distal end surface on the urine introduction lumen 402 side (a distal end surface of the partition wall 408 on the sensor lumen 412 side) is positioned in the insertion hole 434. For this reason, the transfer portion 424 is in contact with the distal end surface. Accordingly, it is possible to position the oxygen sensor main body 422*a* on the urine introduction lumen 402 side.

Figure 44:
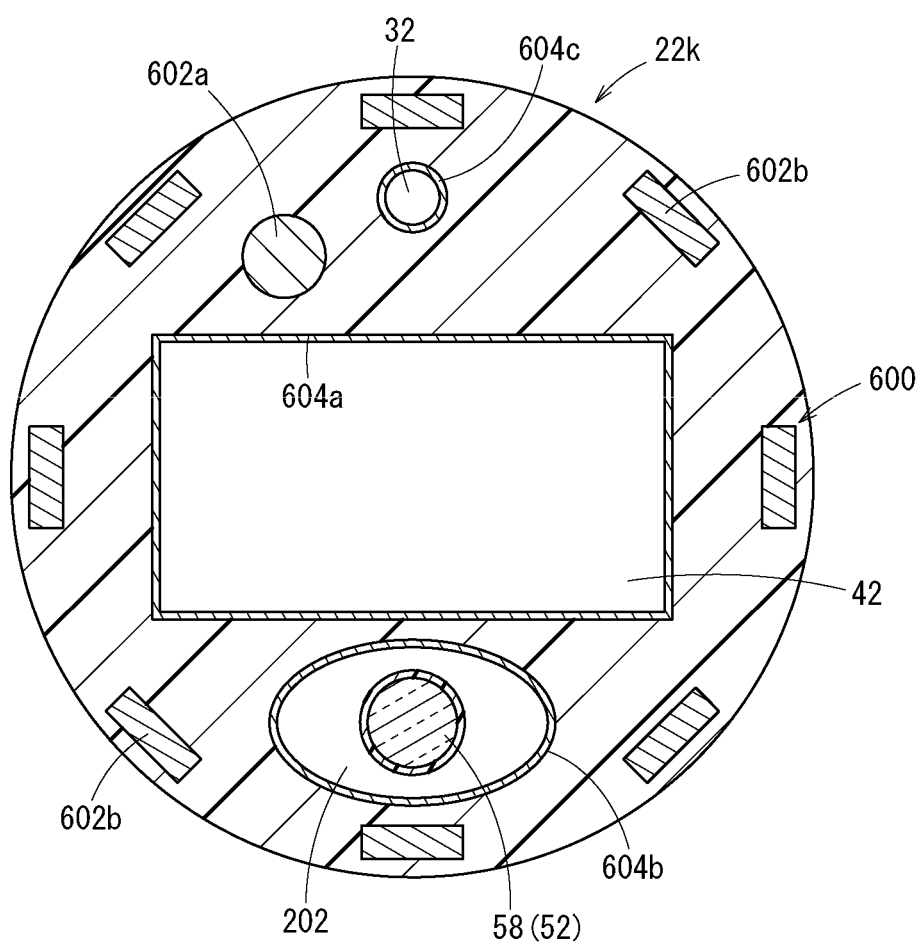
FIG. 44 is a transverse sectional view illustrating a configuration example of a shaft.

The disclosure is not limited to the configurations described above. One or three or more urine introduction ports 28a to 28k may be included, and the opening positions of the one or three or more urine introduction portion 28a to 28k may not face each other, or may be in the distal end portions of the blocking portions 23a to 23e. The oxygen measurement devices 10A to 10J may include a shaft 22k illustrated in FIG. 44. As illustrated in FIG. 44, a hard member 600 configured of a material harder than the material configuring the shaft 22k, may be disposed in the shaft 22k. The hard member 600, for example, is configured of a metal, plastic, a fiber, or the like. The hard member 600 includes embedded hard portions 602a and 602b which are embedded in a wall portion of the shaft 22k, a wall surface hard portion 604a which is disposed on the wall surface configuring the urine introduction lumen 42, a wall surface hard portion 604b which is disposed on a wall surface configuring the sensor lumen 202, and a wall surface hard portion 604c which is disposed on a wall surface configuring the dilation lumen 32. The embedded hard portions 602a and 602b linearly extend. Concavities and convexities may be formed or may not be formed on outer surfaces of the embedded hard portions 602a and 602b and the wall surface hard portions 604a to 604c. In addition, the embedded hard portions 602a and 602b and the wall surface hard portions 604a to 604c may be a strip-like member in which a plurality of hole portions are formed. Further, the embedded hard portions 602a and 602b may be configured into the shape of a mesh (a net), or may be a braided matter in which fibers or the like are tightly combined. At least one of the embedded hard portions 602a and 602b and the wall surface hard portions 604a to 604c may be disposed in the shaft 22k. According to such a configuration, the expansion and contraction of the shaft 22k can be suppressed by the hard member 600, and thus, it is possible to suppress positional displacement between the oxygen sensor main bodies 50a to 50h, 50ha, and 50hb, and the optical fiber 58, according to the expansion and contraction of the shaft 22k.

Figure 45A:
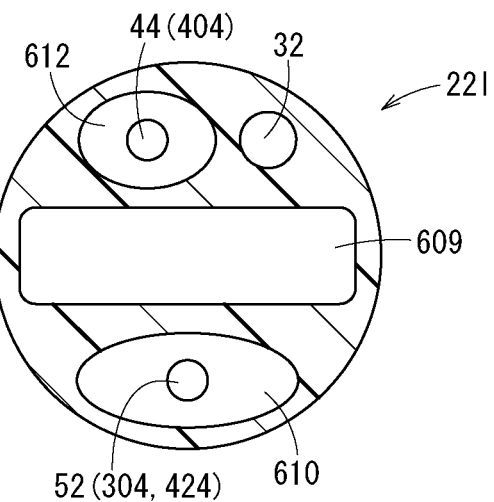
FIG. 45A is a sectional view illustrating a first configuration example of the shaft.

The oxygen measurement devices 10A to 10L, and 10La to 10Lt may include a shaft 22l illustrated in FIG. 45A. As illustrated in FIG. 45A, a urine introduction lumen 609 is disposed in the central portion of the shaft 22l. A first sensor lumen 610 in which the transfer portion 52, and the transfer portion 304 or the transfer portion 424 are provided, is disposed on one side of the urine introduction lumen 609 in the shaft 22l.

A second sensor lumen 612 in which the temperature sensor 44 or the temperature sensor 404 is provided, and the dilation lumen 32 adjacent to the second sensor lumen 612, are disposed on the other side of the urine introduction lumen 609 in the shaft 22l (on a side opposite to the first sensor lumen 610). As described above, in a case of disposing the first sensor lumen 610 and the second sensor lumen 612, it is possible to improve a freedom degree of disposing the sensor.

Figure 45B:
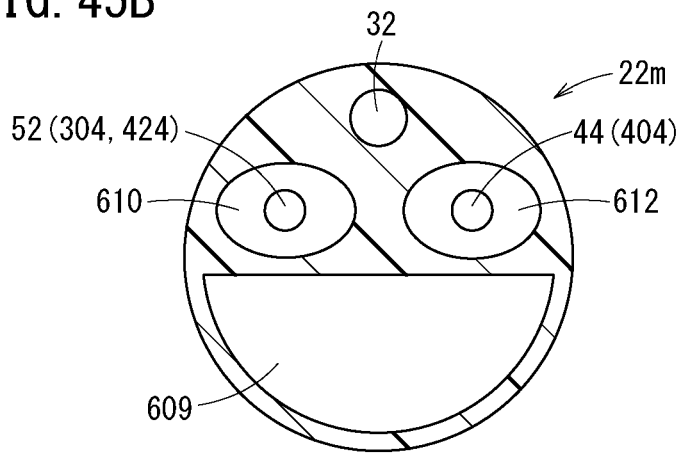
FIG. 45B is a sectional view illustrating a second configuration example of the shaft.

The oxygen measurement devices 10A to 10L, and 10La to 10Lt may include a shaft 22m illustrated in FIG. 45B. As illustrated in FIG. 45B, in the shaft 22m, the urine introduction lumen 609 of which a transverse sectional surface is in the shape of a semicircle, is disposed in a position displaced from the center of the shaft 22m. In addition, the first sensor lumen 610 and the second sensor lumen 612 are disposed on the same side with respect to the urine introduction lumen 609. The first sensor lumen 610 and the second sensor lumen 612 are juxtaposed (i.e., placed side by side) with a width direction of the urine introduction lumen 609 (an extending direction of a string of a transverse sectional surface of the urine introduction lumen 609, and a left and right direction of FIG. 27B). In addition, the dilation lumen 32 is disposed on a side opposite to the urine introduction lumen 609 with respect to the first sensor lumen 610 and the second sensor lumen 612.

Figure 45C:
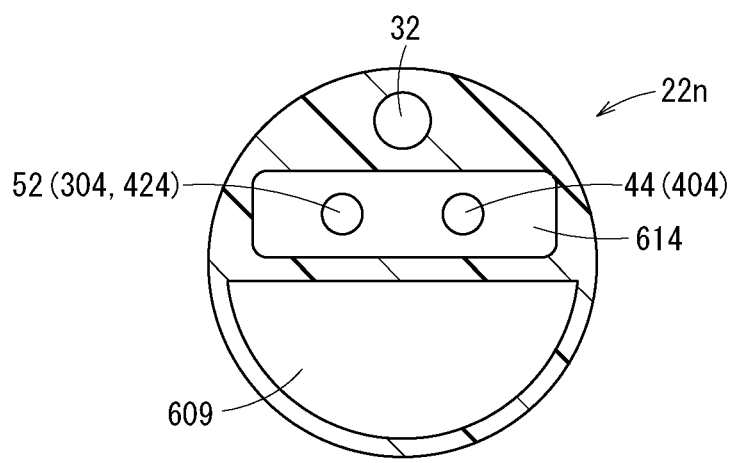
FIG. 45C is a sectional view illustrating a third configuration example of the shaft.

The oxygen measurement devices 10A to 10L, and 10La to 10Lt may include a shaft 22n illustrated in FIG. 45C. As illustrated in FIG. 45C, the shaft 22n is different from the shaft 22m illustrated in FIG. 45B in that one sensor lumen 614 is disposed instead of the first sensor lumen 610 and the second sensor lumen 612. In this case, in the sensor lumen 614, the transfer portion 52, the transfer portion 304 or the transfer portion 424, and the temperature sensor 44 or the temperature sensor 404 are juxtaposed (i.e., placed side by side) with each other.

The oxygen measurement devices 10A to 10L, and 10La to 10Lt may include a temperature sensor capable of detecting the temperature of the urine on the proximal end side of the urethral catheters 18a to 18j, and 18ja to 18jt, in addition to the temperature sensors 44 and 404 disposed in the distal end portion of the urethral catheters 18a to 18j, and 18ja to 18jt. The oxygen measurement devices 10A to 10L, and 10La to 10Lt may include a pressure sensor measuring a pressure in the vicinity of the distal ends of the urethral catheters 18a to 18j, and 18ja to 18jt. The pressure sensor outputs an electrical signal or an optical signal to the monitoring system 16.

The monitor main body portion 94 may be configured to be capable of acquiring time, an atmospheric pressure in the vicinity of the monitor main body portion 94, humidity in the vicinity of the monitor main body portion 94, and a temperature in the vicinity of the monitor main body portion 94. Furthermore, the time includes the current time, and an elapsed time from a certain timing (i.e., a set time). The monitor main body portion 94 is configured to be capable of reading out and reflecting an initial (at the time of being manufactured) calibration value unique to each of the sensors. An input method of the calibration value may be scanning of one-dimensional or two-dimensional bar code, or may be direct input from the monitor 114. In addition, the calibration value may be held in a signal output unit of the urethral catheters 18a to 18j, and 18ja to 18jt, and the monitoring system 16 may be automatically read in by being connected to the urethral catheters 18a to 18j, and 18ja to 18jt.

In the oxygen measurement systems 12 and 12A, an operation may be confirmed before being used. In this case, it is confirmed that an output value from each of the sensors of the oxygen measurement devices 10A to 10L, and 10La to 10Lt is within a normal operation range. Specifically, a reference value calculated from the temperature, the humidity, and the atmospheric pressure in the vicinity of the monitor main body portion 94, is compared with the output value from each of the sensors of the oxygen measurement devices 10A to 10L, and 10La to 10Lt. Then, the control unit 116 of the monitor main body portion 94 determines whether or not the output value from each of the sensors of the oxygen measurement devices 10A to 10L, and 10La to 10Lt is within a normal range, and notifies the determination result. Furthermore, the confirmation that the output value from each of the sensors of the oxygen measurement devices 10A to 10L, and 10La to 10Lt is within the normal range, may be performed by acquiring the output value from each of the sensors by using a reference solution or reference gas, and by comparing the output value with the reference value.

The monitor main body portion 94 may notify various physical amounts (the oxygen partial pressure, the temperature in the bladder, the urinary volume, and the like), on the basis of the output value from each of the sensors of the oxygen measurement devices 10A to 10L, and 10La to 10Lt. Specifically, the monitor main body portion 94 is capable of notifying the physical amount by a numerical value, a bar graph, a dial gauge, a level meter, and a color. In addition, the monitor main body portion 94 is capable of displaying the transition of the physical amount on the monitor 114, by up-down arrows, various graphs (a line graph and the like), and color change progress display.

There is a temporal difference until a change in the bladder 140 appears as a change in the flow rate of the urine in the oxygen measurement devices 10A to 10L, and 10La to 10Lt. For this reason, the monitor main body portion 94 may display a delay time until the change in the bladder 140 appears as the output value of each of the sensors of the oxygen measurement devices 10A to 10L, and 10La to 10Lt, on the monitor 114.

In the monitor main body portion 94, the user is capable of setting a predetermined condition. The monitor main body portion 94 may determine whether or not a state of satisfying a set condition has progressed for a set time, and may notify the determination result. That is, for example, in a case where a set urinary volume is not capable of being urinated, the monitor main body portion 94 may perform notification in a case where the state of satisfying the set condition (a low output state of the sensor, a state where the temperature in the bladder is lower than a set temperature, and the like) is continued for the set time or longer.

The monitor main body portion 94 may determine that a set change occurs, and may notify the determination result. That is, for example, in a case where the change rate of the flow rate of the urine is greater than a set change rate, the monitor main body portion 94 may perform notification in a case where a change width of a measurement temperature of the urine is greater than a set change width.

The monitor main body portion 94 may have a function of holding a program in the monitor main body portion 94, and may be configured to be capable of updating the program by receiving update information from the outside. In this case, the monitor main body portion 94 may receive the update information in wireless connection or wired connection (USB connection) with respect to a supply source of the update information. In addition, the monitor main body portion 94 may receive the update information by replacing a memory card.

The monitor main body portion 94 may be configured such that a necessary function can be simply operated. That is, the monitor main body portion 94 may include at least one physical function key, and may be configured such that a function can be freely assigned to each of the function keys. The monitor main body portion 94, for example, may be configured such that a going-back operation can be performed with respect to the past data by performing dial operation, or a slide operation with respect to the monitor 114 (a screen).

The monitor main body portion 94 may be configured to be capable of printing data in a selected range from an external printer or the like.

The monitor main body portion 94 may be configured such that a display region of the monitor 114 can be divided, and desired data can be displayed on each of the display regions. In this case, for example, it is possible to easily compare the current data with the past data. The monitor main body portion 94 may be configured such that the display of the monitor 114 can be output to and displayed on an external display device.

The monitor main body portion 94 may be configured to estimate the range of the urinated volume from an infusion amount, to compare the estimated range with the real urinated volume, to determine whether or not the real urinated volume is within the estimated range, and to notify the determination result. Furthermore, infusion data may be automatically acquired from an infusion pump, or the infusion amount may be directly input, as the infusion amount.

The detailed description above describes an oxygen measurement device detecting oxygen in urine which is discharged from a kidney. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An oxygen measurement device, comprising:
 a catheter including a flexible hollow shaft, the flexible hollow shaft having an open port configured to allow urine from a bladder to flow into the open port, and a urinary passage in communication with the open port configured to discharge the urine;
 an oxygen sensor including an oxygen sensor main body capable of detecting oxygen in the urine, the oxygen sensor being disposed in the catheter and configured such that the oxygen sensor main body is in contact with the urine flowing in the urinary passage; and
 an optical fiber, the optical fiber being attached to the catheter in a state of being turned back on a distal end side from the urinary passage, and wherein a distal end surface of the optical fiber is positioned on a side opposite to the urinary passage sandwiching the oxygen sensor main body.

2. The oxygen measurement device according to claim 1, wherein
 the oxygen sensor main body includes a fluorescent body and a base portion, the fluorescent body being attached to the base portion of the oxygen sensor main body;
 the optical fiber formed separately from the oxygen sensor main body, the oxygen sensor main body being attached to the catheter and wherein at least a part of the fluorescent body is in contact with the urine in the urinary passage; and
 the optical fiber being attached to the catheter in a state in which a distal end surface of the optical fiber is positioned with respect to the fluorescent body, such that the fluorescent body is capable of being irradiated with excitation light or receiving fluorescence from the fluorescent body.

3. The oxygen measurement device according to claim 2, comprising:
 a distal end opening portion of a lumen of the urinary passage is formed on a distal end of the shaft;
 a distal end cap fitted into the distal end opening portion of the lumen of the urinary passage; and
 the oxygen sensor main body being attached to the distal end cap.

4. The oxygen measurement device according to claim 3, wherein the base portion of the oxygen sensor main body is configured to be capable of transmitting the excitation light from the optical fiber and the fluorescence from the fluorescent body.

5. The oxygen measurement device according to claim 4, wherein the distal end surface of the optical fiber is in contact with or close to a surface of the base portion of the oxygen sensor main body on a side opposite to a surface onto which the fluorescent body is attached.

6. The oxygen measurement device according to claim 4, further comprising:
an arrangement hole in which a turned-back portion of the optical fiber is provided, and wherein the arrangement hole is formed in the distal end cap.

7. The oxygen measurement device according to claim 6, wherein the optical fiber is attached to the distal end cap in the arrangement hole.

8. The oxygen measurement device according to claim 4, comprising:
a support portion fixed to the distal end cap; and
the base portion of the oxygen sensor main body being attached to the support portion, and a positioning hole positioning a distal end of the optical fiber is disposed in the support portion.

9. The oxygen measurement device according to claim 3, wherein
the fluorescent body is positioned on a distal end side from the open port; and
the open port having an opening width that increases along a circumferential direction towards a distal end direction of the shaft.

10. The oxygen measurement device according to claim 1, wherein the optical fiber is attached to the catheter by an adhesive agent, the adhesive agent being configured to seal a through hole formed on an outer surface of the shaft.

11. The oxygen measurement device according to claim 1, comprising:
a sensor lumen, the optical fiber being arranged in the sensor lumen, and wherein the sensor lumen is formed in a wall portion of the shaft.

12. The oxygen measurement device according to claim 1, comprising:
a hard member composed of a material harder than a material of the shaft, the hard member being disposed in the shaft.

13. The oxygen measurement device according to claim 1, comprising:
a flow velocity sensor configured to detect a flow rate of the urine being discharged through a urination discharge port, the flow velocity sensor being disposed on a wall surface of the urination discharge port.

14. An oxygen measurement device, comprising:
a catheter including a flexible hollow shaft, the flexible hollow shaft having an open port configured to allow urine from a bladder to flow into the open port, and a urinary passage in communication with the open port configured to discharge the urine;
an oxygen sensor including an oxygen sensor main body capable of detecting oxygen in the urine, the oxygen sensor being disposed in the catheter and configured such that the oxygen sensor main body is in contact with the urine flowing in the urinary passage;
a fluorescent body and a base portion, the fluorescent body being attached to the base portion of the oxygen sensor main body;
an optical fiber formed separately from the oxygen sensor main body, the oxygen sensor main body being fixed to the catheter and wherein at least a part of the fluorescent body is in contact with the urine in the urinary passage, the optical fiber being attached to the catheter in a state in which a distal end surface of the optical fiber is positioned with respect to the fluorescent body, such that the fluorescent body is capable of being irradiated with excitation light or receiving fluorescence from the fluorescent body, and wherein the optical fiber is attached to the catheter in a state of being turned back on a distal end side from the urinary passage, and wherein the distal end surface of the optical fiber is positioned on a side opposite to the urinary passage sandwiching the oxygen sensor main body; and
a balloon arranged on a distal end portion of the shaft, the shaft having a dilation lumen for circulating a dilation fluid, and wherein the balloon is configured to be inflated and deflated according to a change in internal pressure with the dilation fluid.

15. The oxygen measurement device according to claim 14, comprising:
a flow velocity sensor configured to detect a flow rate of the urine flowing through a urination discharge port, the flow velocity sensor being disposed on a wall surface of the urination discharge port.

16. The oxygen measurement device according to claim 15, further comprising:
a urine collection bag in fluid communication with urinary passage of the catheter; and
a monitoring system configured to display measurement results from the oxygen sensor.

17. A method of detecting oxygen in urine discharged from a kidney, the method comprising:
placing an oxygen measurement device in a bladder of a living body, the oxygen measurement device including a catheter having a flexible hollow shaft, the flexible hollow shaft having an open port configured to allow urine from a bladder to flow into the open port, a urinary passage in communication with the open port configured to discharge the urine, an oxygen sensor including an oxygen sensor main body capable of detecting oxygen in the urine, the oxygen sensor configured such that the oxygen sensor main body is in contact with the urine flowing in the urinary passage, a balloon arranged on a distal end portion of the shaft, and an optical fiber attached to the catheter in a state of being turned back on a distal end side from the urinary passage, and wherein a distal end surface of the optical fiber is positioned on a side opposite to the urinary passage sandwiching the oxygen sensor main body;
inflating the balloon with a dilation fluid to retain the catheter inside the bladder;
irradiating the oxygen sensor main body with an excitation light from the optical fiber; and
measuring the oxygen in the urine discharged from the bladder with the oxygen sensor.

18. The method of claim 17, further comprising:
collecting the urine from the catheter in a urine collection bag.

19. The method of claim 17, further comprising:
displaying the measured oxygen in the urine discharged from the bladder on a display device.

20. The oxygen measurement device according to claim 1, wherein the catheter is a urethral catheter.

* * * * *